(12) United States Patent
Rossello et al.

(10) Patent No.: US 8,093,386 B2
(45) Date of Patent: Jan. 10, 2012

(54) THIOARYL SUBSTITUTED INHIBITORS OF ZINC PROTEASES AND THEIR USE

(75) Inventors: Armando Rossello, Pisa (IT); Elisabetta Orlandini, Pisa (IT); Aldo Balsamo, Pisa (IT); Laura Panelli, San Filippo (IT); Elisa Nuti, Pisa (IT)

(73) Assignee: Bracco Imaging S.p.A, Milan (IT)

( * ) Notice: Subject to any disclaimer, the term of this patent is extended or adjusted under 35 U.S.C. 154(b) by 357 days.

(21) Appl. No.: 12/309,701

(22) PCT Filed: Jul. 25, 2007

(86) PCT No.: PCT/EP2007/057661
§ 371 (c)(1), (2), (4) Date: Jan. 26, 2009

(87) PCT Pub. No.: WO2008/015139
PCT Pub. Date: Feb. 7, 2008

(65) Prior Publication Data
US 2009/0239829 A1    Sep. 24, 2009

(30) Foreign Application Priority Data

Aug. 2, 2006  (IT) .............................. TO2006A0575

(51) Int. Cl.

| | |
|---|---|
| C07D 207/40 | (2006.01) |
| C07D 209/48 | (2006.01) |
| C07D 211/40 | (2006.01) |
| C07D 211/54 | (2006.01) |
| C07D 239/02 | (2006.01) |
| C07C 57/13 | (2006.01) |
| C07C 259/04 | (2006.01) |
| C07C 311/10 | (2006.01) |
| A61K 31/18 | (2006.01) |
| A61K 31/19 | (2006.01) |
| A61K 31/40 | (2006.01) |
| A61K 31/445 | (2006.01) |
| A61K 31/515 | (2006.01) |

(52) U.S. Cl. ........ 544/302; 546/216; 548/478; 548/542; 548/545; 548/547; 562/429; 562/431; 562/621; 564/85; 514/270; 514/327; 514/417; 514/425; 514/570; 514/575; 514/602

(58) Field of Classification Search .................. None
See application file for complete search history.

(56) References Cited

U.S. PATENT DOCUMENTS

| 6,303,612 B1 | 10/2001 | Kuchar et al. |
| 6,573,288 B1 | 6/2003 | Weichert et al. |
| 2003/0073845 A1 | 4/2003 | Barta et al. |

FOREIGN PATENT DOCUMENTS

| WO | WO 00/50396 A1 | 8/2000 |
| WO | WO 2005/110980 A2 | 11/2005 |
| WO | WO 2005/110980 A3 | 11/2005 |
| WO | WO 2006/021805 A1 | 3/2006 |

OTHER PUBLICATIONS

Database CAPLUS on STN, Acc. No. 1966:412160, Jilek et al., Collection of the Czechoslovak Chemical Communications (1966), 31, p. 269-278 (abstract).*
Database CAPLUS on STN, Acc. No. 1998:611997, Mcdonald et al., WO 9838859 A1 (Sep. 11, 1998) (abstract).*
PCT Search Report for PCT/EP2007/057661, mail date Feb. 27, 2008.
PCT Written Opinion for PCT/EP2007/057661, mail date Feb. 27, 2008.
Cervena, I. et al., 1-[2-(2-Hydroxymethylphenyllthio)benzyl]-4-Methylpiperazine and related compounds as potential antidepressants, Collect.Czech.Chem.Commun., vol. 49, 1984, pp. 1009-1020, XP009096062, CZ.
Dhareshwar, G.P. et al., Studies in rearrangement of 2-(arylithio) benzohydroxamic acids to the corresponding 2-(arylsulphinyl) benzamides, Indian Journal of Chemistry. Section B: Organic and Medicinal Chemistry Scientific Publishers, Jodhpur, IN, vol. 19, No. 10, 1980, pp. 831-835, XP009096019, issn: 0376-4699.
Drsata et al., Inhibition of aromatic amino acid decarboxylase by a group of new potential nonsteroidal anti-inflammatory drugs with antileukotrienic effects, ACTA Medica Lekarske Fakulty Univerzity Karlovy V Hradci Kralove, 2003, pp. 147-141, XP009909600, ISSN: 1211-4286, Karolinum, Prague, CZ. Hosangadi, BD et al., Photochemistry of Hydroxamic Acids, Tetrahedron, Elsevier Science Publishers, vol. 43, No. 22, 1987, pp. 5375-5380, XP009096009, issn: 0040-4020, Amsterdam, NL.
Jilek, J. et al., 8-Alkylthio-10-Piperazinodibenzo(b,f,)Thi epins, Collect.Czech. Chem. Commun., vol. 39, 1974, pp. 3338-3351, XP009096063, CZ.
Jilek, Jiri et al., Potential Antipressants: 2.(Methoxy- and Hydroxy-Phenylthio)Benzylamines as Selective Inhibitors of 5-Hydroxytryptamine Re-Uptake in the Brain, Collection of Czechoslovak Chemical Communications, Institute of Organic Chemistry & Biochemistry, Dec. 1, 1989, pp. 3294-3338, XP000647680, ISSN: 0010-0765, Prague, CZ.

(Continued)

Primary Examiner — Brian J Davis
(74) Attorney, Agent, or Firm — M. Caragh Noone

(57) ABSTRACT

There are described compounds having the general formula (I) below and their pharmaceutically acceptable salts thereof, wherein E, X, m, q, $R_1$, $R_2$, n and ZBG have the meanings reported in the description useful, in therapy, as inhibitors of zinc metalloproteinases.

16 Claims, No Drawings

OTHER PUBLICATIONS

Valenta, V. et al., 8-Alk7yl and 8-Cycloalkyl-10-Piperazinobibenzo[b,f]Thie pins, Collection. Czechoslov. Chem. Commun., vol. 39, pp. 783-804, XP009096127, 1974.

Kuchar, M. et al., Derivatives of (Phenylsulfanyl) Benzoic Acids With Multiple Antileukotrienic Activity, Collect.Czech.Chem.Commun., vol. 69, 2004, pp. 2098-2120, XP009096058.

Communication Pursuant to Article 94(3) EPC for EP application No. 07787889.0, mail date Dec. 1, 2009.

Jilek, J.O. et al., "Neutrotrope and Psychotrope Substance VII. 2-Alkoxy-9-(3-Dimethylaminopropyliden) Thioxanthene and—Derivate—Protein", Collection Czechoslov.Chem.Communication, vol. 31; pp. 269-278, XP009126197, Feb. 1965.

English translation for: Jilek, J.O. et al., "Neutrotrope and Psychotrope Substance VII. 2-Alkoxy-9-(3-Dimethylaminopropyliden)Thioxanthene and—Derivate—Protein", Collection Czechoslov.Chem.Communication, vol. 31; pp. 269-278, XP009126197, Feb. 1965.

* cited by examiner

THIOARYL SUBSTITUTED INHIBITORS OF ZINC PROTEASES AND THEIR USE

This application is the national stage application of corresponding international application number PCT/EP2007/057661 filed Jul. 25, 2007, which claims priority to and the benefit of the Italian application no. TO2006A000575, filed Aug. 2, 2006, all of which are hereby incorporated by reference.

The present invention relates to synthesized compounds as innovative therapeutic agents designed to inhibit, regulate and/or modulate the activity of zinc proteinases hyperexpressed in highly invasive and metastatic tumoral forms, as well as in degenerative processes on an inflammatory or immunologic base.

DESCRIPTION

More in particular, the invention relates to thioaryl substituted zinc proteinase inhibitors (also referred to as protease inhibitors) such as arylsulphides, arylsulphoxides and arylsulphones, which are able to inhibit with high selectivity of action only some isoforms of extracellular matrix metalloproteinases (MMPs) and of adamalysins, such as ADAMs (A Disintegrin and Metalloproteinases) and ADAMTs (A Disintegrin and Metalloproteinases with Thrombospondin Type I repeats), hyperexpressed in degenerated tissues of different nature. The invention is also directed to pharmaceutical compositions comprising a therapeutically effective amount of an inhibitor of the invention, as well as to the use of such inhibitors for the preparation of medicaments able to prevent, treat or find conditions related to the activity of MMPs and/or ADAMs and/or ADAMTs, especially in pathological conditions.

BACKGROUND OF THE INVENTION

The extracellular matrix (ECM) represents an important morphological structure in which cells with their projections are organized in a complex tridimensional network with physical, chemical and electrical connections. In this network, cells produce proteases which play fundamental roles in the formation, maintenance and remodelling of tissues, in the transduction of inter- and intra-cellular signals and in cellular adhesion phenomena.

When the normal mechanism of control of network are lost in specific pathological conditions such as, for instance, in degenerated tumoral tissues, inflamUmatEed tissues, in the nervous, cardiac, vascular, osteoarticular, pulmonary, hepatic, renal tissues, in the skin, mucoses and glandular tissue, an hyperexpression of some zinc proteases belonging to various families is often observed. Among them, MMPs, ADAMs and ADAMTs play a fundamental role. In physiological conditions the normal tissue remodelling is under the control of two fundamental mechanisms that regulate the expression of MMPs, ADAMs and ADAMTs: the genic expression and/or the protein activation. The proteolytic activity of these zinc metalloproteinases is regulated at tissue level by several natural inhibitors, principally TIMPs (tissue inhibitor of metalloproteinases), which exert fundamental roles in the regulation of the activity of MMPs and also of the ADAMs and ADAMTs.

The loss of one of the mechanisms of control which are able to regulate the tissue level of one of these zinc metalloproteinases in the ECM is often responsible for the development of serious degenerative processes which are characterized, beyond the alteration of the normal tissuemorphology, also by the presence and uncontrolled proliferation of cells of different type. The consequent morphological alteration leads to a tissue which has completely lost its normal characteristics and evolves in a non-physiological way.

Said alterations are typical both in highly aggressive tumoral forms and acute chronic inflammatory or immunologic pathologies. Therefore, high levels of these zinc metalloproteinases may be observed both in rapidly growing tumoral tissues and in metastasis, as well as in some pathologies of the central and peripheral nervous system, and of the cardiovascular, gastrointestinal, musculoskeletal, respiratory, renal, optical system, of the skin and of the mucosae. Diseases for which it has been demonstrated the certain pathological role related to the loss of control of the proteolytic activity of some zinc metalloproteinases include, for instance, highly metastatic tumoral forms, not solely tumoral angiogenesis, ictus and those forms with a varying degree of seriousness related to hypoxia and cerebral ischemia, atherosclerosis, Alzheimer's disease, coronary thrombosis, dilated cardiomyopathy, aortic aneurism, otosclerosis, proteinuria, multiple sclerosis, rheumatoid arthritis, osteoarthritis, septic arthritis, decubitus ulcers, pulmonary fibrosis, emphysema, periodontal disease as well as some infectious diseases.

Some of the zinc metalloproteinases present in the ECM are also involved in other biological processes such as ovulation, post-partum involution of uterus, breaking of the amyloid plaque at the level of the beta-amyloid precursor and inactivation of the protease alpha1 proteasic inhibitor (alpha1-PI). Therefore, the inhibition of such zinc metalloproteinases may represent a mechanism of control of fertility, as well as a mechanism able to increase the levels of alpha1-PI for the prevention of thological conditions such as emphysema and pulmonary, inflammatory and age-related diseases.

As long as about twenty years ago, it was thought that it was possible to use inhibitors of MMPs in a cytostatic therapeutic strategy in order to block tumours. Since then, two generations of MMPs inhibitors have been brought to clinical research, but only recently it has been foreseen the possibility that some inhibitors of MMPs might really be used in therapy [Abbenante Medicinal Chemistry, 2005, VOL 1, No. 1, 72]. The first generation inhibitors such as, for example, Ilonastat or Batimast, were highly effective but completely non-selective peptidomimetic inhibitors of MMPs. As such, they were unsuitable because they were not bioavailable through oral administration. A subsequent generation of inhibitors was developed, with molecules moderately selective towards the different MMPs; some of these inhibitors have reached phase III in clinical trial for the treatment of very aggressive forms of cancer. Nevertheless, in spite of remarkable efforts made with both classes, the research on the application of MMPs inhibitors in cancer therapy has brought discouraging results, as it was widely reported in some works [Zucker, S. Oncogene, 2000, 19, 6642; Coussens LM; Science, 2003, 295, 2387; Overall CM, et al Nat Rev Cancer, 2002, 2, 657; Fingleton B, Exp Opin Ther Thiget, 2003, 7, 385].

Nowadays only two molecules belonging to this pharmacological class are under development: Doxiciclina or Periostat, a well known tetracycline proposed for the therapy of periodontitis as inhibitor of MMP1/MMP2; and Glucosamina solfato, a well known drug today proposed as inhibitor of MMP8 in osteoarthritis.

One of the reasons for the lack of success of this pharmaceutical class of drugs, until now, has been the lack of high selectivity versus different MMPs.

At present, in fact, 24 different MMPs have been identified. Nevertheless, by using sophisticated techniques of genomics, proteomics and pharmacogenomics, only recently has it been possible to classify the different MMPs according to their single functions and physiological and pathological roles, therefore reclassifying them as therapeutic target or antitarget in the different types of pathologies. On the same basis, it has been possible to critically re-analyse some of the results obtained from the past trials. The reclassification of the various MMPs as target or antitarget has re-opened the field of research by making conceivable a third generation of inhibitors. On the basis of the knowledges acquired until now, it seems in fact possible to design drugs that might in fact be highly selective towards those MMPs which represent reliable targets for the degenerative pathologies of the extracellular matrix, such as the MMP2. More specifically, using MMP2 as the target, it is today possible to design and synthesize new effective inhibitors with high MMP1/MMP2 selectivity ratios, which show remarkable anti-invasive and anti-angiogenic properties in cellular models of highly aggressive tumours. On these basis we can today refer to MMPi target based therapy.

Also the ADAMs and the ADAMTs represent an important cellular target at the ECM level for the development of innovative drugs. These enzymes constitute a very large family: at least forty ADAMs have been characterised (twenty of them in the *Homo sapiens* species) and nearly ten ADAMTs have been isolated and sequenced from human species. These adamalysins, with their multiple physiological roles, contribute to the regulation of many cellular functions in tissues. These enzymes, strictly correlated to the more known MMPs, are zinc metalloproteinases themselves and almost always, they are anchored to the surface of the membranes exposed to the ECM and perform most of their proteolytic actions just in the ECM.

Their principal functions include the release and shedding of membrane proteins, of growth factors, of cytokines, the activation of receptors and the regulation of the cellular adhesion processes. As they have been isolated only recently, many of their actions are still unknown. Nevertheless, because of their functional and structural characteristics, they are correlated to the MMPs and some of them are inhibited by the same tissutal inhibitors which regulate the proteolytic action of MMPs, that it is to say the TIMPs. The hyperexpression of some of these adamalysins is related to the development of serious pathologies. The most known example is the ADAM17, (tumour necrosis factor alpha convertase), which normally activates the alpha-TNF and the receptors of various cytokines and also, if hyperexpressed, leads to an increase of TNF thus causing various pathologies among which are the rheumatoid arthritis, immunitary diseases, multiple sclerosis and cancer.

Also in this case, it is necessary to take advantage of the more recently acquired knowledge on the structural characteristics and the biological properties of the single adamalysins in order to design powerful and especially selective inhibitors to be proposed as potential drugs for the therapy of diseases such as, for instance, cancer, rheumatoid arthritis, ictus, atherosclerosis, multiple sclerosis, myocardial stroke and other cardiovascular diseases.

Efforts are thus devoted to extend also to the adamalysins the therapeutic approach of MMPi target based therapy previously illustrated, therefore avoiding problems and drawbacks known by the use of MMPs inhibitors which were non-selective for specific pathologies.

At present, several synthetic inhibitors of MMPs are known in the art [see, for example, Skiles J W Curr. Med. Chem. 2005, 11, 2911; Maskos, K Biochim. 2005, 87, 249; Fisher, J F et al Cancer Metastasis Rev. 2006, 25, 115]. Some of these inhibitors have been also studied and structurally modified to inhibit ADAMs [see, for example, Levin J I Curr. Top. Med. Chem. 2004, 4, 1289; Skiles J W Curr. Med. Chem. 2005, 11, 2911] and ADAMTs [see, for example, Yao, W et al J. Med. Chem. 2001, 44, 3347; WO01/87870; WO00/69839; Gavin, J. C. Curr. Pharm. Biotechn. 2006, 7, 25]. There exists, in addition, a large patent literature concerning zinc metalloproteinases inhibitors.

The most studied and described inhibitors present general structural characteristics commonly shared within the various classes: the presence of chelating groups for the catalytic zinc atom (ZBGs Zinc binding groups) which are able to give hydrogen bonds with the backbone of the target proteins and interactions of hydrophobic nature with the near pockets for the recognition of the substrate in S1, S1', S2' and in some cases S3'.

Numerous types of ZBGs have been studied so far, but the most widely known is the hydroxamic group which, giving two coordination bonds with zinc, leads to very powerful inhibitors in comparison with other chelating groups [see, as an example: WO 95/2982, WO 97/24117, WO 97/49679, EP 0780386, WO 90/05719, WO 93/20047, WO 06074, WO 00/46221, WO 00/44709, WO 99/25687, WO00/50396, WO 00/69821, WO 04/071384, WO 99/41246, U.S. Pat. No. 6,750,228, US 2004/0127524, WO 2004/052840, WO 01/02369, WO 2004/000811, US 2003/0073845, and Fisher, J F et al Cancer Metastasis Rev. 2006, 25, 115]. Other chelating groups have been reported such as, for example, carboxylate, phosphonate, thiols [see, as an example: EP 1331224; EP 107736; WO 95/12389; WO 96/11209; U.S. Pat. No. 6,500, 811; Fisher, J F et al Cancer Metastasis Rev. 2006, 25, 115; Breuer, E et al, Export Opin. Ther. Patents, 2005, 253] and many others [see, as an example: Puerta, D T et al J. Am. Chem. Soc, 2004, 126, 8388].

Very recent works in the study of the inhibitors of these zinc metalloproteinases concern the development of mechanism based inhibitors and the development of allosteric inhibitors [see, as an example: Kruger, A. et al Cancer Res. 2005, 65, 3523; US 2003/0129672, and US 2005/0004177].

Sulphonyl derivatives possessing MMPs inhibitory activity have been also disclosed in WO 00/69819 and WO 98/38859.

Among the compounds therein exemplified, some are characterized by the presence of a phenyl-sulphonyl-phenyl system bringing a carboxylate or hydroxamate group linked to a phenylene moiety, either directly or through an optionally substituted methylene group.

Today, it is clear that in order to develop a drug capable of inhibiting zinc metalloproteinases specifically produced in a determined degenerative pathology of the ECM, it is necessary to obtain highly selective inhibitors, targeted in a very specific manner against those specific metalloproteinases which are involved in the pathology of interest. For example, as pointed out before, it would be preferable to obtain high levels of selectivity of action towards MMP-2 and MMP-13 in case of potential inhibitors to be designed-for the anticancer therapy, with a contemporaneous low inhibition property against MMP-1, whose inhibition is known to cause musculoskeletal syndrome with fibroproliferative effects in the kneecaps [see, as an example: Hutchinson, J. W et al Bone Joint Surgery 1998, 80, 907; 18; Holmbeck, K. et al Cell 1999, 99, 81; Steward, W. P. Cancer Chemother. Pharmacol. 1999, 43, S56], against MMP-3, MMP-8 and MMP-9, which have been recently validated as antitarget for this kind of therapy [see, as an example: Overall CM, et al Nature Rew Cancer, 2006, 6, 227].

On the other hand, in the field of zinc metalloproteinases inhibitors to be used in degenerative non-tumoral pathologies, it would be advisable to obtain high levels of selectivity for MMP2, MMP8, MMP9, MMP13 and MMP14 [see, as example: Ishikawa, T et al Br. J. Pharm. 2005, 144, 133; Martel-Pelletier, J et al Best Pract. & Res. Clin. Rheum., 2001, 805-829] and for adamalysins as TACE (ADAM17) and ADAMTs-4 (aggrecanase-1) [see, as an example: US 2004/0110805; U.S. Pat. No. 5,770,624; WO 00/44709; US 2004/0110805; U.S. Pat. No. 6,500,811; Martel-Pelletier, J et al Best Pract. & Res. Clin. Rheum., 2001, 805-829].

Moreover, it would be preferable to replace the hydroxamate group (ZBG) with different clusters, less toxic, more stable in metabolism, more bioavailable and well absorbable via oral administration [see, as an example: Fisher, J F et al Cancer Metastasis Rev. 2006, 25, 115; Breuer, E et al Exp. Opin. Ther. Patents 2005, 15, 253; US 2005/6953788]Recently, the need to develop suitable diagnostic instruments for non-invasive technologies has been highlighted, such as PET (Positron Emission Tomography), SPECT (Single Photon Emission Tomography), MRI (Magnetic Resonance Imaging), OI (Optical Imaging) and Rx, able to find with high specificity degenerated tissues due to the hyperactivity of zinc metalloproteinases such as, for example, MMP2, MMP8, MMP9, MMP13, MMP14, TACE and ADAMTs1 and ADAMTs4[see, as example: Schafers, M. et al Basic Science Rep. 2004, 11, 2554; Zheng, Qi-H et al Nucl. Med. Biol. 2002, 29, 761; Fei, X et al, Bioorg. & Med. Chem. Lett. 2003, 13, 2217; Zheng, Qi-H et al Nucl. Med. Biol. 2003, 30, 753; Kopta, K et al, Nucl. Med. Biol. 2004, 31, 257; Li, W P et al Q. J Nucl. Med. 2003, 47, 201; Haumber, R Curr. Pharm. Des. 2004, 10, 1439; WO 2005/049005].

Given the relevance of the inhibitors of zinc metalloproteinases in the prevention, treatment and/or diagnosis of pathological conditictns characterized by the absence of the normal tissue morphology and by the presence and uncontrolled proliferation of cells of different nature caused by loss of the physiological mechanisms of control in the ECM, and also considering the knowledge acquired in clinical trials on the known zinc metalloproteinases inhibitors, it would be very important to have new classes of molecules able to act with high selectivity and potency of action against some proteases specifically hyperexpressed in the various pathologies. In particular, it would be very important to have highly selective and powerful inhibitors for MMP2, MMP13 or MMP16, or for MMP2 and MMP14 (as for MMPs) or for TACE (for ADAMs) or again for ADAMTs1 and ADAMTs4 (for ADAMTs), which would be lacking as much as possible the inhibitory activity toward MMP1 and, according to the pathology, also toward MMP14.

At the same time, it would be highly desirable to have inhibitors less toxic, more metabolically stable, more bioavailable and well absorbable via oral administration, than the inhibitors known in the art.

These and other aims have been achieved by the thioaryl substituted zinc proteinase inhibitors of the present invention.

Said compounds are, in fact, able to inhibit the activation of specific MMPs (such as MMP2, MMP9, MMP13, MMP14 or MMP16) and/or ADAMs (such as TACE) and/or ADAMTs (such as ADAMTs1 or ADAMTs4) which are hyperexpressed in various degenerative diseases.

The compounds of the invention share a thioarylether type structure. This kind of structure allowg to modulation of the selectivity of the inhibitory action over various zinc proteases, according to the structural features of the compounds themeselves including: the oxidation state of the sulphur atom as sulphide, sulphoxide or sulphone (—S—, —SO— or —SO$_2$—, respectively); the nature of the .zinc chelating group (ZBG) as well as the nature of the groups bound to it at P1, P1' and P2'.

Generally, the compounds of the invention are inactive or scarcely active towards some MMPs such as MMP1, MMP3, MMP8 and MMP14, thus advantageously providing a reduction of therapeutic risk in relation to some tumoral pathologies in which these enzymes have been defined as antitarget [see, as example: Overall C M, et al Brit J of Cancer, 2006, 1; and Overall C M, et al Nature Rew Cancer, 2006, 6, 227].

In addition, thanks to their marked selectivity of action, the compounds of the invention are less cytotoxic than the inhibitors of the zinc proteinases known in the art.

As set forth below, the compounds of the invention may be thus used for preventive, therapeutic and cosmetic purposes and, also, as possible carriers of both diagnostic and therapeutically active agents, both in the field of medicine and veterinary medicine.

DETAILED DESCRIPTION OF THE INVENTION

It is thus a first object of the present invention a compound of formula (I)

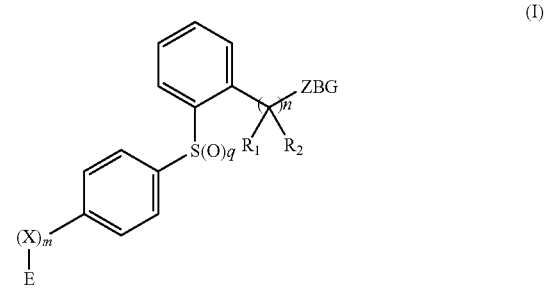

wherein:
q is 0, 1 or 2;
n is 0 or 1;
ZBG is the chelating moiety for the catalytic zinc atom and it is selected from the group consisting of:
hydroxamate —CONHOH;
carboxylate —COOH;
carboxamide —CONHR$_4$, —CON(R$_4$)$_2$ or —CONR$_6$R$_7$;
phosphonate —P(═O) (R$_4$)OH;
sulfonimide —CONHSO$_2$ (R$_{14}$);
sulfonamide —SO$_2$NHR$_4$; thiol —SH;
or it is a group of formula:

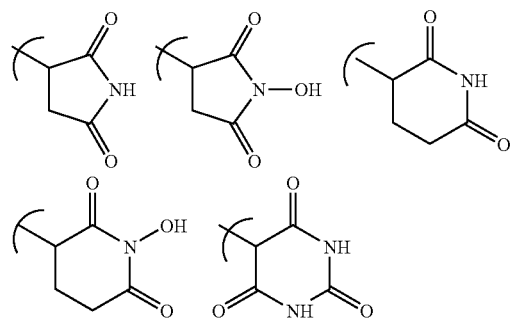

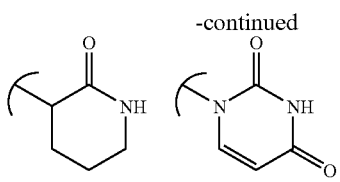

$R_4$ is selected, independently in each occurrence, from the group consisting of hydrogen, hydroxyl, straight or branched $C_1$-$C_{10}$ alkyl or fluoroalkyl, optionally substituted aryl or 5 to 6 membered heteroaryl with from 1 to 2 heteroatoms or heteroatomic groups selected from N, NH, O or S; or $R_4$ is a group selected from —$(CHR)_p$—COOH, —$(CHR)_p$—CO—NHR', —$(CHR)_p$—$NH_2$, —$(CHR)_p$—NH—COR', —$(CHR)_p$—$CH_2$—OH or —$(CH_2)_p$—CHR—OH;

p is an integer from 1 to 8;

R' is a straight or branched $C_1$-$C_6$ alkyl or an optionally substituted aryl or heteroaryl group as above defined;

R is selected from the group consisting of hydrogen, a $C_1$-$C_{10}$ saturated or unsaturated, either straight or branched, chain of carbon atoms optionally substituted by one or more substituents selected from hydroxyl, —$ONO_2$, —$NR_6R_7$, —COOH, —CONHR", —NHCOR", $C_1$-$C_6$ alkoxy, or optionally substituted aryl or heteroaryl groups as above defined;

$R_6$ and $R_7$ are selected, each independently, from hydrogen, a $C_1$-$C_6$ saturated or unsaturated, either straight or branched, chain of carbon atoms optionally substituted with aryl or heteroaryl groups as above defined, or by a group selected from —CO-alkyl, —CO-aryl, —CO-heteroaryl, —CONH-alkyl, —CONH-alkyl-$ONO_2$, —CONH-acyl, —CONH-acyl-$ONO_2$, —CONH-aryl, —CONH-heteroaryl, —$SO_2$-alkyl, —$SO_2NH_2$, —$SO_2NH$-alkyl, —$SO_2NH$-aryl, —$SO_2NH$-heteroaryl;

or, together with the nitrogen atom to which they are linked, $R_6$ and $R_7$ form a 5 to 6 membered heterocyclic ring optionally further containing an additional heteroatom or heteroatomic group selected from N, NH, O or S, optionally substituted and/or benzocondensed;

R" is selected from a straight or branched $C_1$-$C_6$ alkyl, alkyl-O—$NO_2$ or acyl group, or it is an optionally substituted aryl, heteroaryl, arylalkyl, heteroarylalkyl, acylaryl or acylheteroaryl group;

$R'_4$ is selected, independently in each occurrence, from the meanings of $R_4$ except than hydrogen;

$R_1$ and $R_2$ are selected, each independently, from the meanings of R or, together with the carbon atom to which they are linked, $R_1$ and $R_2$ form an optionally substituted 3 to 6 membered carbocyclic or heterocyclic ring having from 1 to 2 heteroatoms or heteroatomic groups selected from N, NH, N—COR", O or S;

m is 0 or 1;

X is an oxygen (—O—) or sulphur (—S—) atom or it is a divalent group selected from —S—S-(disulphide), —SO— (sulphoxide), —$SO_2$— (sulphone), —NH— (amino), —NH-acyl-, a straight or branched alkylene, alkenylene, alkynylene, —O-alkylene, —O-alkenylene or —O-alkynylene with from 1 to 6 carbon atoms in the hydrocarbon chain;

E is a straight or branched alkyl, alkenyl or alkynyl group with from 1 to 6 carbon atoms in the hydrocarbon chain, or it is an optionally substituted and/or benzocondensed, either aliphatic or aromatic, 5 to 6 membered carbocyclic or heterocyclic ring having 1 or 2 heteroatoms or heteroatomic groups selected from N, NH, O or S;

with the proviso that when q is 2, ZBG is other than hydroxamate [—CONHOH] or carboxylate [—COOH]; and the pharmaceutically acceptable salts thereof.

The compounds of formula (I) may have one or more asymmetric carbon atom, otherwise referred to as chiral carbon atom, and may thus exist in the form of single enantiomers, racemates, diastereoisomers and any mixture thereof, all to be intended as comprised within the scope of the present invention.

In the present description, unless otherwise provided, within the compounds of formula (I) the parameter q may correspond to 0, 1 or 2, so as to give rise to sulphides, sulphoxides or sulphones, respectively.

As far as the parameter n is concerned, it may correspond to 0 or 1 so as to give rise to compounds of formula (I) wherein the group therein defined as ZBG is linked to the phenylene ring, either directly (n=0) or through the optionally substituted methylene —C($R_1$)($R_2$)— group (n=1).

Substantially analogous considerations apply to the parameter m; within formula (I), in fact, E may be linked to the phenylene ring either directly (m=0) or through X (m=1).

In the present description, unless otherwise provided, the ZBG group is defined as formerly reported and may also assume the meanings of any of the 5 or 6 membered heterocycles above defined. As before, the said heterocyclic groups may be linked to the rest of the molecule either directly or through the optionally substituted methylene —C($R_1$)($R_2$)— group.

As an additional remark, in case ZBG represents a carboxamido group —CON($R_4$)$_2$, those same $R_4$ groups may be independently selected from each other and may thus assume any of the meanings above defined for $R_4$.

Unless otherwise provided, within the meanings of $R_4$ there are straight or branched alkyl groups having from 1 to 10 carbon atoms among which are, as an example, methyl, ethyl, n-propyl, isopropyl, n-butyl, isobutyl, sec-butyl, tert-butyl, pentyl, hexyl, decyl, and the like.

Particularly preferred, among them, are straight or branched $C_1$-$C_4$ alkyl groups; methyl and ethyl being even more preferred.

With the term fluoroalkyl chain we intend, unless otherwise provided, any of the above $C_1$-$C_{10}$ alkyl groups wherein one or more hydrogen atoms are replaced by fluorine atoms so as to give rise to fluorinated or even perfluorinated alkyl groups. Particularly preferred, among them, are straight or branched $C_1$-$C_4$ perfluorinated alkyl groups; trifluoromethyl being even more preferred.

With the term aryl or heteroaryl group we intend, unless otherwise provided, any conventionally known aromatic hydrocarbon, either carbocyclic or heterocyclic, the latter having 5 or 6 members.

Typical examples of aryl or heteroaryl groups according to the invention may thus comprise phenyl and those aromatic heterocycles such as furan, thiophene, 1H-pyrrole, 1H-imidazole, 1H-1,2,4-triazole, pyridin, pyrimidin, pyridazin, and the like.

Among the aryl or heteroaryl groups, phenyl, pyridyl and thienyl are particularly preferred.

As above reported, the said aryl or heteroaryl groups may be optionally substituted by one or more substituents (hereinafter referred to as $R_5$ groups).

As such, phenyl groups may be thus mono-, di- or tri-substituted in ortho, meta and/or para positions.

Analogous considerations apply for heteroaryl groups which may be substituted by one or more $R_5$ substituents in any of their free positions.

Suitable substituents for the said aryl or heteroaryl groups may thus include, for instance, —$CH_3$, —$CH_2CH_3$, —$CH(CH_3)_2$, —$CH_2OH$, —$CH_2ONO_2$, —$(CH_2)_rCO_2H$, —$(CH_2)_r$CONH-alkyl, —$(CH_2)_r$CONH-aryl, —$(CH_2)_r$CONH-heteroaryl, —$(CH_2)_rNH_2$, —$(CH_2)_r$NHCO-alkyl, —$(CH_2)_r$NHCO-aryl, —$(CH_2)_r$NHCO-heteroaryl, —$(CH_2)_rCH_2OH$ (with r=1-8), —$CF_3$, —$NO_2$, OH, F, Cl, Br, I, —$OCH_3$, —$OCH(CH_3)_2$, —$O(CH_2)_rCOOH$, —$O(CH_2)_rNH_2$, —$O(CH_2)_rCH_2OH$ (with r=1-8), —$SO_sCH_3$, —$SO_sCH(CH_3)_2$, —$SO_s(CH_2)_rCOOH$, —$SO_s(CH_2)_rNH_2$, —$SO_s(CH_2)_rCH_2OH$ (with r=1-8 and s=0-2), —$SO_2NH_2$, —$SO_2$NH-alkyl, —$SO_2$NH-aryl, —$SO_2$NH-heteroaryl, —NH-alkyl, —NH-aryl, —NH-heteroaryl, —NHCO-alkyl, —$NHSO_2$-alkyl, —$NHSO_2$-aryl, —$NHSO_2$-heteroaryl, and the like. Particularly preferred substituents of the above aryl or heteroaryl groups may thus include $C_1$-$C_4$ alkoxy, alkylthio and alkylsulphonyl groups.

Even more preferred, within them are methoxy, methylthio and methylsulphonyl.

As far as the meanings of R' is concerned it may represent an alkyl group or an optionally substituted aryl or heteroaryl group, as above defined.

Unless otherwise provided, within the meanings of R, in formula (I), there are straight or branched, either saturated or unsaturated, $C_1$-$C_{10}$ hydrocarbon chains.

Clearly, as the saturated chains are known to correspond to the above reported $C_1$-$C_{10}$ alkyl groups, any unsaturated chain thus comprises any of the $C_2$-$C_{10}$ alkenyl or alkynyl groups among which are, for instance, vinyl, allyl, propinyl, butenyl, butinyl, hexenyl, and the like.

The said saturated or unsaturated $C_1$-$C_{10}$ hydrocarbon chains, in addition, may be optionally substituted as above defined within the definition of R.

As far as the meanings of $R_6$ and $R_7$ are concerned, in formula (I), any previous comment about the meanings of alkyl, aryl or heteroaryl may apply as well.

With the term acyl, unless otherwise provided, we intend any of the groups conventionally identifiable as Alk(CO)— groups wherein the Alk residue just represents any straight or branched $C_1$-$C_6$ alkyl group.

Suitable examples of acyl groups may thus include acetyl ($CH_3CO$—), propionyl ($CH_3CH_2CO$—), butirryl [$CH_3(CH_2)_2CO$—], isobutirryl [$(CH_3)_2CHCO$—], valeryl [$CH_3(CH_2)_3CO$—], and the like.

In addition to the above, $R_6$ and $R_7$ may also form a 5 to 6 membered heterocyclic ring together with the nitrogen atom to which they are linked.

The said heterocycles, moreover, may be also benzocondensed and/or substituted by one or more groups among which are, for instance, $C_1$-$C_4$ alkyl or alkoxy groups or even oxo groups (e.g. carbonyl groups).

Suitable examples of the said —$NR_6R_7$ heterocycles may thus comprise:

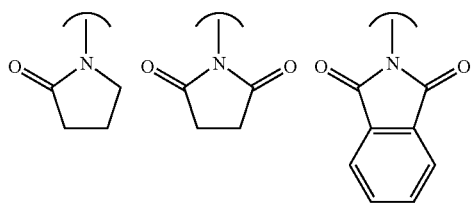

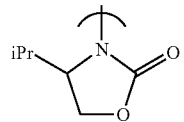

With respect to the meanings of R", in formula (I), reference is herewith given to any previous definition concerning alkyl, acyl, aryl or heteroaryl groups.

From the above, any composite-name group such as arylalkyl, alkylaryl, alkylheterocyclyl, heterocyclylalkyl and the like, should be clear to the skilled person.

Just as an example, and unless otherwise provided, with the term alkylaryl we intend any aryl group further substituted by alkyl; with the term arylalkyl we instead refer to an alkyl group further substituted by aryl.

With respect to the meanings of $R'_4$, in formula (I), it may represent any of the groups being reported for $R_4$ other than hydrogen.

As far as the meanings of $R_1$ and $R_2$ are concerned, in formula (I), they may correspond to any of the groups being reported for R or, alternatively, they may form a carbocyclic or heterocyclic ring together with the carbon atom to which they are bonded.

Preferably, the said ring is selected from a $C_3$-$C_6$ cycloalkyl or a $C_4$-$C_6$ heterocyclic aliphatic ring such as, for instance, azetidine, pyrrolidine, piperidine, piperazine, imidazoline, exahydropyrimidine, oxetane, tetrahydrofuran, tetrahydropyran, "tiano", tetrahydrothiophene, tetrahydrothiopyran, and the like.

The said carbocyclic or heterocyclic rings may be optionally substituted by one or more substituents, hereinafter shortly referred to as $R_8$ groups including, for instance, $C_1$-$C_6$ saturated or unsaturated, either straight or branched, hydrocarbon chains, or groups selected from aryl, arylalkyl, heteroaryl, heteroarylalkyl, —COOH, —COO-alkyl, —COO-aryl, —COO-heteroalkyl, —COO-alkylaryl, —COO-alkylheteroaryl, —CO-alkyl, —CO-aryl, —CO-heteroaryl, —CONH-alkyl, —CONH-alkyl-$ONO_2$, —CONH-acyl, —CONH-acyl-$ONO_2$, —CONH-aryl, —CONH-heteroaryl, —$SO_2$-alkyl, —$SO_2NH_2$, —$SO_2$NH-alkyl, —$SO_2$NH-aryl or —$SO_2$NH-heteroaryl groups. Preferred examples of the said (>$CR_1R_2$) rings may thus include:

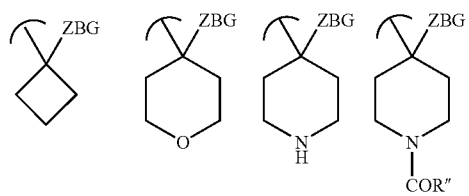

With respect to the meanings of X, in formula (I), it should be clear to the skilled person that, if present (with m=1), it represents a divalent group linking E with the phenylene ring.

Among the meanings herewith provided for X, there are also included $C_1$-$C_6$ alkylene, alkenylene, alkynylene, —O-alkylene, —O-alkenylene and —O-alkynylene chains such as, for instance, —$CH_2$—, —$(CH_2)_2$—, —$(CH_2)_6$—, —CH=CH—, —CH=CH—$CH_2$—, —$CH_2$—CH=CH—, —$CH_2$—$CH_2$—C≡C—, —$CH_2$—C≡C—$CH_2$—, —O—$CH_2$—, —O—$CH_2$—$CH_2$—$CH_2$—, and the like.

With respect to the meanings of E, in formula (I), it may represent any of the formerly defined alkyl, alkenyl or alkynyl groups or, alternatively, it represents an aliphatic or aromatic, either carbocyclic or heterocyclic, 5 to 6 membered ring as above reported.

The said ring, in addition, may be further substituted in any of their free positions by one or more substituents, hereinafter shortly referred to as $R_3$ groups.

Suitable examples of the said $R_3$ substituents may thus include straight or branched $C_1$-$C_8$ alkyl (in its turn optionally substituted with a carboxylic, aminic or oxydrilic group), oxydril, $C_1$-$C_7$ alkoxy (in its turn optionally substituted with a carboxylic, aminic or oxydrilic group), phenoxy, trifluoromethyl (—$CF_3$), nitro (—$NO_2$), F, Cl, Br, I, —$NH_2$, —NH-alkyl, —NH-acyl, —NH-aryl, —NH-heteroaryl, —NH-$CONH_2$, —$NHSO_2$-alkyl, —NH—$SO_2$-aryl, —NH—$SO_2$-heteroaryl, —S-alkyl, —SO-alkyl, —$SO_2$-alkyl, wherein the alkyl moiety, in its turn, may be optionally substituted with a carboxylic, aminic or oxydrilic group, or by —$SO_2NH_2$, —$SO_2$NH-alkyl, —$SO_2$NH-aryl, —$SO_2$NH-heteroaryl, optionally substituted phenyl, pyridyl, thienyl, morpholyl, piperidinyl or piperazinyl.

From all of the above, preferred examples of the —(X)m-E system may thus include alkoxy or alkylthio groups such as methoxy or methylthio; alkynyloxy groups such as 2-butinyloxy; aromatic, either carbocyclic or 5 or 6 membered heterocyclic, rings such as phenyl, pyridyl or thienyl; substituted aromatic rings such as methoxyphenyl or methylthiophenyl; optionally substituted aryloxy groups such as phenoxy or methoxyphenoxy; and the like.

As formerly reported, the compounds of the invention may be used as such or as salt derivatives obtained with inorganic or organic acids or bases. On the basis of the particular compound, a given salt may present advantages due to one or more physical properties, such as an increased pharmaceutical stability at different temperatures and moisture or improved solubility in aqueous or oily medium. In some cases a salt of a compound may be used during the isolation, the purification and/or the resolution of the compound. If a salt is destined to be administered to a patient (or if it is destined to be used in an in vitro or in vivo assay), it must be preferably in an acceptable pharmaceutical form. Pharmaceutically acceptable salts comprise salts with alkaline metals and salts of the free acids or bases. In general, these salts may be prepared with conventional methods by reacting a compound of the present invention with the appropriate acid or base. Pharmaceutically acceptable salts of present invention compounds may be prepared from inorganic or organic acids. Examples of inorganic acids usable for the preparation of the salts are: hydrochloric, hydrobromic, hydroiodic, nitric, sulphuric, phosphoric. Usable organic acids are, for instance: formic, acetic, trifluoroacetic, propionic, and the like.

Pharmaceutically acceptable bases to form the salts of the compounds of the present invention may be inorganic or organic. The preferred metallic salts may be with alkali or alkaline-earth metals and other salts with physiologically acceptable metals. The salts may also be formed with aluminium, calcium, lithium, magnesium, potassium, sodium and zinc. The preferred organic salts may be prepared from tertiary amines and from quaternary ammonium salts.

Preferred compounds of the invention are the derivatives of formula (I) wherein q is 0, 1 or 2; n is 0 or 1; if present, $R_1$ and $R_2$ are both hydrogen atoms or one of them is hydrogen and the other one is selected from an optionally substituted straight or branched $C_1$-$C_4$ alkyl or alkenyl group or, taken together with the carbon atom to which they are linked, $R_1$ and $R_2$ form an optionally substituted, either carbocyclic or heterocyclic, 4 to 6 membered ring; ZBG is a group selected from —CONHOH, —COOH, —$CONHR_4$, —$CONR_6R_7$, —$CONHSO_2(R'_4)$, —$SO_2NHR_4$, —SH, —P(=O)($R_4$)(OH) wherein $R_4$, $R'_4$, $R_6$ and $R_7$ have the above reported meanings; or ZBG is a group as set forth below

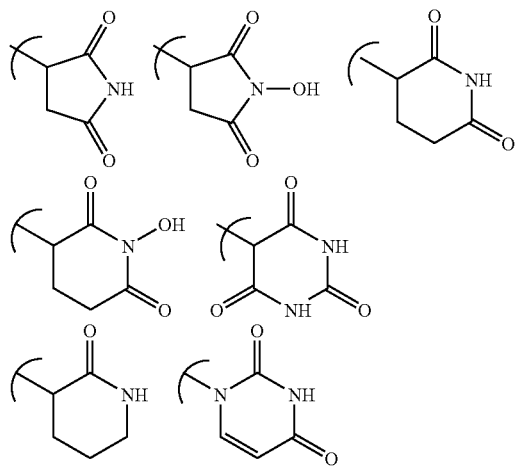

m is 0 or 1; X, whenever present, is —O—, —S— or —O-alkylene; and E is any of the $C_1$-$C_6$ alkyl, alkenyl or alkynyl groups or it is an optionally substituted and/or benzocondensed 5 to 6 membered ring as above reported.

A first preferred embodiment of the invention is thus represented by the compounds of formula (I) wherein q, n and m are all 0, and E and ZBG are as above defined.

An additional preferred embodiment of the invention is represented by the compounds of formula (I) wherein q and n are 0, m is 1, and X, E and ZBG are as above defined.

An additional preferred embodiment of the invention is represented by the compounds of formula (I) wherein q is 0, n is 1, m is 0, and E, $R_1$, $R_2$ and ZBG are as above defined.

An additional preferred embodiment of the invention is represented by the compounds of formula (I) wherein q is 0, n and m are both 1, and X, E, $R_1$, $R_2$ and ZBG are as above defined.

An additional preferred embodiment of the invention is thus represented by the compounds of formula (I) wherein q is 1, n and m are both 0, and E and ZBG are as above defined.

An additional preferred embodiment of the invention is represented by the compounds of formula (I) wherein q is 1, n is 0, m is 1, and X, E and ZBG are as above defined.

An additional preferred embodiment of the invention is represented by the compounds of formula (I) wherein q is 1, n is 1, m is 0, and E, $R_1$, $R_2$ and ZBG are as above defined.

An additional preferred embodiment of the invention is represented by the compounds of formula (I) wherein q, n and m are all 1, and X, E, $R_1$, $R_2$ and ZBG are as above defined.

An additional preferred embodiment of the invention is thus represented by the compounds of formula (I) wherein q is 2, n and m are both 0, and E and ZBG are as above defined.

An additional preferred embodiment of the invention is represented by the compounds of formula (I) wherein q is 2, n is 0, m is 1, and X, E and ZBG are as above defined.

An additional preferred embodiment of the invention is represented by the compounds of formula (I) wherein q is 2, n is 1, m is 0, and E, $R_1$, $R_2$ and ZBG are as above defined.

An additional preferred embodiment of the invention is represented by the compounds of formula (I) wherein q is 2, n and m are both 1, and X, E, $R_1$, $R_2$ and ZBG are as above defined.

More preferred, in the above classes, are the compounds of formula (I) wherein:
ZBG is selected from the group consisting of —CONHOH, —COOH, —CONHSO$_2$CH$_3$, —CONHSO$_3$H, —CONHSO$_2$CF$_3$, —P(=O) (OH)$_2$, —CONH$_2$, —SO$_2$NH$_2$, —SH, a group —CONR$_6$R$_7$ having formula below

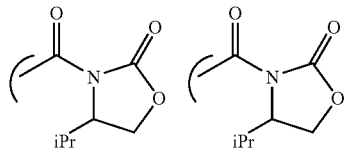

or a group of formula

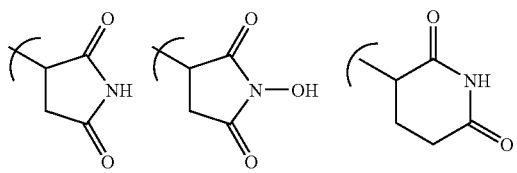

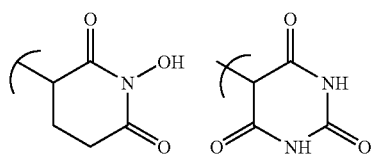

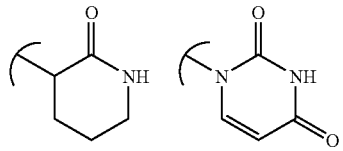

X, whenever present, is selected from —O—, —S—, —O—CH$_2$—CH$_2$—CH$_2$—;
E is selected from the group consisting of methyl, 2-butinyl, methoxyphenyl, methylthiophenyl, methylsulphonylphenyl, methylsulphonephenyl, thienyl, pyridyl or phthalimido;
R$_1$ and R$_2$, whenever present and each independently, are selected from hydrogen, methyl, ethyl, isopropyl, 2-propenyl, aminoethyl, —CH$_2$—COOH, —(CH$_2$)$_2$—NH—COOH, —(CH$_2$)$_2$—COOH or —(CH$_2$)$_2$-phthalimido or, taken together with the carbon atom to which they are bonded, form a group of formula

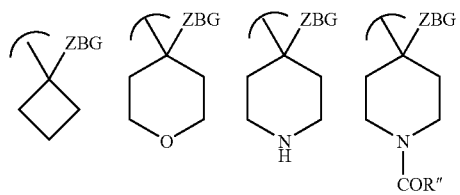

Even more preferably, within the above compounds of formula (I) wherein q, E, m, X, n, R$_1$ and R$_2$ are as above defined, ZBG is a group selected from —COOH, —CONHSO$_2$CH$_3$, —CONHSO$_3$H, —CONHSO$_2$CF$_3$, —P(=O) (OH)$_2$, —CONH$_2$, —SO$_2$NH$_2$, —SH, a group —CONR$_6$R$_7$ having formula below

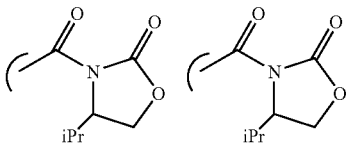

or a group of formula

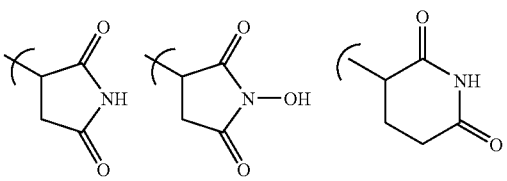

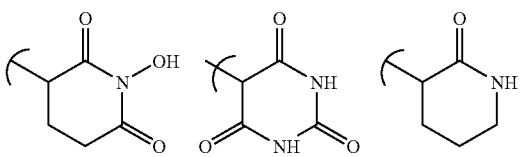

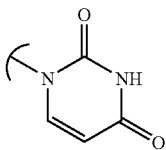

Specific examples of inhibitors of zinc proteinases according to the invention are reported in the following experimental section.

Preparation Procedures

According to an additional embodiment of the invention there is the process for the preparation of the compounds of formula (I) and the salts thereof, as per the following description.

Other compounds and salts of the present invention may be prepared using the illustrated methods in these examples, alone or in combination with other methods which are known in the art.

Said known methods include, among others, those reported in the patent applications WO 99/25687, WO 00/50396, WO 00/69821, WO 00/69839, WO 02/092588, WO 04/000811, EP 1515951 and US 2006/074243, all herewith incorporated by reference.

The following description reports general methods, which are provided by way of examples, for the preparation of some exemplary compounds of the invention, through chemical transformations.

The general scheme below reported provides general synthetic methods useful for the synthesis of the inhibitors of formula (I).

General Scheme

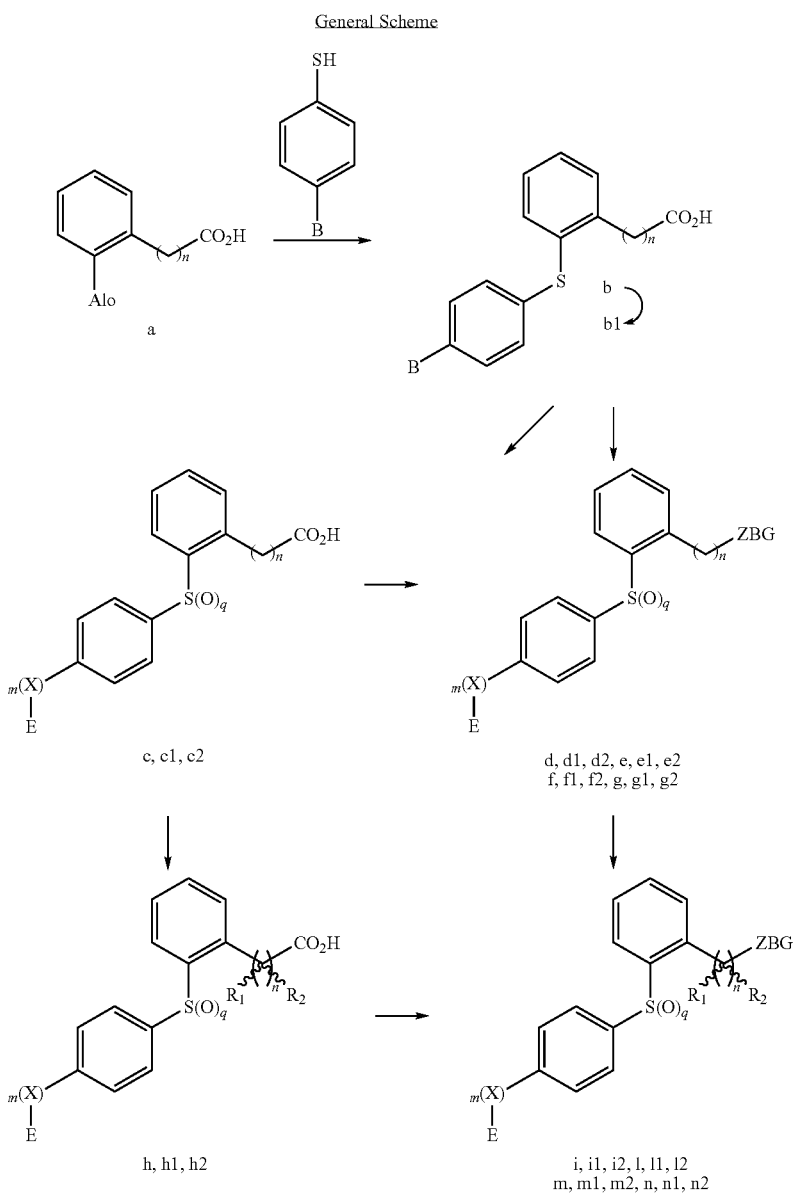

In the general scheme, as it should be clear to the skilled person, the following abbreviations have been used: Alo stands for halogen, preferably Cl, Br or I; B stands for halogen such as F, Cl, Br or I, or it is oxydril or boronic acid [—B(OH)$_2$]; ZBG, like any of the parameters or groups n, q, m, X, E, $R_1$ and $R_2$, have the meanings reported in general formula (I).

In particular, starting from a suitable 2-halo-phenyl substituted carboxylic acid (a) it is possible, by selecting appropriate reaction conditions (for instance those known for Ullman reaction), to substitute the Alo group with any suitable para-substituted thiophenol, so as to obtain diphenylsulphides of type (b).

By starting from suitable derivatives (b) wherein B represents Br or I or even an O-triflate group (OTf), and by working according to known methods [see, as an example, Kota S. et al, *Tetrahedron*, 2002, 58, 9633], corresponding boronic acid derivatives (b1) may be obtained.

The intermediate (b) may be also converted into the derivative (c) [with q=0] by replacing B, in the appropriate conditions, with E-B(OH)$_2$ or E-Alo. The sulphides (c) may thus represent themselves a possible compound of formula (I) in which ZBG is carboxyl.

Moreover, derivatives (c) may be oxidized to sulphoxides (c1) [with q=1], also optically active, or into sulphones (c2) [with q=2], by working according to known methods and by using suitable oxidants of various nature, in appropriate conditions.

The carboxylic acid derivatives (c, c1 and c2) may be then converted, by working according to known methods in the presence of suitable reactants and condensing agents, into other derivatives of formula (I) having ZBG other than carboxylate.

As an example, conversion into derivatives having ZBG as corresponding to hydroxamate [—CONHOH] (d, d1 and d2 having q corresponding to 0, 1 or 2, respectively) may be obtained by reacting the carboxylic acid with suitable hydroxylamine derivatives such as, for instance, O-(tert-butyldimethylsilyl)hydroxylamine, and in the presence of condensing agents like, for instance, EDC or DCC.

Likewise, conversion of the carboxylic acid into the derivatives having ZBG as corresponding to previous groups other than carboxylate may occur as well; see, for instance, the preparation of compounds having ZBG as corresponding to [—CONHSO$_2$R'$_4$] (e, e1 and e2 having q corresponding to 0, 1 or 2, respectively).

Carboxylic acids may be also converted according to known methods in the corresponding amides wherein ZBG is any of the groups [—CONHR$_4$, —CON(R$_4$)$_2$ and —CONR$_6$R$_7$]. Some of these carboxamides, in their turn, may be also sulphonylated, according to known methods, into the compounds having ZBG as corresponding to acylaminosulphonic acid [—CONHSO$_3$H] (f, f1 and f2 having q corresponding to 0, 1 or 2, respectively).

In addition, compounds of formula (I) wherein ZBG is carboxylate and n is 0 can be reduced, according to known methods, to the corresponding benzyl alcohols to be then converted into the corresponding phosphonate derivatives. Conversion may occur either by reacting the benzyl alcohol themselves, in the presence of suitable condensing agents, or by reacting derivatives thereof like benzyl halides (Cl, Br or I) or mesylate, with suitable alkylphosphites or phosphates. Through hydrolysis of the phosphonates, compounds of formula (I) wherein ZBG is phosphonic acid [—P(OH)$_3$] may be obtained (g, g1 and g2 having q as 0, 1 or 2, respectively).

The carboxylic acids (c, c1 and c2) with n=1, or the esters thereof, may be also alkylated, even under enantioselective conditions by using suitable chiral auxiliaries, so as to provide compounds of formula (I) with suitable R$_1$ or/and R$_2$ substituents (h, h1 or h2 with q as 0 µl or 2, respectively).

As above, these latter compounds may be then converted so as to provide compounds with ZBG groups other than carboxylate: e.g. hydroxamates [—CONHOH] (l, l1 or l2), acylmethanesulphonamides [—CONHSO$_2$R$_4$] (m, m1 or m2), acylaminosulphonic acid [—CONHSO$_3$H] (n, n1 or n2), all of which having q as 0, 1 or 2, respectively.

Finally, also the phosphonic acids (g, g1, g2) or the proper esters thereof, with n=1 may be suitably alkylated, even under enantioselective conditions in the presence of proper auxiliaries, so as to provide phosphonic acids derivatives with ZBG as —P(OH)$_3$, substituted in R$_1$ or/and R$_2$, of type (o, o1 or o2 with q as 0, 1 or 2, respectively).

The following schemes 1-7 illustrate, in a more detailed manner, the synthetic approaches being used for the preparation of some representative compounds of the invention.

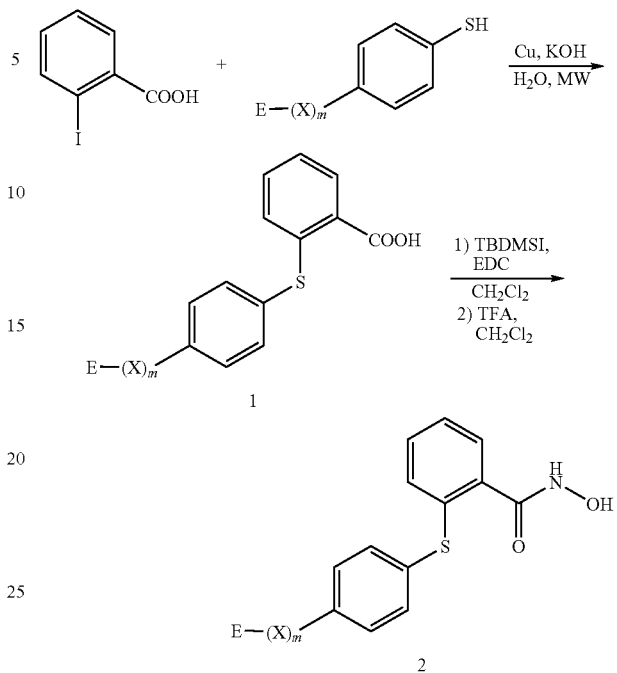

In Scheme 1 above, it has been reported the synthetic pathway for the synthesis of 4-(X)m-E substituted N-hydroxy-2-(4-phenylsulphonyl)-benzamidic compounds of type 2.

By a microwave-assisted "Ullman" type reaction between 2-iodobenzoic acid and an appropriate 4-(X)m-E-thiol, it is possible to obtain the carboxylic acids 1, which can be converted into the corresponding hydroxamic acids 2, by a coupling reaction with O-(tert-butyldimethylsilyl)hydroxylamine and subsequent deprotection with trifluoracetic acid. Other methods are known in the art for preparing hydroxamates from carboxylates and may apply as well to the preparation of the compounds of the invention.

In addition, from the above scheme 1 and comments thereof, it is clear for the skilled person that the above method may also apply to the preparation of the hydroxamates of the invention wherein the ZBG group is linked to the phenylene through the optionally substituted methylene (—CR$_1$R$_2$—) group, essentially as follows:

—C$_6$H$_4$—CR$_1$R$_2$—COOH→→—C$_6$H$_4$—CR$_1$R$_2$—CONHOH

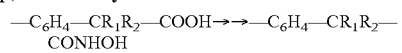

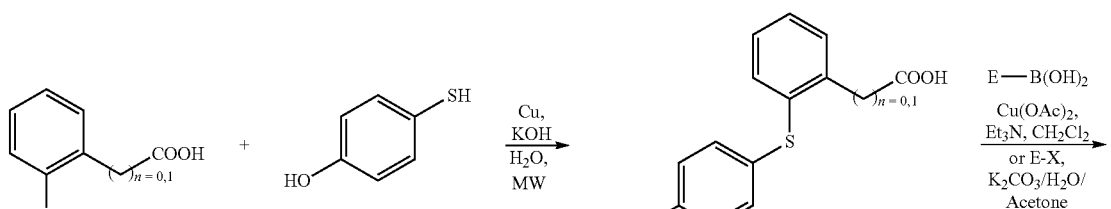

-continued

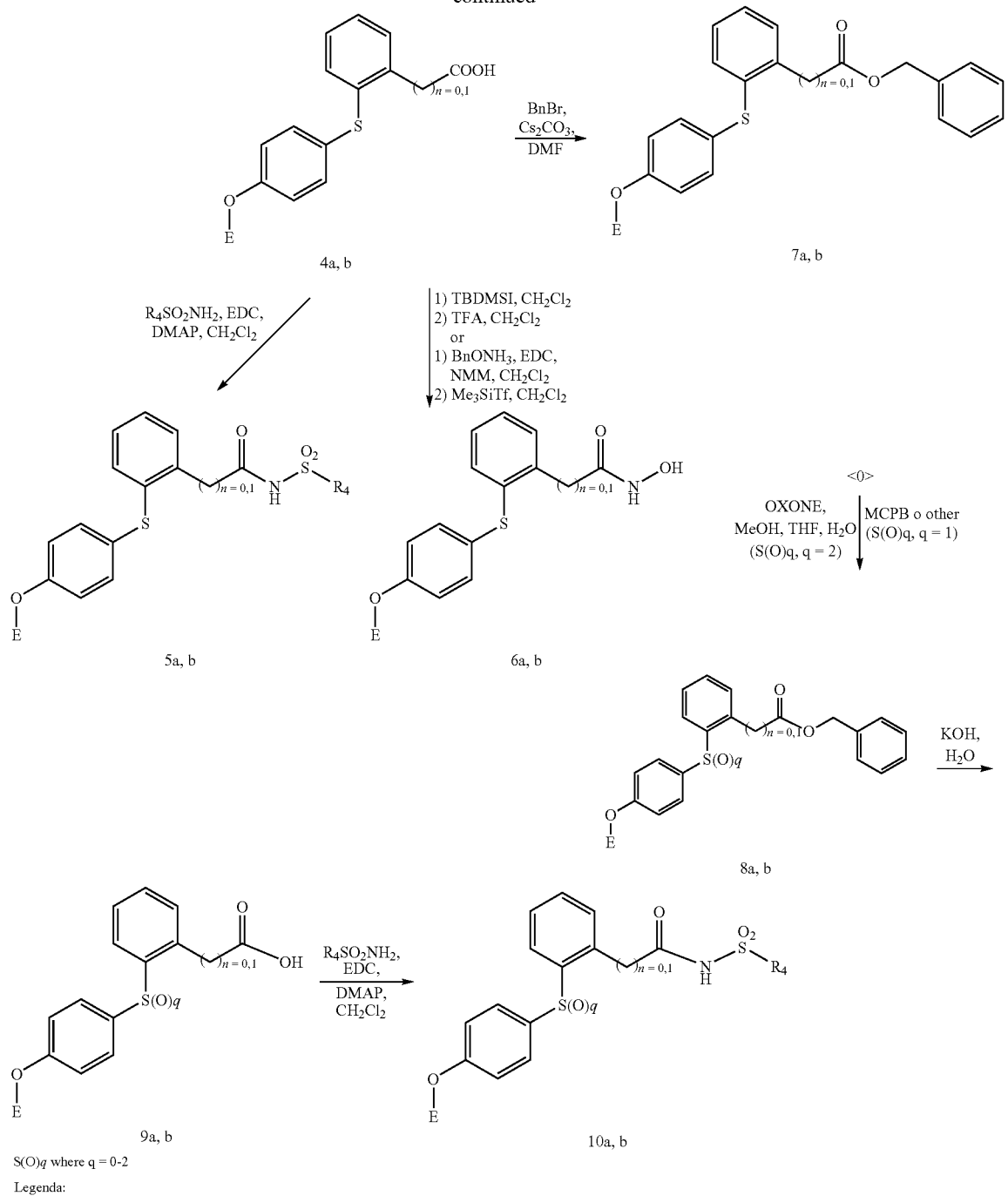

S(O)q where q = 0-2
Legenda:
a n = 0
b n = 1

As pointed out in the above Scheme 2, for the synthesis of benzoic derivatives (a), with n=0, and phenylacetic derivatives (b), with n=1, a synthetic pathway substantially analogous may apply.

The carboxylic derivatives 3a, 3b (with n as 0 or 1, respectively) are obtained using an "Ullman" type reaction, as per previous Scheme 1.

These latter derivatives may be converted into the corresponding compounds 4a and 4b, through reaction with appropriate substituted boronic acid derivatives [E-B(OH)$_2$] or with suitable E-halides (Br or Cl), wherein E has the meanings reported in formula (I). In case E represents an aryl or heteroaryl group it can be further substituted, by one or more groups as formerly indicated, in any free position.

Therefore, just as an example, E may represent a phenyl group optionally mono-, di- or tri-substituted in one or more of the ortho, meta or para positions.

The above reaction is well known in the art and may be carried out in the presence of suitable catalysts such as copper (II) acetate, in the presence of potassium carbonate and in acetone/water reflux.

The thus obtained compounds 4a, 4b may be then converted into a series of different products: the hydroxamic acids 6a, 6b, by working as per the aforementioned scheme 1; N-acylmethansulphonamides 5a, 5b, through coupling reactions with alkylsulphonamides [$R_4SO_2NH_2$]; and the corresponding benzyl ester derivatives 7a, 7b, through reaction with benzyl bromide and cesium carbonate.

In addition, the latter derivatives 7a, 7b may be then oxidized with Oxone® to the corresponding sulphonyl compounds 8a, 8b wherein, with respect to formula (I), q=2.

The compounds of formula 8a, 8b, in their turn, may be hydrolyzed to the derivatives 9a, 9b from which the corresponding N-acylsulphonamides 10a, 10b may be obtained. In another alternative way, the benzyl esters 7a, 7b may be oxidized into sulphoxides (q=1) by using, as oxidizing agent, m-chloroperoxybenzoic acid (MCPB) in dichloromethane or chloroform; sodium periodate ($NaIO_4$) under phase transfer conditions, for instance in the presence of a mixture of immiscible solvents such as water/chloroform or the like; sodium perborate ($NaBO_3$) or hydrogen peroxide in acetic acid; Titanium(III)-hydrogen peroxide in methanol; or the like.

The oxidation may also be favoured by the use of microwave, as per known methods in the art.

In addition, enantioselective oxidation may also occur so as to lead to the desired (R)- or (S)-sulphoxide, for instance with Ti(IV) isopropoxides such as Ti(O-iPr)$_4$/diethyltartrate and in the presence of proper chiral auxiliaries under Kagan reaction conditions [see, as a reference, Kagan, H et al, *J Org Chem* 1995, 60, 8086; and Renaud, P, *Tetrahedron Asymm.* 1999, 1051].

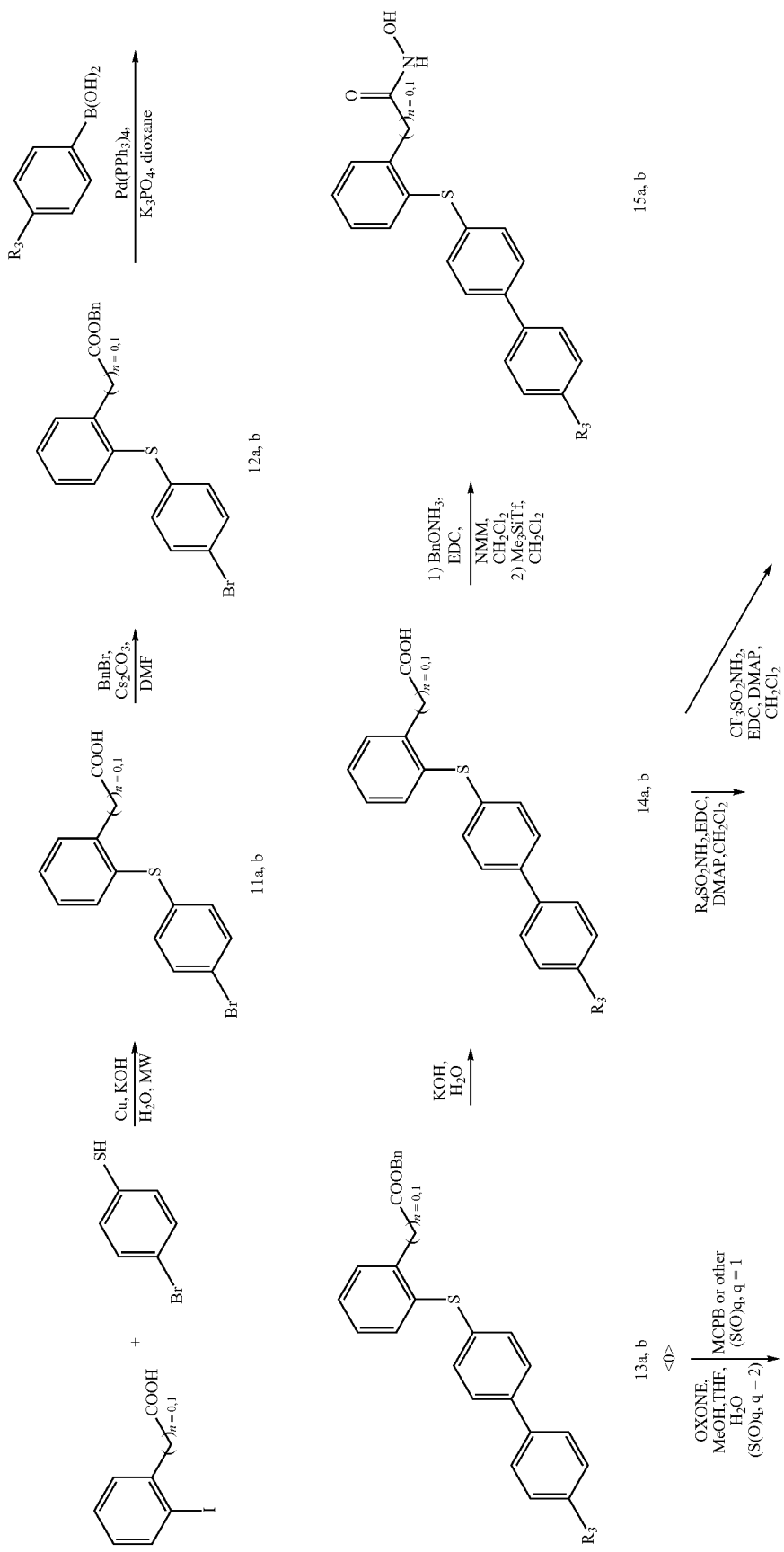
Scheme 3

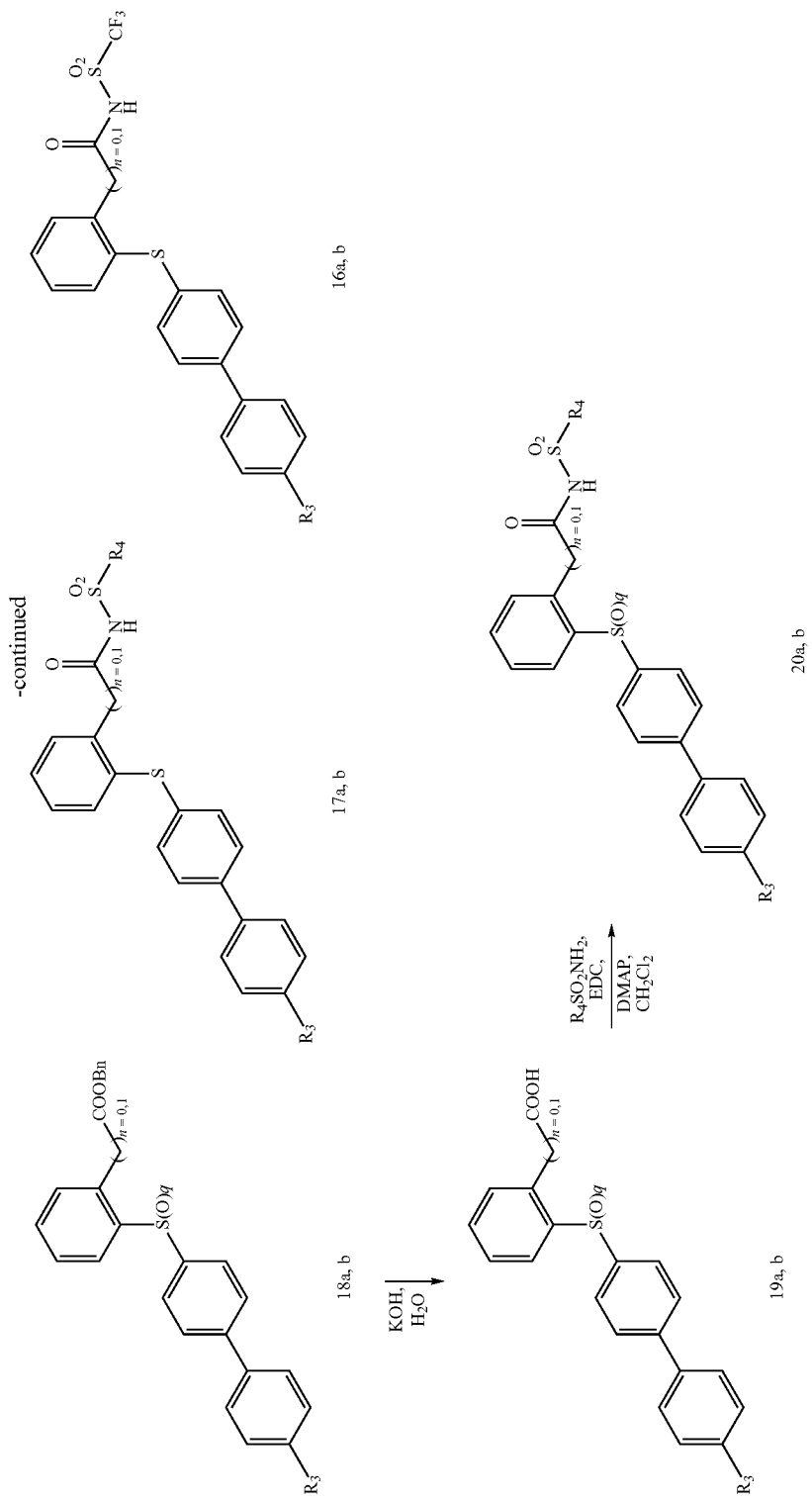

In the above scheme 3 there are described the synthetic pathways for the preparation of compounds, analogous to those reported in Scheme 2, but bearing a biphenyl moiety, that is to say those compounds of formula (I) wherein m=0 and E represents an optionally substituted phenyl group.

The benzoic and phenylacetic compounds 11a, 11b, [as before, "a" and "b" stand for compounds wherein, with respect to formula (I), n=0 or n=1, respectively], may be obtained as per the former scheme 1.

In their turn they may be converted into the corresponding benzyl esters 12a, 12b as per scheme 2. These latter may be subsequently used as substrates in a Suzuki reaction so as to obtain biphenyl derivatives 13a, 13b.

The reaction is carried out according to known methods by using Tetrakis(triphenylphosphine) Palladium as a catalyst, in the presence of potassium phosphate.

The thus obtained benzyl esters 13a, 13b may be then hydrolized to the corresponding carboxylic acids 14a, 14b, which can be further converted into the corresponding hydroxamates 15a, 15b, for instance through coupling reaction with O-benzylhydroxylamine and subsequent deprotection with trimethylsilyl triflate.

Compounds 14a, 14b may be also converted to the corresponding N-acylmethansulphonamides 17a, 17b or N-acyl trifluoromethanesulphonamides 16a, 16b, according to previously disclosed methods.

As formerly reported in scheme 2, benzyl esters 13a, 13b may be also oxidized to the corresponding sulphoxides or sulphones 18a, 18b (wherein, with respect to formula (I), q is 1 or 2, respectively).

Hydrolysis of the benzyl esters 18a, 18b to the compounds 19a, 19b and their subsequent coupling with alkylsulphonamides, allow to obtain the desired compounds 20a, 20b.

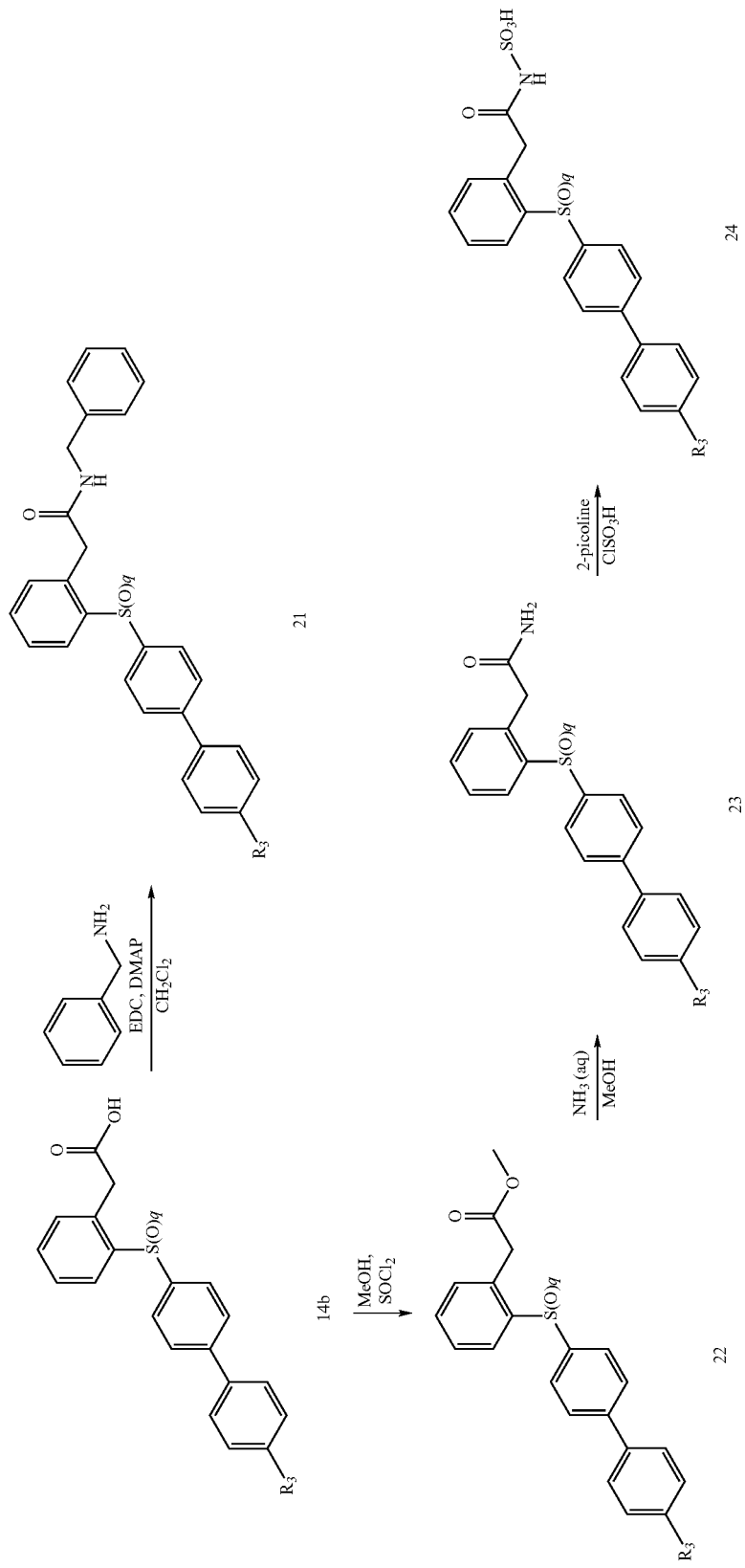

The carboxylic acids of type 14b [hence, with respect to formula (I), having n=1] as prepared per scheme 3, may be also used for both the synthesis of benzamides derivatives 21, by coupling reaction with benzylamine, and of N-acylsulphamic acid derivatives 24.

These latter are obtained through formation of the amides 23 and their conversion into 24 through reaction with chlorosulphonic acid and 2-picoline.

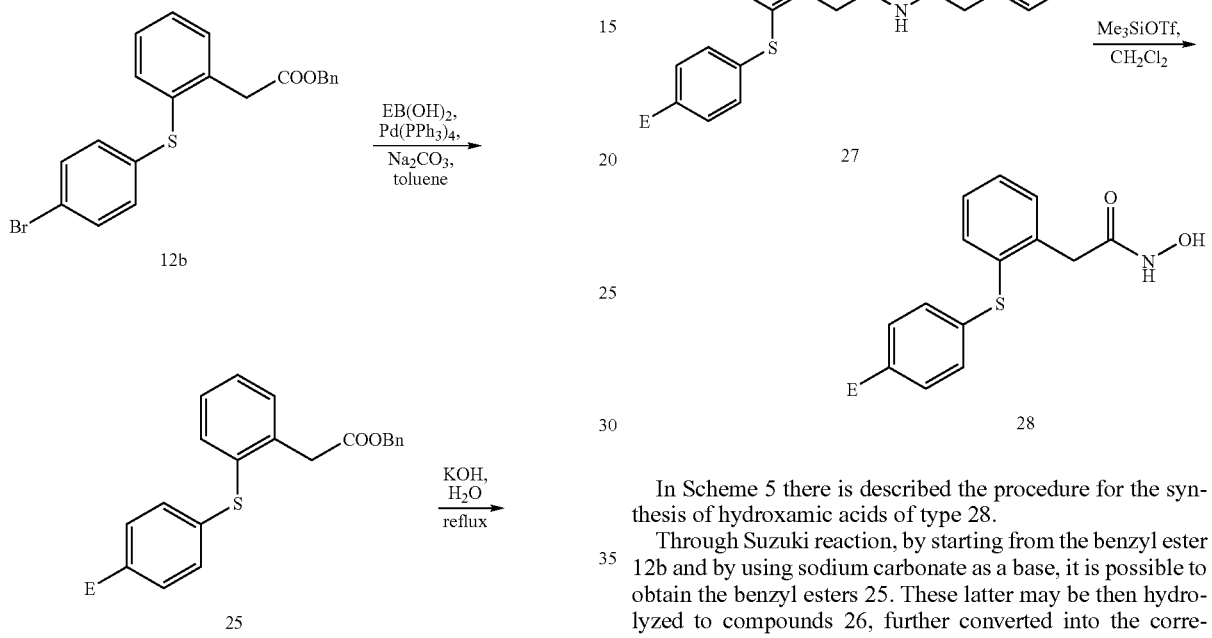

In Scheme 5 there is described the procedure for the synthesis of hydroxamic acids of type 28.

Through Suzuki reaction, by starting from the benzyl ester 12b and by using sodium carbonate as a base, it is possible to obtain the benzyl esters 25. These latter may be then hydrolyzed to compounds 26, further converted into the corresponding hydroxamic acids 28, by working as formerly reported.

Scheme 6
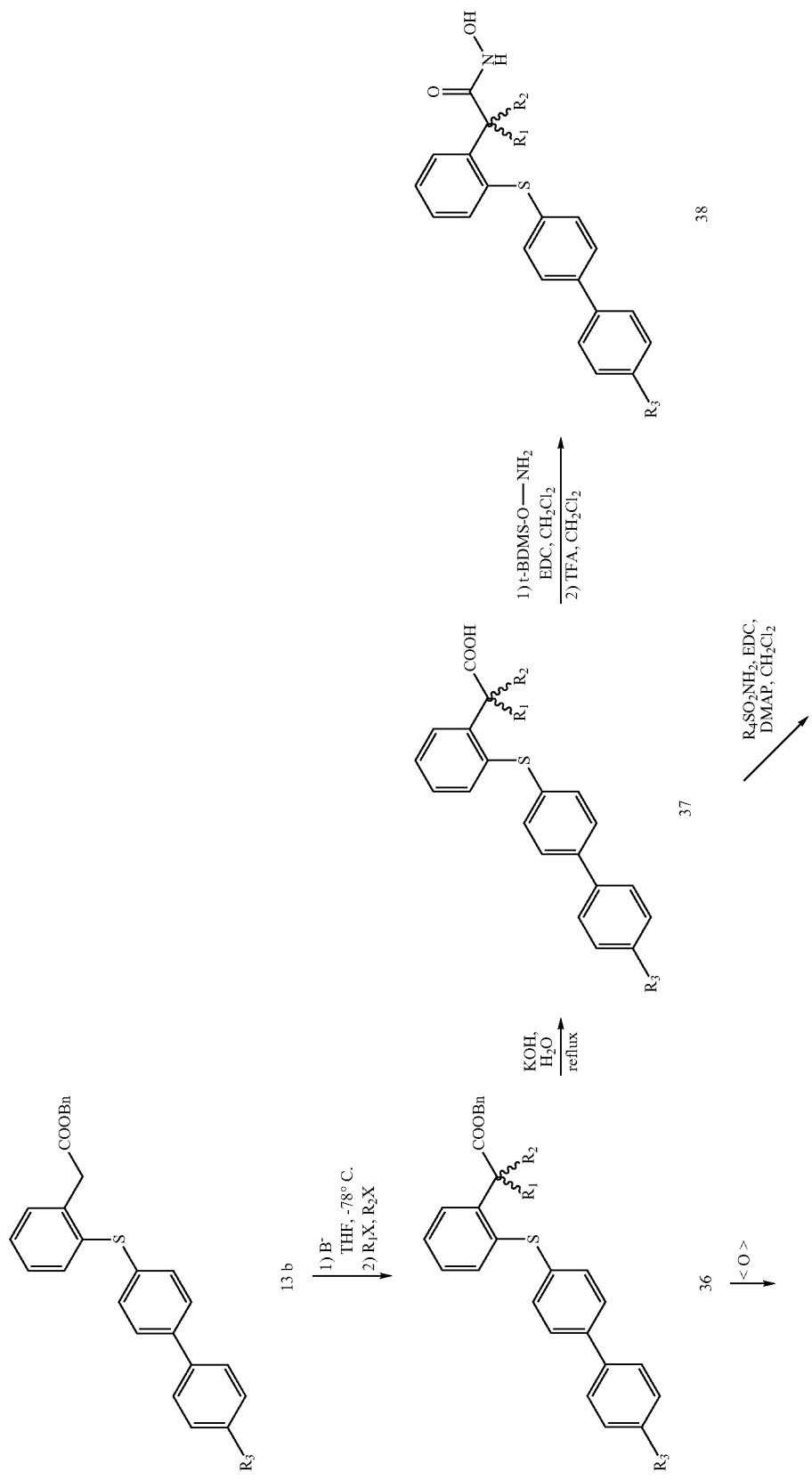

-continued
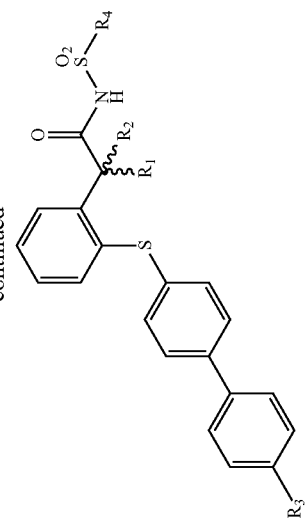
40
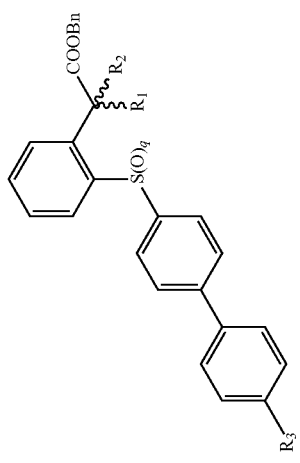
43
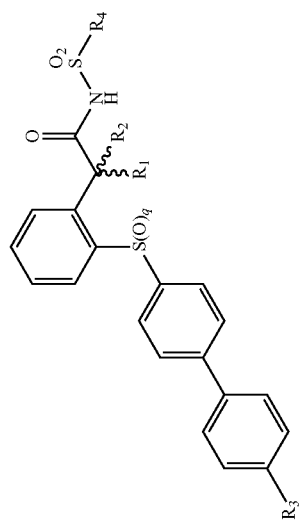
39
$\xrightarrow{\text{KOH, H}_2\text{O}}$ reflux
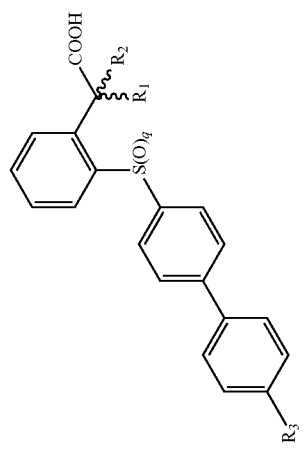
42
$\xrightarrow{\text{R}_4\text{SO}_2\text{NH}_2,\\ \text{EDC,}\\ \text{DMAP,}\\ \text{CH}_2\text{Cl}_2}$ As per the above scheme 6, there is represented the possible synthesis of derivatives of formula (I) wherein n=1 and $R_1$ and $R_2$ are alkyl or spirocycloalkyl groups, either having ZBG as corresponding to hydroxamate 38 or to N-acylsulphonamide derivatives 40 and 43.

The synthesis of these derivatives is presently exemplified by means of methyl substituted derivatives.

As such, the benzyl ester 13b is first methylated to 36 through the initial formation of the benzyl carbanion with n-BuLi, as per known methods, followed by reaction with a suitable methylating agent, for instance methyl iodide.

The benzyl carbanion may be obtained according to known methods, in the presence of suitable bases like n-BuLi, lithiumdiisopropylamide (LDA), lithiumhexamethyldisilylamide (LHMDS), sodium hexamethyldisilylamide (NaHMDS) or with other appropriate bases ($B^-$).

The carbanion thus obtained is then reacted with any suitable alkylating agent, for instance including alkyl or dialkyl halides $R_1$Alo or $R_2$Alo, also in the presence of suitable chiral auxiliaries enabling the preparation of pure enantiomers, from the optical point of view [see, as an example: Fadel, A Syn. Lett., 1992, 48; Evans, D. A., et al, J. Am. Chem. Soc, 1981, 103, 2127].

This same method is also applicable to the structures pointed out in Scheme 2.

Such a pathway, in addition, also provides for the synthesis of spirocyclic aliphatic or heterocyclic systems [see, as a reference, US 2003/0191317; and Venkatesan A. M., et al, J. Med. Chem., 2004, 47, 6255].

Once obtained, the resultant ester 36 may be then hydrolyzed to the carboxylic acid 37, which may be further used as a common intermediate for the preparation of hydroxamates 38 or N-acylsulphonamides 40.

The sulphonic derivative 43, instead, may be obtained starting from the benzyl ester 36, which is oxidized as formerly reported to sulphoxide or sulphone derivatives 39.

Hydrolysis of 39 allows to obtain the carboxylic acids 42, then converted into the sulphonic derivatives 43, as formerly reported.

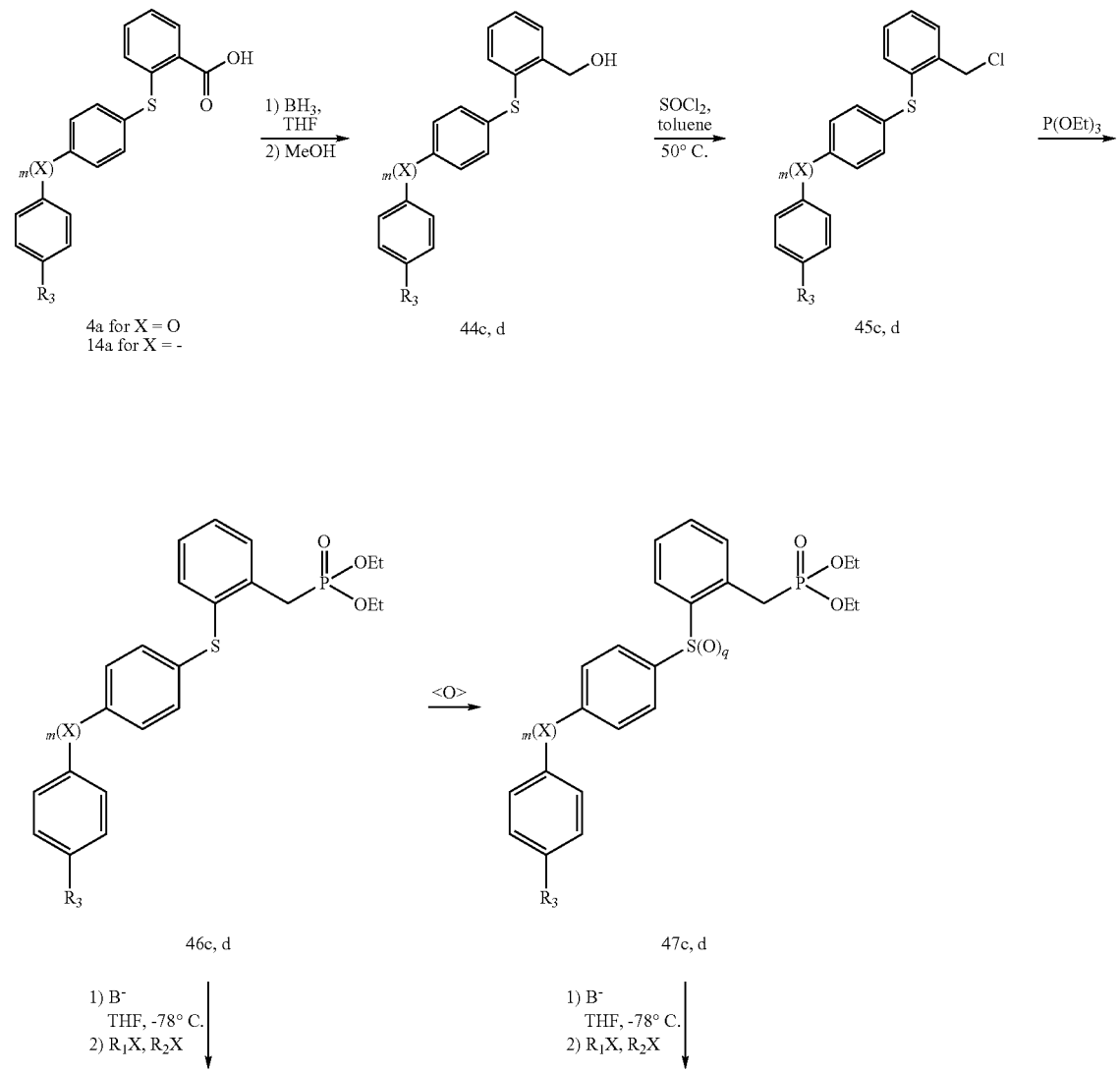

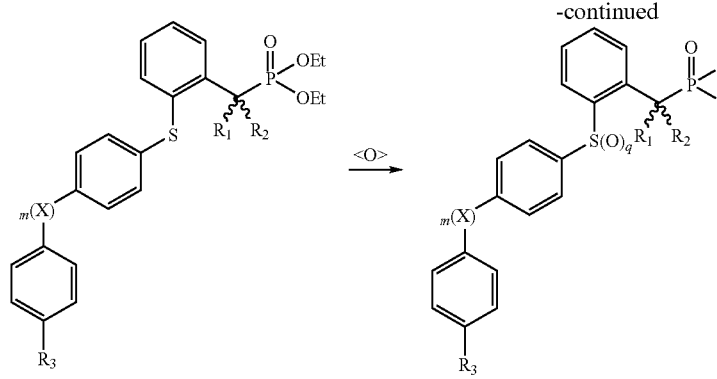

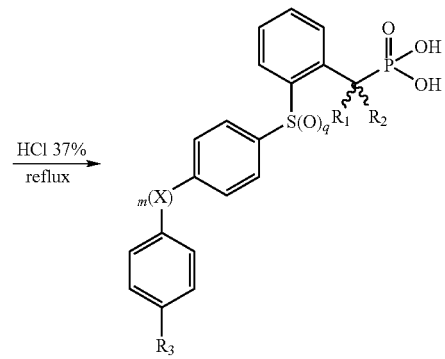

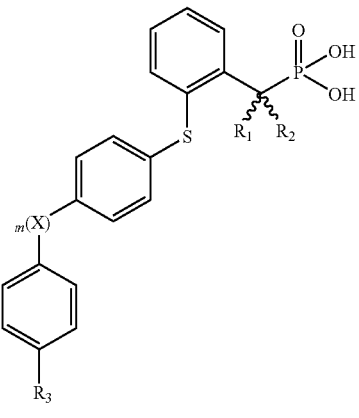

In the above scheme 7 there is described the synthetic pathway used to obtain phosphonic derivatives both of etheral (c compounds) and biphenylc (d compounds) structure. In order to obtain these derivatives, the carboxylic acids 4a [etheral compounds wherein, with respect to formula (I), m is 1 and X is oxygen] and 14a [biphenyl compounds wherein, with respect to formula (I), m is 0] may be reduced to the corresponding alcohols 44c, 44d, for instance in the presence of borane in THF or by means of other suitable reducing agents.

These latter may be then converted into chloride derivatives 45c, 45d, through treatment with thionyl chloride in toluene, subsequently reacted with triethylphosphite in order to obtain the phosphonic esters 46c, 46d.

Then, by properly selecting oxidative conditions, sulphoxides or sulphones 47c, 47d may be obtained, as per the previous pathways, subsequently alkylated to compounds 50c, 50d.

Alternatively, 46c, 46d may be first alkylated to compounds 49c, 49d, further oxidized to compounds 50c, 50d.

Alkylation of the selected compounds may be carried out through carbanion formation, as formerly reported in scheme 6 and, also, according to alternative known methods [see, as a reference, Bennani, Y L et al, Tetrahedron, 1996, 52, 13837-13866; Denmark, S. E. et al, *J. Am. Chem. Soc.*, 1995, 117, 11879-11897; or Goulioukina, N S et al *Tetrahedron Asymmetry*, 12, 319-237].

Hydrolysis of 50c, 50d, for instance in the presence of hydrochloric acid, allows to obtain the corresponding phosphonic acid derivatives 48c, 48d.

Clearly, corresponding phosphonic acid derivatives 51c, 51d wherein, with respect to formula (I), q=0, may be obtained through the direct hydrolysis of 49c, 49d.

The starting materials for the preparation of the compounds of formula (I) of the invention, for instance as per the above schemes and variants thereof, are all known or may be prepared according to known methods.

Finally, optional salification of the compounds of formula (I) may be carried out by properly converting any of the free acidic groups (e.g. carboxylic, sulphonic, phosphonic and the like) or free amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above processes, comprehensive of any variant thereof for the preparation of suitable compounds of formula (I) of the invention, may be conveniently modified so as to adapt the reaction conditions to the specific needs, for instance by choosing appropriate condensing agents, solvents and protective groups, as the case may be.

As such, within any suitable starting material or intermediate thereof, any given residue or group may be present as such or, alternatively, may be present in any properly protected form, as the case may be.

More in particular, functional groups being present in any of the starting materials and/or suitable intermediates and which could give rise to unwanted side reactions and byproducts, need to be properly protected before the desired reaction takes place. Likewise, subsequent deprotection of those same protected groups may follow upon completion of the said reactions.

In the present invention, unless otherwise indicated, the term "protecting group", designates a group adapted to preserving the function of the group to which it is bound. Specifically, protective groups are used to preserve amino, hydroxyl or carboxyl functions. Appropriate protective groups may thus include, for example, benzyl, benzyloxycarbonyl, alkyl or benzyl esters, or other substituents commonly used for the protection of such functions, which are all well known to those skilled in the art [see, for a general reference, T. W. Green; Protective Groups in Organic Synthesis (Wiley, N.Y. 1981)].

Likewise, selective protection and deprotection of any of the said groups, for instance including carboxyl, hydroxyl and amino groups, may all be accomplished according to very well known methods commonly employed in organic synthetic chemistry.

Selectivity of the Compounds of the Invention

According to the present invention, the compounds of formula (I) or the pharmaceutically acceptable salts thereof, are endowed with inhibitory activity against matrix metalloproteases and are therefore useful, in therapy, in the treatment of pathologies in which the regulation of said enzymes is altered.

As it will be demonstrated in the section concerning the biological results, the compounds of formula (I) of the invention, and the salts thereof, are endowed with inhibitory activity over selected proteases.

More in particular, some of the compounds of the invention are, advantageously, scarcely active towards MMP1 and/or MMP3 and/or MMP8 and/or MMP14.

These same compounds, on the contrary, are particularly active as inhibitors of MMP2, MMP9, MMP13 or ADAM17, ADAMTs1 and ADAMTs4.

In another advantageous embodiment of the invention, some of the compounds of the invention resulted as particularly selective in inhibiting MMP2 whilst practically lacking inhibitory activity towards MMPI, MMP3, MMP8, MMP9, MMP13, MMP14, TACE and ADAMTs1 and ADAMTs4.

In this respect, when assessing the inhibitory activity of the compounds of the invention over MMP2 and/or MMP9 and/or MMP13 and/or ADAM17 or ADAMTs1 and/or ADAMTs4, the corresponding $IC_{50}$ values, expressed in terms of nM or μM, are of at least one magnitude order lower than those measured over MMP1 and/or MMP14.

The $IC_{50}$ values of the compounds of the invention, or of the salts thereof, is determined through an in vitro method, as described in the subsequent experimental section. Alternatively, known techniques to assess the inhibitory activity towards given enzymes may be applied as well such as, for instance, those described in the literature [see, as an example inhibitory activity assessment towards MMPs: Rossello A. et al., Bioorg. & Med. Chem., 2004, 12, 2411; Rossello A. et al., Bioorg. & Med. Chem. Lett. 2005, 15, 1327; Rossello A. et al., Bioorg. & Med. Chem. Lett. 2005, 15, 2311; Rossello A. et al, Bioorg. & Med. Chem., 2006, 14, 4260; or as an example of inhibitory activity towards TACE and other ADAMs: Jin, G. et al Anal Biochemistry 2002, 269; Amour, A et al Febs Lett., 2000, 275; English, W R et al, J. Biol. Chem. 2000, 14046; Fourie, A M et al J. Biol. Chem. 2003, 30469; or as an example of inhibitory activity towards various other ADAMTs: Rodriguez-Manzaneque, J C et al, Biochem. Biophys. Res. Commun., 2002, 501; Anderson, P J et al, J. Biol. Chem. 2006, 850; Kokame, K et al, Br. J. Haem., 2005, 93; Miller J A et al, Anal. Biochem., 2003, 260; Noe, M C et al, Bioorg. & Med. Chem. Lett., 2005, 2808; US 2006/0014233].

Target Pathologies of the Compounds of the Invention and their Salts

As formerly reported, the invention also refers to the compounds of the invention of formula (I), or to the pharmaceutically acceptable salts thereof, for use as medicaments.

According to an additional embodiment it is also comprised within the scope of the present invention the use of the compounds of formula (I), or of the pharmaceutically acceptable salts thereof, in the preparation of a medicament useful for the treatment of pathological conditions associated with the abnormal activity of zinc metalloproteinases in mammals (as an example a human being or a pet, a farming, a lab, zoo or wild animal).

Pathological conditions may thus comprise, for instance, those conditions which are characterized by tissue disruption, fibrotic disease, pathological degradation of the matrix, bad repair of injuries, cardiovascular diseases or even diseases of the pulmonary, renal, hepatic, ophthalmic or of the central nervous system. Specific examples of the said conditions may comprise osteoarthritis, rheumatoid arthritis, septic arthritis, tumour invasion, tumour metastasis, tumour angiogenesis, decubitus ulcers, gastric ulcer, corneal ulcer, ocular angiogenesis, macular degradation, corneal cicatrization, periodontal disease, scleritis, AIDS, sepsis and septic shock, hepatic cirrhosis, diabetes, pulmonary fibrosis, otosclerosis, atherosclerosis (also including the phenomena of plaque destabilization leading to its breakage), multiple sclerosis, epidermic ulcerations, lack in injury repair, adhesion phenomena, cicatrization of injuries, cardiac decompensation, dilated cardiomyopathy, in post-stroke, in coronary thrombosis, in aortic and cerebral aneurism, in restenosis, osteoporosis, in chronic coronary obstructive disease, in emphysema, in the pathologies of rejection of transplanted organs, in asthma allergic reaction, in proteinuria, in pathologies of the bone, in the Alzheimer's disease and in the central nervous system diseases associated with nitrosative and oxidative stresses (as an example including: ictus, cerebral ischemia, cranial trauma, spinal cord injury and other acute or chronic neurodegenerative pathologies), autoimmune disorders, Huntington's disease, Parkinson's disease, migraine, depression, peripheral neuropathy, pain, cerebral amyloid angiopathy, nootrope or cognitive enhancement, amyotrophic lateral sclerosis, multiple sclerosis, and the like.

According to an additional embodiment, therefore, the present invention provides a compound of formula (I) for use as a therapeutic agent.

Additionally, also comprised within the scope of the invention is the use of a compound of formula (I) in the preparation of a medicament for the treatment of degenerative disorders, in particular of tumours.

In a still another embodiment, the invention concerns pharmaceutical compositions comprising, as an active ingredient, a pharmaceutically effective amount of a compound of formula (I), including pharmaceutically acceptable salts thereof, in combination with one or more pharmaceutically acceptable carriers or excipients.

In a yet another aspect, the invention provides a method for the treatment of degenerative disorders comprising the administration, to a mammal in need thereof, of a therapeutically effective amount of a compound of formula (I).

From all of the above, it can be easily envisaged that the compounds of this invention may have a wide range of applications, in therapy, and may be thus properly formulated according to conventional methods for the intended administration route: i.e. topical, oral and parenteral administration.

Furthermore, because of their selectivity towards given proteases, the compounds of the invention can be properly functionalized, for instance through conjugation with any suitable therapeutic or diagnostic agent, as per known methods.

In this respect, once the above conjugated are so administered, the compounds of formula (I) of the invention may thus serve as valuable carriers so as to bring the above therapeutic or diagnostic moieties to given tissues/districts of the body which over-expression of the selected protease may occur.

With the aim of better illustrate the present invention, without posing any limitation to it, the following examples are now given. In this respect, further applications including possible variants to the preparative process, that will become evident to the skilled person, are thus to be considered as comprised within the scope of the present invention.

EXAMPLE 1

2-(4-methoxyphenylthio)benzoic acid (1) and N-hydroxy-2-(4-methoxyphenylthio) benzamide (2)

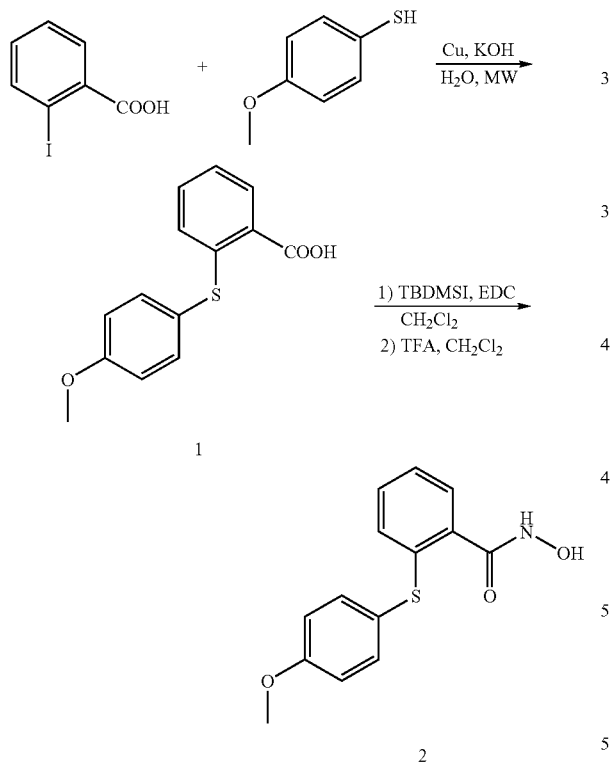

(1) A suspension of o-iodo benzoic acid (1 g, 4.03 mmol), 4-methoxythiophenol (565 mg, 4.03 mmol), KOH (451 mg, 8.1 mmol) and copper powder (25.6 mg, 0.403 mmol) in deionized water (2 mL), undertook two cycles of microwaves of 6 min each at the power of 180 Watt (Tmax=100° C., Pmax=100 psi), cooling the sample during the radiation with a flow of compressed air. The obtained suspension was dissolved in an aqueous solution of KOH 2N and filtered. The filtrate was acidified with HCl 1N and the formed precipitate filtrated and dried under reduced pressure (T=50° C.). The obtained solid was purified through trituration with acetone obtaining the product 1 (850 mg, 81%, white solid).

$H^1$-NMR ($d^6$-DMSO 200 MHz): δ 3.82 (s, 3H), 6.63 (d, 1H), 7.06-7.20 (m, 3H), 7.30-7.40 (m, 1H), 7.45-7.49 (d, 2H), 7.91 (dd, 1H).

(2) To a solution of the carboxilic acid 1 (100 mg, 0.38 mmol) and O-tert-butyldimethylsilyl hydroxylamine (TBDMSI, 56 mg, 0.38 mmol) in $CH_2Cl_2$ anhydrous (3 mL) put in inert atmosphere, there was added EDC (72.2 mg, 0.38 mmol). The reaction was stirred overnight at room temperature. The solution was thus diluted with $CH_2Cl_2$ and washed with $H_2O$ and HCl 1N. The organic phase was dried with $Na_2SO_4$ and evaporated under reduced pressure.

The obtained crude product (72 mg) was deprotected without further purification through reaction with TFA (0.79 μg, 57 equivalents) in $CH_2Cl_2$ anhydrous (7.5 mL) for 24 h at room temperature. The solvent and the excess of TFA were thus evaporated under reduced pressure and the obtained crude product was purified through trituration with $CHCl_3$ and n-hexane. There was obtained 18 mg of 2 (17%, white solid).

$H^1$-NMR ($d^6$-DMSO 200 MHz): δ 3.79 (s, 3H), 6.78 (d, 1H), 7.00-7.44 (m, 7H), 9.20 (br s, 1H), 11.02 (s, 1H).

EXAMPLE 2

2-(4-(4-methoxyphenoxy)phenylthio)benzoic acid (4) and N-hydroxy-2-(4-(4-methoxyphenoxy)phenylthio)benzamide (5)

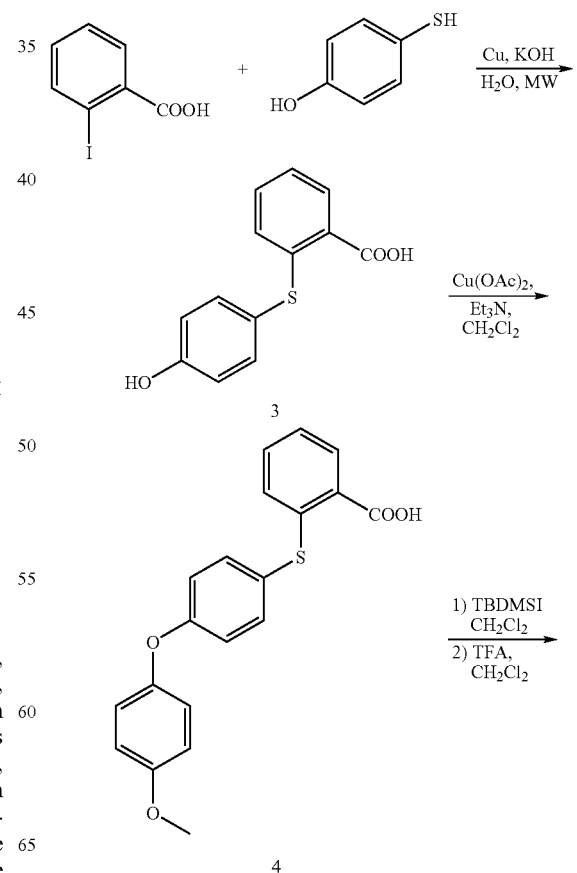

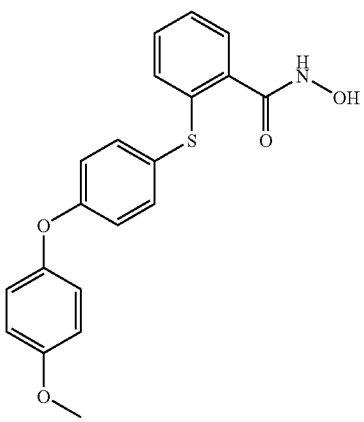

5

(3) Compound 3 was synthesized following an analogous procedure to that described for the preparation of 1, starting from 2-iodobenzoic acid (1.5 g, 6.05 mmol) and 4-mercaptophenol (763 mg, 6.05 mmol). The purification was carried out through trituration with acetone thus obtaining the product 3 (1.11 g, 75%, white solid).

$^1$H-NMR (d$_6$-DMSO 200 MHz): δ 6.65 (d, 1H), 6.68 (d, 2H), 7.09-7.20 (m, 1H), 7.29-7.40 (m, 3H), 7.90 (d, 1H), 9.98 (br. s, 1H).

(4) To a suspension of 3 (400 mg, 1.63 mmol), p-methoxyphenylboronic acid (494 mg, 3.26 mmol), Cu(OAc)$_2$ (324 mg, 1.63 mmol) and 4 Å molecular sieves in powder (650 mg) in anhydrous CH$_2$Cl$_2$ (16 mL), was added triethylamine (5 equivalents). The suspension was stirred overnight at room temperature, after that it was filtered and the filtrated was treated with HCl 1N. The product was extracted with CH$_2$Cl$_2$. The organic phases were dried with Na$_2$SO$_4$ and evaporated under reduced pressure. The obtained crude was purified by inverse phase flash chromatography (Eluent: MeOH:H$_2$O 3:7). There were obtained 190 mg of 4 (33%, brown solid).

$^1$H-NMR (d$_6$-DMSO, 200 MHz): δ 3.76 (s, 3H), 6.69 (dd, 1H), 6.98-7.20 (m, 7H), 7.32-7.52 (m, 3H), 7.90 (d, 1H), 13.2 (br. s, 1H).

(5) Compound 5 was synthesized following an analogous procedure to that described for the preparation of 2, starting from compound 4 (130 mg, 0.37 mmol). The obtained product was purified by flash chromatography (ELUENT: CH$_2$Cl$_2$:MeOH 9:1); there were obtained 20 mg of 5 (15%, white solid).

$^1$H-NMR (d$_6$-DMSO, 200 MHz): 0.3.76 (s, 3H), 6.85-7.23 (m, 6H), 7.28-7.52 (m, 6H), 9.20 (br s, 1H), 11.03 (s, 1H).

EXAMPLE 3

2-(4-(4-methoxyphenoxy)phenylsulphinyl)benzoic acid (6) and N-hydroxy-2-(4-(4-methoxyphenoxy)phenylsulphinyl)benzamide (7)

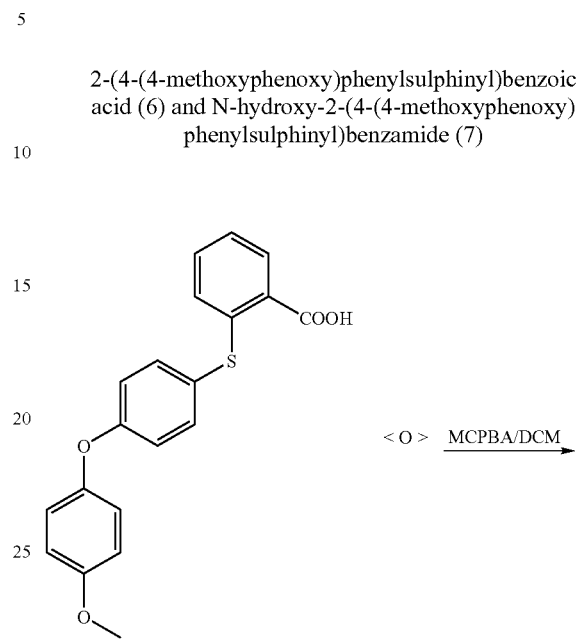

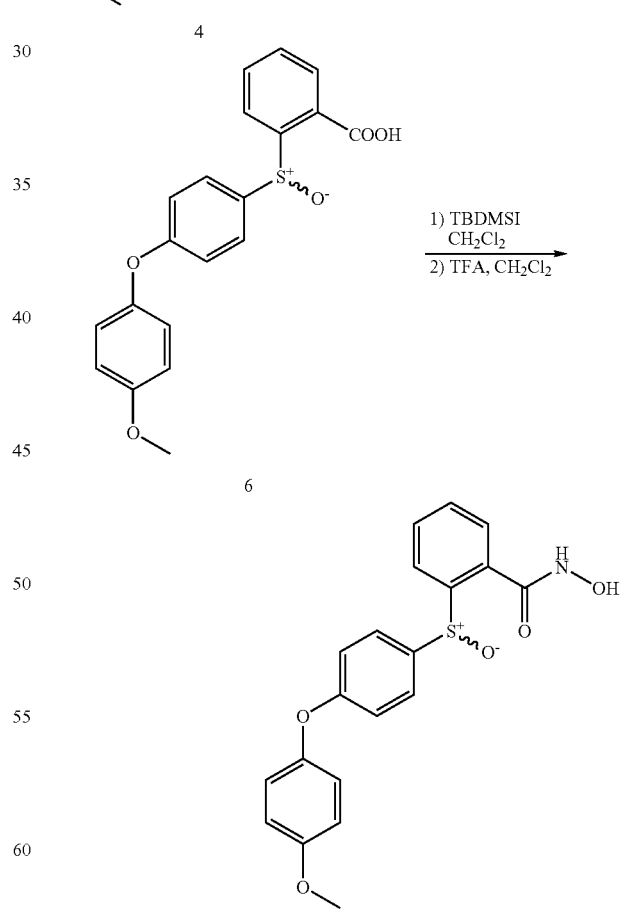

(6) A solution of the acid 4 (1 mmol) in anhydrous DCM (50 mL) was added during a period of 1 hour with metachloroperoxybenzoic acid (1.5 mmol). The reaction mixture was left stirring at room temperature for 24 hours, filtered and evaporated to dryness. The residue, taken with ethyl acetate, was washed with a saturated solution of NaHCO$_3$ (2×20 mL), with water, filtered and evaporated at r.p. to yield a yellow oil essentially constituted of a (R,S)-6 mixture of practically pure sulphoxides.

H$^1$-NMR (d$^6$-DMSO, 200 MHz): δ 3.72 (s, 3H), 6.80-7.07 (m, 6H), 7.20-8.01 (m, 6H), 12.8 (br. s, 1H). The mixture of the two sulphoxides was used as such for the following step.

(7) The hydroxamate (R,S)-7 was synthesized following an analogous procedure to that described in 2, starting from compound 6. The obtained product was purified by flash chromatography (ELUENT: CH$_2$Cl$_2$:MeOH 12:1); there were obtained 12 mg of 7 (20%, white solid).

$^1$H-NMR (d$^6$-DMSO, 200 MHz): δ 3.73 (s, 3H), 6.81-7.04 (m, 6H), 7.21-8.11 (m, 6H), 11.03 (s, 1H).

EXAMPLE 4

2-(4-(4-methoxyphenoxy)phenylthio)-N-(methylsulphonyl)benzamide (8)

(8) To a solution of carboxilic acid 4 (100 mg, 0.28 mmol), of methanesulphonamide (34 mg, 0.37 mmol) and N,N-dimethyl-4-aminopyridine (DMAP) (45 mg, 0.37 mmol) in anhydrous CH$_2$Cl$_2$ (2.8 mL) under inert atmosphere, there was added EDC (70.7 mg, 0.37 mmol). The reaction was kept under stirring at room temperature for 4 hours. The solution was diluted with CH$_2$Cl$_2$ and washed three times with HCl 1N and brine. The organic phase was dried with Na$_2$SO$_4$ and evaporated under reduced pressure. The obtained crude was purified by trituration with diethyl ether giving 41.7 mg of 8 with a yield of 34%.

$^1$H-NMR (d$^6$-DMSO 200 MHz) δ 3.37 (s, 3H), 3.76 (s, 3H), 6.92-7.11 (m, 7H), 7.22-7.30 (m, 1H), 7.38-7.48 (m, 3H), 7.64 (m, 1H), 12.30 (br s, 1H).

EXAMPLE 5

2-(2-(4-(4-methoxyphenoxy)phenylthio)phenyl)acetic acid (11) and N-hydroxy(2-(2-(4-(4-methoxyphenoxy)phenylthio)phenyl)acetamide (13)

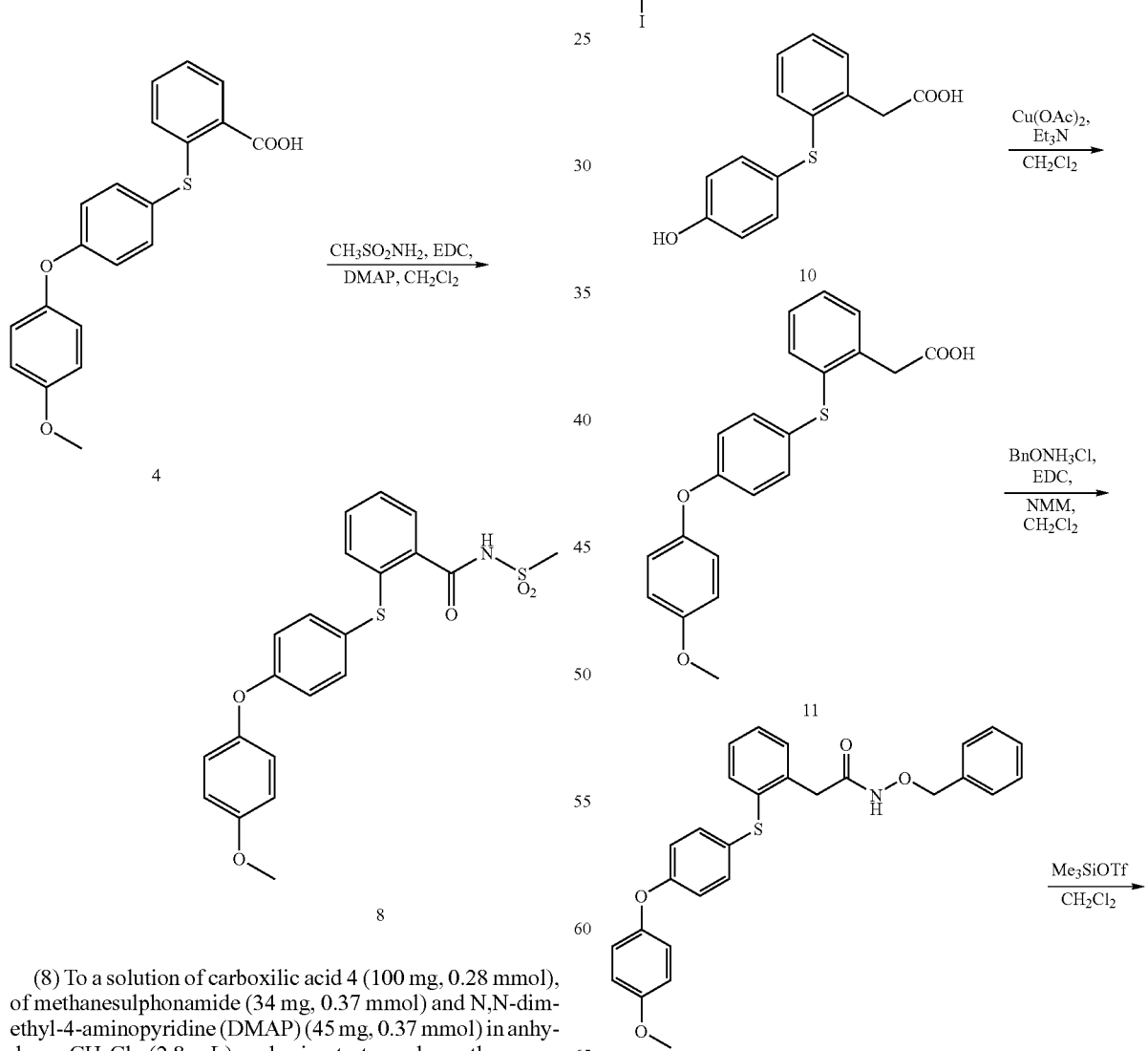

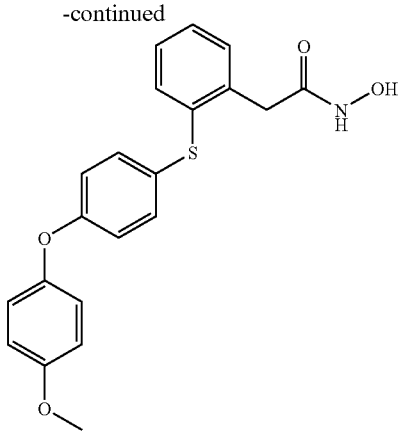

13

(10) Compound 10 was synthesized following an analogous procedure to that described for the preparation of 1, starting from o-iodophenylacetic acid (1 g, 3.82 mmol) and 4-mercaptophenol (482 mg, 3.82 mmol). The obtained crude product was purified by trituration with acetone obtaining 2.5 g of 10 (84%, white solid).

$^1$H-NMR (d$_6$-DMSO 200 MHz): δ 3.73 (s, 2H), 6.77-6.81 (m, 2H), 6.92-7.00 (m, 1H), 7.14-7.32 (m, 5H), 9.80 (s, 1H), 12.38 (s, 1H).

(11) Compound 11 was synthesized according to the procedure described for the preparation of 4, starting from compound 10 (1.9 g, 7.3 mmol) and 4-methoxyphenyl boronic acid (2.2 g, 7.3 mmol). The obtained product was purified by flash chromatography (ELUENT: CH$_2$Cl$_2$:Et$_2$O 9:1, CH$_2$Cl$_2$:Et$_2$O 8:2, CH$_2$Cl$_2$:MeOH 9:1) recovering 840 mg of 11 (yellow solid) with a yield of 31%.

$^1$H-NMR (d$_6$-DMSO 200 MHz): δ 3.75 (s, 5H), 6.88-7.06 (m, 6H), 7.12-7.36 (m, 6H), 12.34 (s, 1H).

(12) To a solution of carboxylic acid 11 (800 mg, 2.18 mmol) and EDC (460 mg, 2.40 mmol) in anhydrous CH$_2$Cl$_2$ (44 mL) under inert atmosphere, there was added a solution of O-benzyloxy hydroxylamine chlorhydrate (383 mg, 2.40 mmol) and NMM (264 μL, 2.40 mmol) in anhydrous CH$_2$Cl$_2$ (22 mL). The solution was left stirring at room temperature for 5 hours. The solution was then diluted with CH$_2$Cl$_2$ and washed respectively with HCl 1N, NaHCO$_3$ sat. sol., and NaCl sat. sol. The organic phase was dried with Na$_2$SO$_4$, and brought to dryness. The obtained product was purified by flash chromatography (ELUENT: n-Hexane:AcOEt 2:1). There were obtained 645 mg of 12 (62%, white solid).

$^1$H-NMR (CDCl$_3$, 200 MHz): δ 3.64 (s, 2H), 3.80 (s, 3H), 4.85 (s, 2H), 6.81-7.01 (m, 6H), 7.12-7.31 (m, 11H), 8.08 (br.s, 1H).

(13) A solution of compound 12 (100 mg, 0.212 mmol) and of trimethylsilyltriflate (384 μL, 2.12 mmol) in CH$_2$Cl$_2$ anhydrous (1 mL) under inert atmosphere, was kept under stirring for 36 hours. The solution was treated with H$_2$O and the product was extracted with CH$_2$Cl$_2$. The organic phase was dried with Na$_2$SO$_4$, and brought to dryness. The obtained compound was purified by trituration with diisopropyl ether obtaining 20 mg of 13 (25%, white solid).

$^1$H-NMR (d$_6$-DMSO, 200 MHz): 3.51 (s, 2H), 3.75 (s, 3H), 6.89-7.28 (m, 12H), 8.85 (br.s, 1H), 10.64 (s, 1H).

EXAMPLE 6

2-(2-biphenyl-4-ylthio)phenyl)acetic acid (19a), 2-(2-(4-methoxyphenylthio)phenyl)acetic acid (19b), 2-(2-biphenyl-4-ylthio)phenyl)-N-hydroxyacetamide (21a), N-hydroxy-2-(2-(4-methoxyphenylthio)phenyl)acetamide (21b) and 2-(2-(4-(but-2-iniloxy)phenylthio)phenyl)-N-hydroxyacetamide (21c)

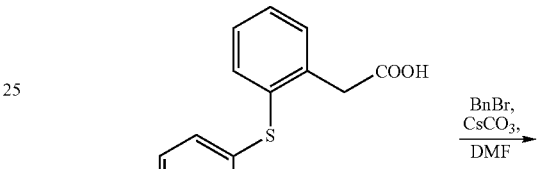

16

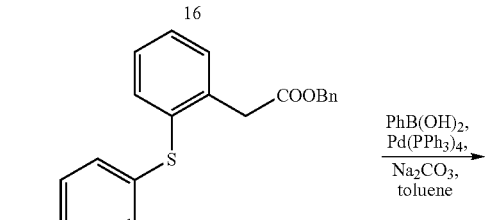

17

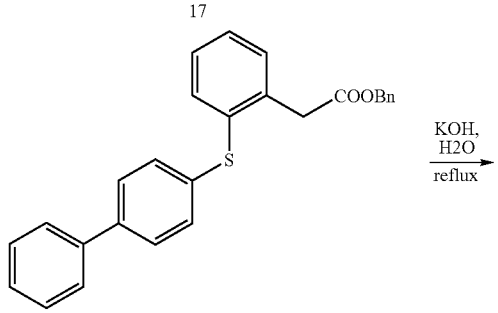

18

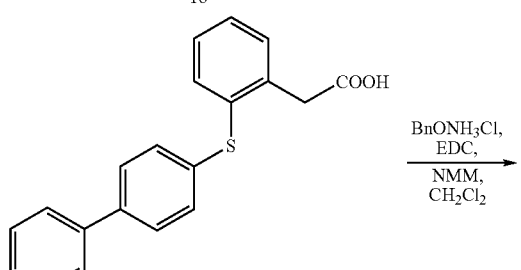

19a

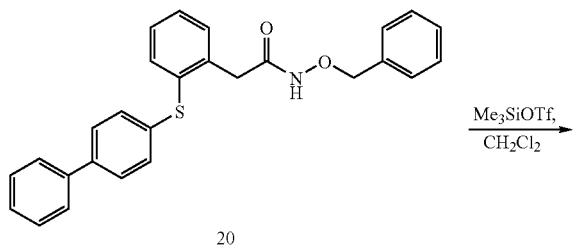

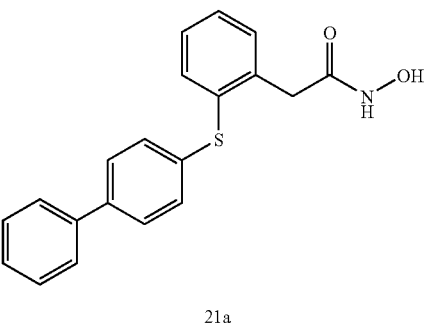

(16) Compound 16 was synthesized according to the procedure described for the preparation of 10, starting from o-iodophenylacetic acid (5 g, 19.08 mmol) and 4-bromobenzenethiol (2.4 g, 19.08 mmol) into 5 portions of 1 g each. The obtained suspension was collected and diluted in KOH 2N. The obtained suspension was filtered and acidified with HCl 1N. The formed precipitate was brought to dryness under reduced pressure at 50° C. There were recovered 4.37 g of 16 (88%, white solid).

$^1$H-NMR (d$_6$-DMSO, 200 MHz): 3.74 (s, 2H), 7.07 (d, J=8 Hz, 2H), 7.30-7.42 (m, 4H) 7.49 (d, J=8 Hz, 2H), 12.34 (br.s, 1H).

(17) To a solution of the carboxylic acid 16 (3.3 g, 10.21 mmol) in anhydrous DMF under anhydrous and cooled atmosphere at 0° C. it was added Cs$_2$CO$_3$ (3.326 g, 10.21 mmol). The suspension was maintained under stirring for 40 min, then benzyl bromide (1.2 mL, 10.21 mmol) was added and the suspension was maintained under stirring at 0° C. for 30 min and then at room temperature for 12 hours.

To the reaction mixture, H$_2$O was thus added and the product was extracted with ethyl ether. The organic phase was washed with H$_2$O and with a saturated solution of NaCl and then it was dried over Na$_2$SO$_4$, and brought to dryness. There were obtained 4.09 g of product 17 (97%, yellow oil) used in the following reaction without further purification.

$^1$H-NMR (CDCl$_3$, 200 MHz): 3.87 (s, 2H), 5.01 (s, 2H), 6.95-7.00 (m, 2H), 7.27-7.44 (m, 11H).

(18) To a solution of 17 (4.09 g, 9.9 mmol) in anhydrous toluene (21 mL) under inert atmosphere, Pd(PPh$_3$)$_4$ (171 mg, 0.148 mmol) was added and the solution was kept under stirring at room temperature for 10 minutes, then a solution of phenylboronic acid (1.45 g, 11.88 mmol) in anhydrous dioxane (8 mL) and a solution of Na$_2$CO$_3$ (2.15 g, 20.30 mmol) in H$_2$O (7.6 mL) were added. The solution was kept refluxing for 5 hours. Then, it was neutralized with HCl 1N and the product was extracted with EtOAc. The organic phase was washed with a saturated solution of NaCl, dried over Na$_2$SO$_4$ and brought to dryness. The obtained crude was purified by flash chromatography (Eluent: n-Hexane:CH$_2$Cl$_2$ 6:4) obtaining 2.95 g of 18 (72%, yellow oil).

$^1$H-NMR (CDCl$_3$, 200 MHz): 3.93 (s, 2H), 5.01 (s, 2H), 7.20-7.56 (m, 18H).

(19a) A suspension of 18 (500 mg, 1.13 mmol) and KOH (190 mg 3.39 mmol) in H$_2$O (3.4 mL) was kept refluxing for 18 hours. Then the reaction was left cooling and brought to acidic pH with HCl 1N. The product was extracted with CH$_2$Cl$_2$. The organic phase was dried over Na$_2$SO$_4$ and brought to dryness. The product was purified by trituration with Et$_2$O/n-Hexane. There were obtained 292 mg of 19a (88% white solid).

$^1$H-NMR (d$_6$-DMSO, 200 MHz): 3.95 (s, 2H), 7.43-7.62 (m, 8H), 7.86-7.98 (m, 4H), 8.10-8.17 (m, 1H), 12.39 (br s., 1H).

(19b) Analogously to the above preparation of compound 19a, and by using 4-methoxythiol in place of 4-bromobenzenthiol as per the preparation of the above 16, 2-(2-(4-methoxyphenylthio)phenyl)acetic acid 19b was prepared.

H$^1$-NMR (CDCl$_3$, 200 MHz): 3.78 (s, 3H), 3.87 (s, 2H), 6.82-6.86 (m, 2H), 7.16-7.30 (m, 6H).

(20) Compound 20 was synthesized according to the procedure described for the preparation of 12, starting from compound 19a (200 mg, 0.62 mmol). The obtained crude was purified by flash chromatography (Eluent n-Hexane:AcOEt 1:2) recovering 186 mg of 20 (67%, yellow solid).

H$^1$-NMR (CDCl$_3$, 200 MHz): 3.64 (s, 2H), 4.81 (s, 2H), 6.94-6.99 (m, 2H), 7.12-7.50 (m, 16H), 8.14 (br s, 1H).

(21a) Compound 21a was synthesized according to the procedure described for the preparation of 13, starting from 20 (180 mg, 0.41 mmol). The obtained product was purified by trituration with CH$_2$Cl$_2$ and diisopropyl ether. There were recovered 25 mg of 21a (17%, white solid).

H$^1$-NMR (d$^6$-DMSO, 200 MHz): 3.55 (s, 2H), 7.21-7.49 (m, 9H), 7.61-7.65 (m, 4H), 8.85 (s, 1H), 10.64 (s, 1H).

(21b) Analogously to what above reported for the preparation of 21a and by replacing 4-bromobenzenthiol with 4-methoxythiol, N-hydroxy-2-(2-(4-methoxyphenylthio) phenyl)acetamide 21b was prepared. (82%, white solid).

M.p.=84° C. H$^1$-NMR (d$^6$-DMSO, 200 MHz): 3.50 (s, 2H), 3.76 (s, 3H), 6.95-6.99 (m, 2H), 7.14-7.34 (m, 6H), 8.84 (s, 1H), 10.63 (s, 1H).

(21c) By working as described in the preparation of compound 16 and by using 4-(but-2-inyloxy)thiophenol rather than 4-bromothiophenol, the corresponding carboxylic acid was obtained, and further converted into the corresponding 2-(2-(4-(but-2-iniloxy)phenylthio)phenyl)-N-hydroxyacetamide 21c (35%, white solid). M.p.=105° C.

H$^1$-NMR (CDCl$_3$, 200 MHz): 1.86 (t, J=2.2 Hz, 3H), 3.69 (s, 2H), 4.63 (q, J=2.4 Hz, 2H), 6.91-6.95 (m, 2H), 7.12-7.29 (m, 6H).

EXAMPLE 7

2-(2-(4'-methoxybiphenyl-4-ylthio)phenyl)acetic acid (22) and N-hydroxy-2-(2-(4'-methoxybiphenyl-4-ylthio)phenyl)acetamide (24)

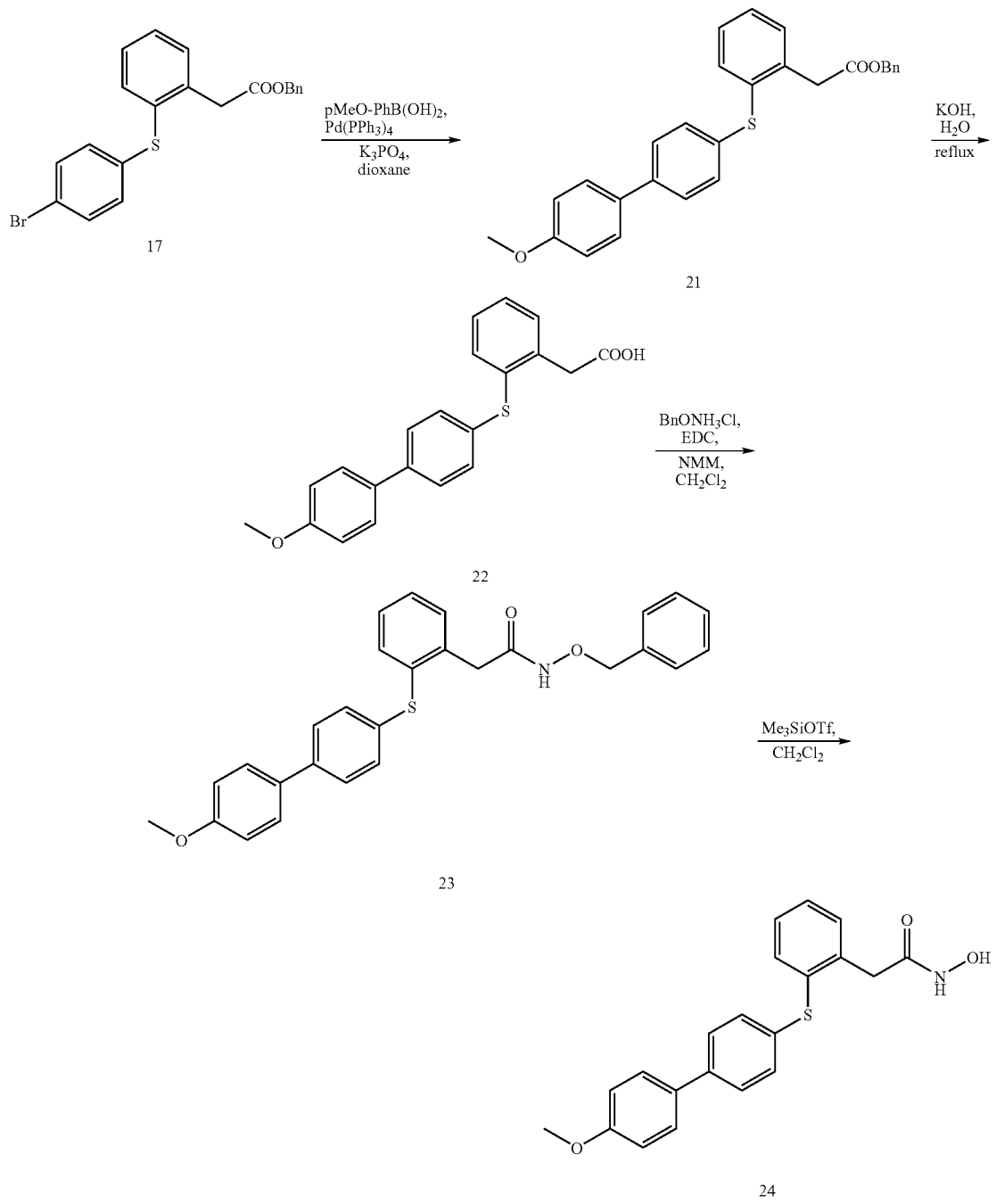

(21) A mixture of 17 (2.60 g, 6.29 mmol), $K_3PO_4$ (3.07 g, 14.47 mmol), p-methoxyphenylboronic acid (1.62 g, 10.7 mmol) and $Pd(PPh_3)_4$ (363 mg, 0.31 mmol) in anhydrous dioxane (63 mL)/$H_2O$ (10 mL) was kept at 85° C. for 2 hours. Then it was left cooling and treated with $NaHCO_3$ and the product was extracted with AcOEt. The organic phase was dried with $Na_2SO_4$, and brought to dryness. The product was purified by flash chromatography (Eluent: n-Hexane:AcOEt 9:1) and product 21 was recovered (1.9 g, 68%, yellow solid).

$^1$H-NMR (CDCl$_3$, 200 MHz): 3.85 (s, 3H), 3.93 (s, 2H), 5.10 (s. 2H), 6.93-6.98 (m, 2H), 7.19-7.50 (m, 15H).

(22) Compound 22 was synthesized according to the procedure described for the preparation of 19a, starting from the benzyl ester 21 (300 mg, 0.681 mmol). The obtained product 22 (214 mg, 95%, white solid) was used in the subsequent reaction without further purification.

H$^1$-NMR (d$^6$-DMSO, 200 MHz): 3.77-3.79 (m, 5H), 6.98-7.03 (m, 2H), 7.20-7.25 (m, 2H), 7.30-7.39 (m, 4H), 7.56-7.61 (m, 4H).

(23) Compound 23 was synthesized according to the procedure described for the preparation of 12, starting from the carboxylic acid 22 (200 mg, 0.57 mmol). The obtained product was purified by flash chromatography (Eluent: AcOEt:n-Hexane 1:2), there were obtained 164 mg (63%, white solid) of 23.

$^1$H-NMR (CDCl$_3$, 200 MHz): 3.65 (s, 2H), 3.85 (s, 3H), 4.82 (s, 2H), 6.94-6.99 (m, 2H), 7.14-7.18 (m, 2H), 7.29-7.50 (m, 13H), 8.08 (br s, 1H).

(24) The hydroxamic acid 24 was obtained starting from the compound 23 (164 mg, 0.36 mmol) following the procedure described in the preparation of 13. The crude product obtained was purified through trituration with CH$_2$Cl$_2$ and toluene: there were obtained 26 mg of 24 (20%, white solid).

$^1$H-NMR (d$_6$-DMSO, 200 MHz): 3.55 (s, 2H), 3.78 (s, 3H), 6.99-7.03 (m, 2H), 7.22-7.36 (m, 6H), 7.57-7.61 (m, 4H), 8.86 (s, 1H), 10.64 (s, 1H).

EXAMPLE 8

2-(2-(4'-methoxybiphenyl-4-ylthio)phenyl)-N-(methyl sulphonyl)acetamide (25)

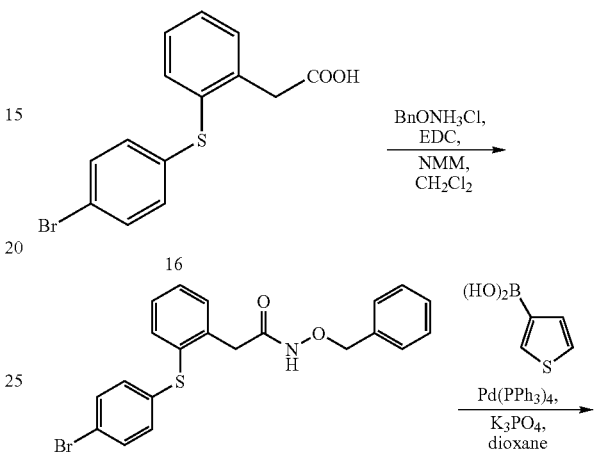

(25) Compound 25 was synthesized starting from the carboxylic acid 22 (100 mg, 0.285 mmol) following the procedure described for the preparation of compound 8.

The obtained product was purified through trituration with Et$_2$O and n-Hexane: there were recovered 67 mg of 25 (55%, white solid).

$^1$H-NMR (d$_6$-DMSO, 200 MHz): 3.16 (s, 3H), 3.79 (s, 3H), 3.87 (s, 2H), 6.99-7.03 (m, 2H), 7.17-7.23 (m, 2H), 7.32-7.41 (m, 4H), 7.56-7.60 (m, 4H), 11.88 (br s, 1H).

EXAMPLE 9

N-hydroxy-2-(2-(4-(thiophene-3-yl)phenylthio)phenyl)acetamide (30)

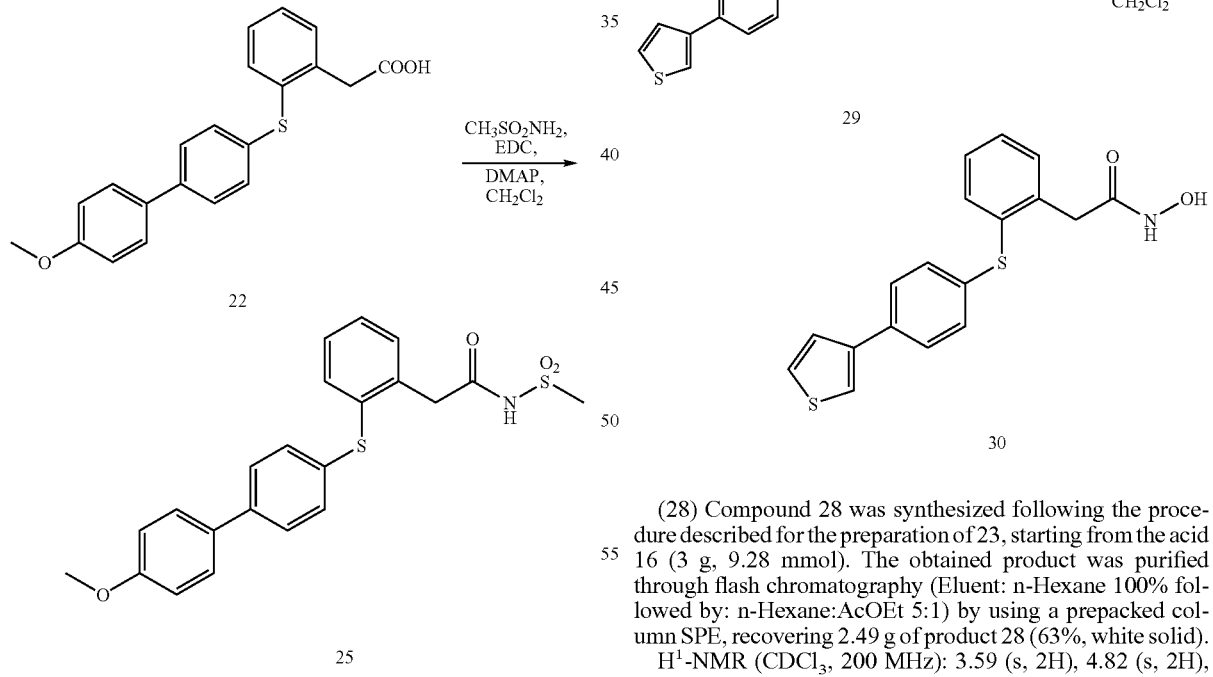

(28) Compound 28 was synthesized following the procedure described for the preparation of 23, starting from the acid 16 (3 g, 9.28 mmol). The obtained product was purified through flash chromatography (Eluent: n-Hexane 100% followed by: n-Hexane:AcOEt 5:1) by using a prepacked column SPE, recovering 2.49 g of product 28 (63%, white solid).

H$^1$-NMR (CDCl$_3$, 200 MHz): 3.59 (s, 2H), 4.82 (s, 2H), 6.93-6.97 (m, 2H), 7.27-7.39 (m, 11H), 8.07 (br s, 1H).

(29) Compound 29 was synthesized following the procedure described for the preparation of 21, starting from compound 28 (400 mg, 0.934 mmol). The obtained crude was purified through flash chromatography (Eluent: n-Hexane: AcOEt 3:1) obtaining 235 mg of 29 (58%, white solid).

H$^1$-NMR (d$^6$-CDCl$_3$, 200 MHz): 3.63 (s, 2H), 4.81 (s, 3H), 7.12-7.16 (m, 2H), 7.28-7.50 (m, 14H), 8.08 (br s, 1H).

(30) The hydroxamic acid 30 was obtained starting from the compound 29 (208 mg, 0.48 mmol) following the procedure described for the preparation of 23. The obtained crude product was purified through flash chromatography (Eluent: $CH_2Cl_2$:MeOH:n-Hexane 9:1:7) and there were obtained 84 mg of 30 (51%, white solid).

$^1$H-NMR ($d_6$-DMSO, 200 MHz): 3.53 (s, 2H), 7.10-7.36 (m, 8H), 7.53-7.56 (m, 1H), 7.62-7.71 (m, 2H), 7.87-7.89 (m, 1H), 8.86 (s, 1H), 10.64 (s, 1H).

EXAMPLE 10

N-hydroxy-2-[2-(4'-methylthio-biphenyl-4-ylthio)-phenyl]-acetamide (32)

(31) Compound 31 was synthesized following the procedure described for the preparation of 29, starting from compound 28 (400 mg, 0.934 mmol). The obtained crude product was purified through flash chromatography (Eluent: $CH_2Cl_2$ 100%, followed by n-Hexane: EtOAc:$CH_2CH_2$ 2:5:7; $CH_2CH_2$:MeOH 9:1), obtaining 428 mg of 31 (97%, white solid).

$^1$H-NMR ($CDCl_3$, 200 MHz): 2.51 (s, 3H), 3.64 (s, 2H), 4.81 (s, 3H), 7.14-7.18 (m, 3H), 7.28-7.48 (m, 14H), 8.06 (br s, 1H).

(32) The hydroxamic acid 32 was synthesized starting from the compound 31 (208 mg, 0.48 mmol) following the procedure described for the preparation of 30. The crude product obtained was purified through flash chromatography (Eluent: $CH_2Cl_2$:MeOH:n-Hexane 9:1:7); there were obtained 84 mg of 32 (51%, white solid).

$^1$H-NMR ($d_6$-DMSO, 200 MHz): 3.53 (s, 2H), 7.10-7.36 (m, 8H), 7.53-7.56 (m, 1H), 7.62-7.71 (m, 2H), 7.87-7.89 (m, 1H), 8.86 (s, 1H), 10.64 (s, 1H).

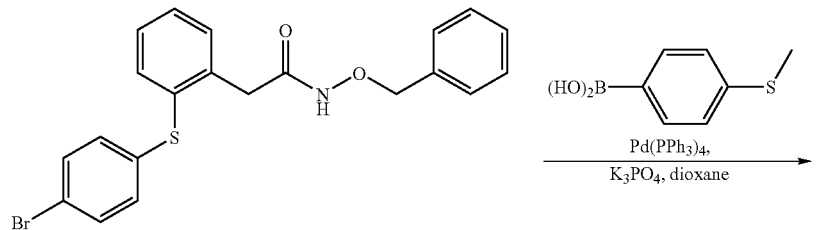

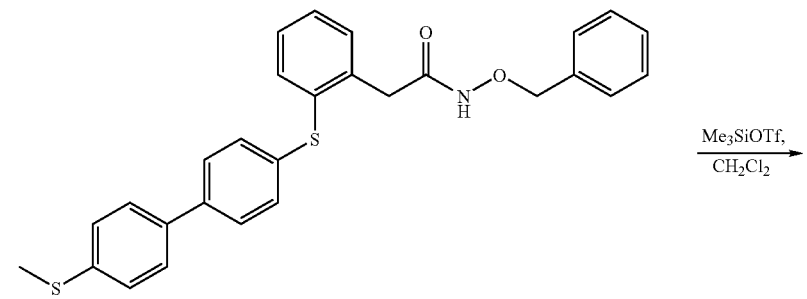

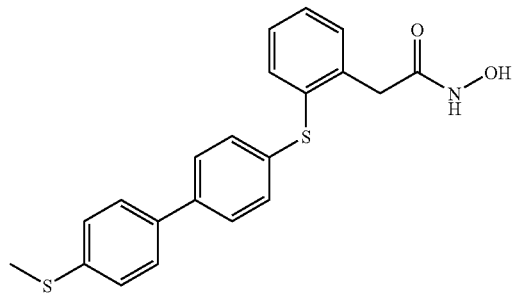

EXAMPLE 11

N-hydroxy-2-(2-(4-pyridin-4-yl-phenylthio)-phenyl)-acetamide (34)

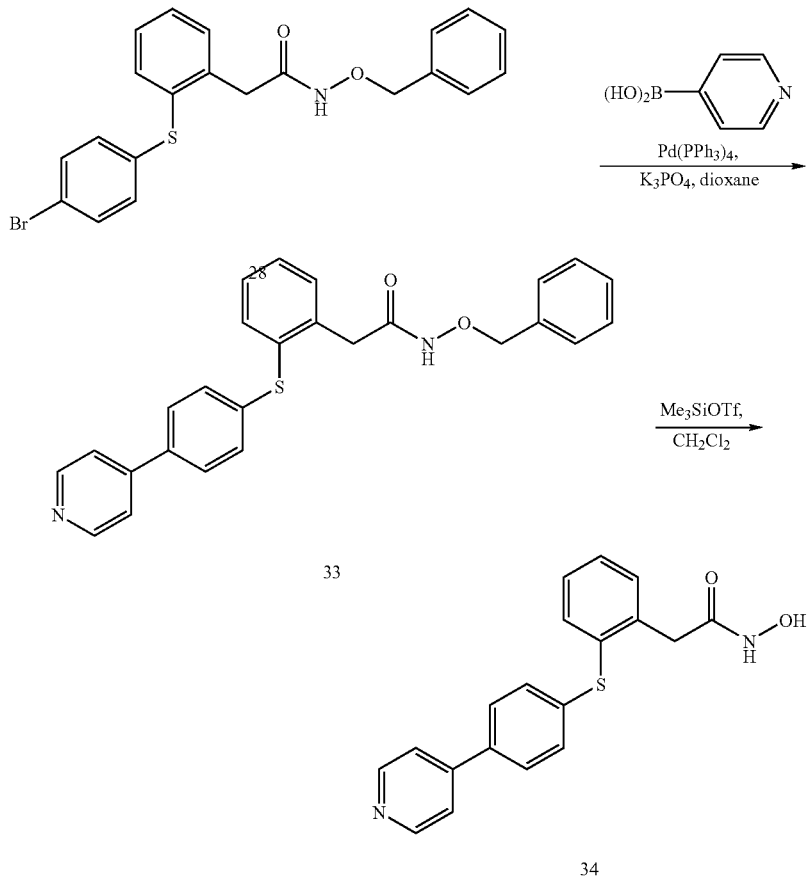

(33) Compound 33 was synthesized following the procedure described for the preparation of 29, starting from the compound 28 (350 mg, 0.817 mmol). The obtained crude was purified through flash chromatography (Eluent: EtOAc:n-Hexane 2:1), obtaining 284 mg of 33 (81%, white solid).

$^1$H-NMR (CDCl$_3$, 200 MHz): 3.63 (s, 2H), 4.81 (s, 2H), 7.13-7.18 (m, 2H), 7.28-7.34 (m, 5H), 7.39-7.71 (m, 9H), 8.29 (br s, 1H), 8.60 (br s, 1H).

(34) The hydroxamic acid 34 was obtained starting from the compound 33 (260 mg, 0.61 mmol), following the procedure described for the preparation of 30. The obtained crude product was purified through trituration with CH$_2$Cl$_2$/n-Hexane; there were recovered 60 mg of 34 (29%, white solid).

$^1$H-NMR (d$_6$-DMSO, 200 MHz): 3.54 (s, 2H), 7.23-7.42 (m, 6H), 7.67-7.78 (m, 4H), 8.60-8.63 (m, 2H), 8.84 (s, 1H), 10.62 (s, 1H).

EXAMPLE 12

2-(4-(4-methoxyphenoxy)phenylsulphonyl)benzoic acid (37) and 2-(4-(4-methoxyphenoxy)phenylsulphonyl)-N-(methylsulphonyl)benzamide (38)

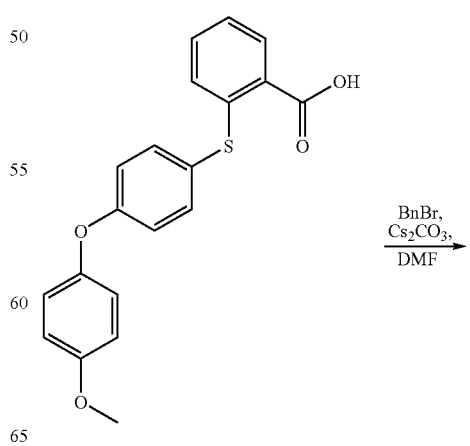

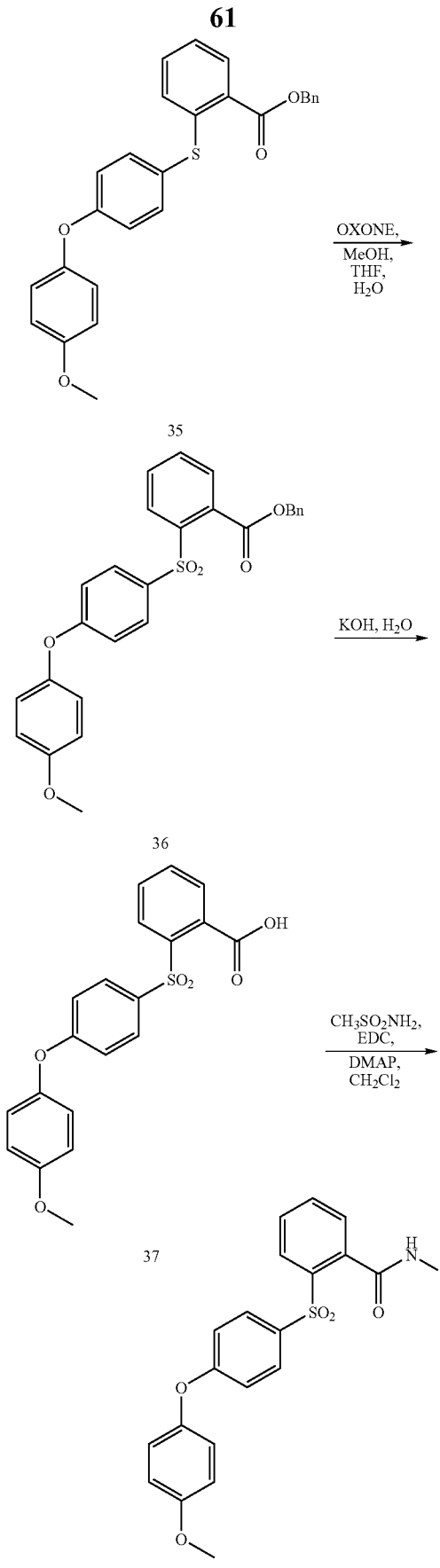

(35) The benzyl ester 35 was obtained starting from the acid 4 (162 mg, 0.46 mmol), following the procedure described for the preparation of 17. There were recovered 183 mg of 35 (91% yellow solid).

$^1$H-NMR (CDCl$_3$, 200 MHz): 3.82 (s, 3H), 5.40 (s, 2H), 6.78-6.82 (m, 1H), 6.90-7.13 (m, 7H), 7.21-7.30 (m, 1H), 7.34-7.51 (m, 7H), 8.00-8.05 (m, 1H).

(36) To a solution of 35 (180 mg, 0.41 mmol) in THF/MeOH (1:1, 4 mL) there was added a solution of Oxone® (1.5 g, 2.46 mmol) in H$_2$O (7 mL). The reaction was left stirring for one day, there were also added further 3 g of Oxone® and the reaction was left stirring for further 5 days. The organic solvents were then removed through evaporation under reduced pressure, the obtained suspension was diluted with H$_2$O and the product was extracted with EtOAc. There were obtained 148 mg of 36 (77%, white solid).

$^1$H-NMR (CDCl$_3$, 200 MHz): 3.82 (s, 3H), 5.40 (s, 2H), 6.83-6.99 (m, 6H), 7.32-7.46 (m, 5H), 7.53-7.61 (m, 3H), 7.84-7.89 (m, 2H), 8.05-8.09 (m, 1H).

(37) The carboxilic acid 37 was synthesized following the procedure described for the preparation of 18, starting from the benzyl ester 36 (140 mg, 0.295 mmol). The obtained crude was not further purificated and there were recovered 106 mg (94%, yellow oil) of 37.

$^1$H-NMR (CDCl$_3$, 200 MHz): 3.80 (s, 3H), 6.87-7.00 (m, 5H), 7.31-7.42 (m, 1H), 7.63-7.75 (m, 3H), 7.90-7.95 (m, 2H), 8.16-8.20 (m, 1H).

(38) The compound 38 was synthesized starting from the carboxylic acid 37 (100 mg, 0.26 mmol) following the procedure described for the preparation of 8. The obtained product was purified through flash chromatography (Eluent: CH$_2$Cl$_2$: MeOH 98:2); there were recovered 29 mg of 38 (24%, white solid).

$^1$H-NMR (d$_6$-DMSO, 200 MHz): 3.32 (s, 3H), 3.77 (s, 3H), 6.98-7.12 (m, 6H), 7.51-7.55 (m, 1H), 7.64-7.76 (m, 2H), 7.94-8.09 (m, 3H), 12.50 (br s, 1H).

EXAMPLE 13

2-(2-(4-(4-methoxyphenoxy)phenylthio)phenyl)-N-(methyl sulphonyl)acetamide (39)

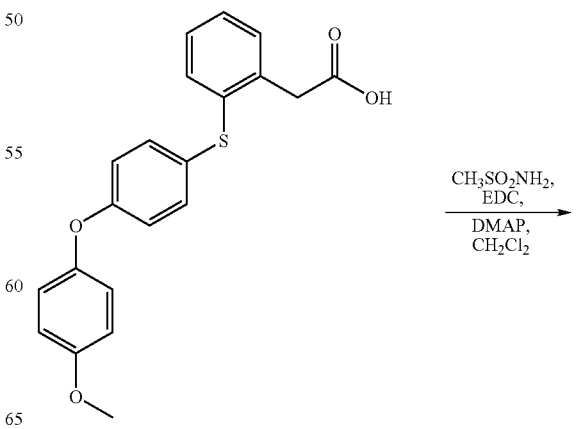

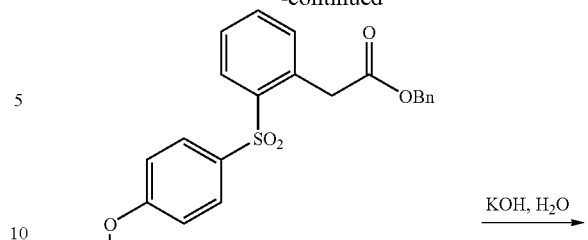

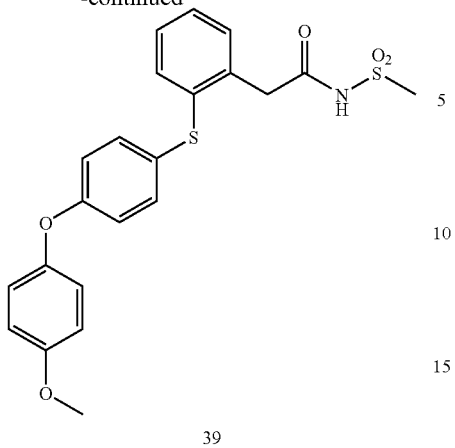

39

(39) The compound 39 was synthesized from the carboxylic acid 11 (100 mg, 0.285 mmol) with the procedure described for the preparation of 25. The obtained product was purified through trituration with Et$_2$O and n-Hexane; there were recovered 67 mg of 39 (55%, white solid).

$^1$H-NMR (d$_6$-DMSO, 200 MHz): 3.16 (s, 3H), 3.79 (s, 3H), 3.87 (s, 2H), 6.99-7.03 (m, 2H), 7.17-7.23 (m, 2H), 7.32-7.41 (m, 4H), 7.56-7.60 (m, 4H), 11.88 (br s, 1H).

EXAMPLE 14

2-(2-(4-(4-methoxyphenoxy)phenylsulphonyl)phenyl)-N-(methyl sulphonyl)acetamide (43)

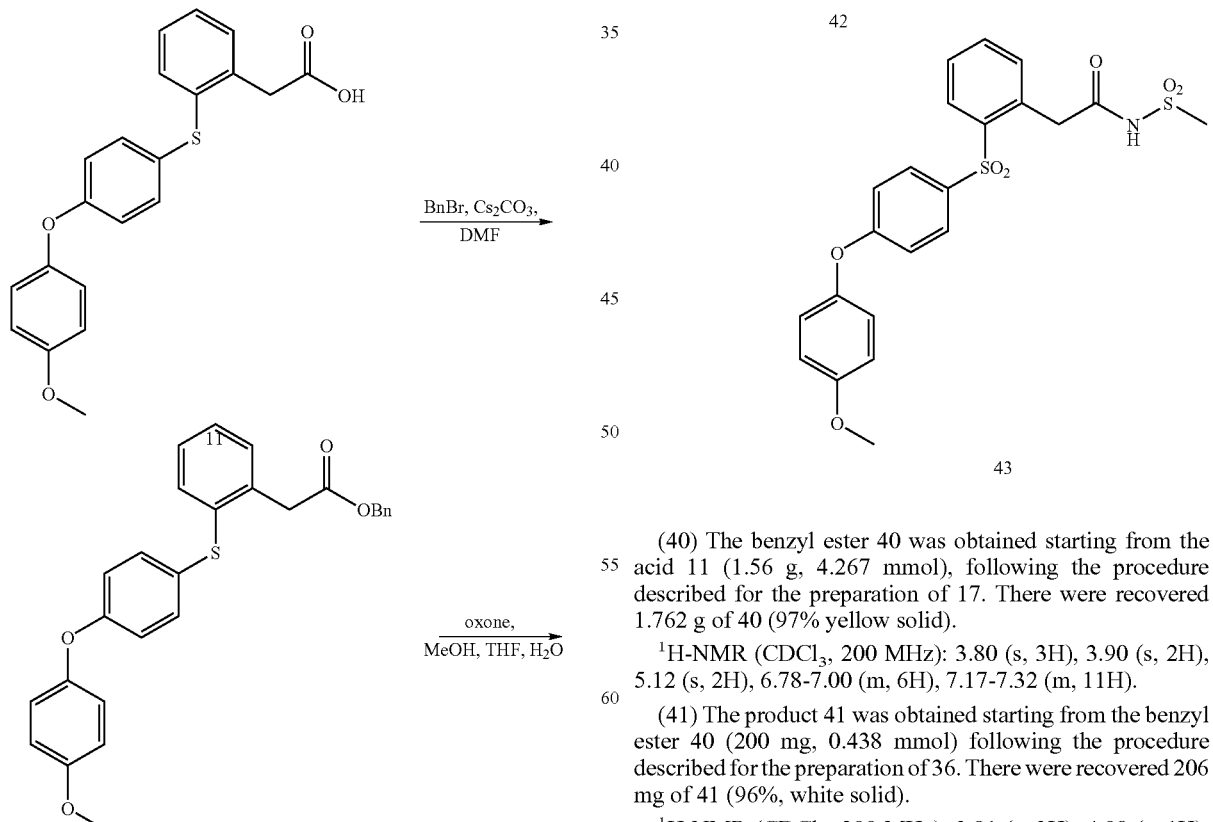

(40) The benzyl ester 40 was obtained starting from the acid 11 (1.56 g, 4.267 mmol), following the procedure described for the preparation of 17. There were recovered 1.762 g of 40 (97% yellow solid).

$^1$H-NMR (CDCl$_3$, 200 MHz): 3.80 (s, 3H), 3.90 (s, 2H), 5.12 (s, 2H), 6.78-7.00 (m, 6H), 7.17-7.32 (m, 11H).

(41) The product 41 was obtained starting from the benzyl ester 40 (200 mg, 0.438 mmol) following the procedure described for the preparation of 36. There were recovered 206 mg of 41 (96%, white solid).

$^1$H-NMR (CDCl$_3$, 200 MHz): 3.81 (s, 3H), 4.08 (s, 1H), 5.03 (s, 2H), 6.87-6.99 (m, 6H), 7.30-7.35 (m, 5H), 7.43-7.59 (m, 3H), 7.72-7.78 (m, 2H), 8.11-8.16 (m, 1H).

(42) The product 42 was synthesized following the procedure described for the preparation of 18, starting from the benzyl ester 41 (200 mg, 0.41 mmol). The obtained crude was purified through trituration with Et$_2$O/n-hexane recovering 133 mg (81%, white solid) of 42.

$^1$H-NMR (d$_6$-DMSO, 200 MHz): 3.76 (s, 3H), 3.91 (s, 2H), 6.98-7.13 (m, 6H), 7.41-7.59 (m, 3H), 7.79-7.83 (m, 2H), 8.01-8.05 (m, 1H), 12.33 (s, 1H).

(43) The compound 43 was synthesized starting from the carboxylic acid 42 (80 mg, 0.201 mmol) following the procedure described for the preparation of 8. The obtained product was purified through trituration with Et$_2$O; there were recovered 66 mg of 43 (70%, white solid).

$^1$H-NMR (d$_6$-DMSO, 200 MHz): 3.18 (s, 3H), 3.77 (s, 3H), 4.00 (s, 2H), 6.98-7.12 (m, 6H), 7.40-8.06 (m, 6H), 11.93 (br s, 1H).

EXAMPLE 15

2-(4'-methoxybiphenyl-4-ylthio)-N-(methylsulphonyl)benzamide (48) and 2-(4'-methoxybiphenyl-4-ylsulphonyl)-N-(methylsulphonyl)benzamide (106)

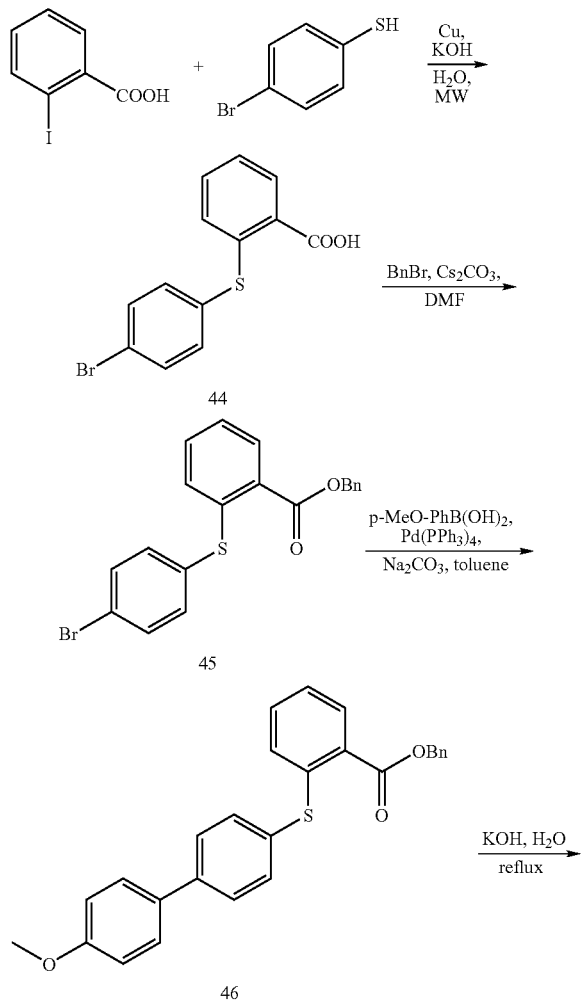

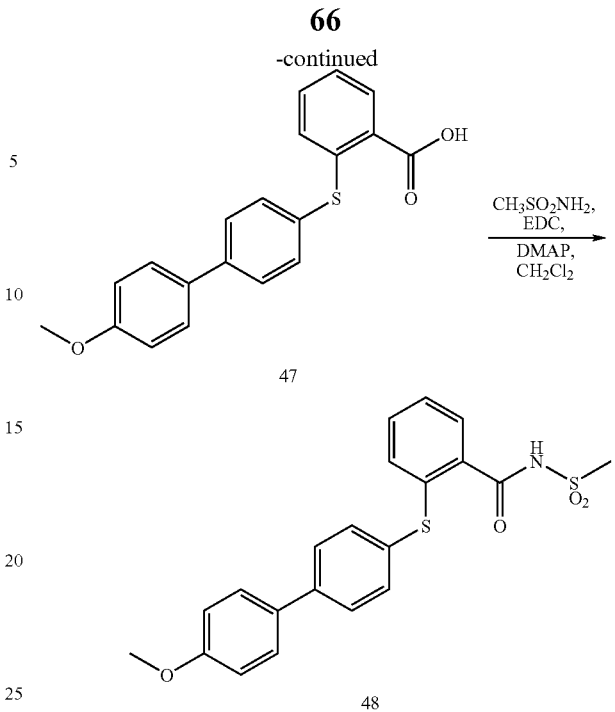

(44) The compound 44 was synthesized starting from 2 iodo-benzoic acid (3 g, 16.1 mmol) and 4-bromobenzenthiolo (2.2 g, 16.1 mmol) following the procedure for the preparation of 1. The crude obtained was purified through trituration with acetone; there were recovered 3.1 g of 44 (82%, white solid).

$^1$H-NMR (d$_6$-DMSO 200 MHz): δ 6.65 (d, 1H), 6.68 (d, 2H), 7.09-7.20 (m, 1H), 7.29-7.40 (m, 3H), 7.90 (d, 1H), 9.98 (br. s, 1H).

(45) The compound 45 was synthesized starting from the acid 44 (3 g, 9.7 mmol) following the procedure described for the preparation of 17. There were recovered 3.7 g of 45 (94%, yellow solid).

$^1$H-NMR (d$_6$-DMSO 200 MHz): δ 6.65 (d, 1H), 6.68 (d, 2H), 7.09-7.20 (m, 1H), 7.29-7.40 (m, 3H), 7.90 (d, 1H), 9.98 (br. s, 1H).

(46) The compound 46 was synthesized starting from the benzyl ester 45 (1.55 g, 3.9 mmol) following the procedure described for the preparation of 29. The crude obtained was purified through flash chromatography (Eluent: n-Hexane:CH$_2$Cl$_2$ 3:7, n-Hexane:CH$_2$Cl$_2$ 4:6), the obtained product was further purified through trituration with Et$_2$O/n-Hexane. There were recovered 1.29 g of 46 (78%, white solid).

$^1$H-NMR (CDCl$_3$, 200 MHz): 3.87 (s, 3H), 5.41 (s, 2H), 6.89-7.61 (m, 16H), 8.01-8.06 (m, 1H).

(47) The compound 47 was synthesized starting from the benzyl ester 46 (1.01 g, 2.37 mmol) following the procedure described for the preparation of 22. The obtained product was purified through trituration with Et$_2$O/n-Hexane. There were recovered 693 mg of 47 (87%, white solid).

$^1$H-NMR (d$_6$-DMSO, 200 MHz): 3.81 (s, 3H), 6.80-6.84 (m, 1H), 7.04-7.08 (m, 2H), 7.18-7.25 (m, 1H), 7.36-7.43 (m, 1H), 7.55-7.60 (m, 2H), 7.67-7.78 (m, 4H), 7.92-7.95 (m, 1H), 13.22 (br s, 1H).

(48) The compound 48 was synthesized starting from the carboxylic acid 47 (70 mg, 0.208 mmol) following the procedure described for the preparation of 8. There were recovered 75 mg of 48 (89%, white solid).

$^1$H-NMR (d$_6$-DMSO 200 MHz): δ 3.35 (s, 3H), 3.80 (s, 3H), 7.01-7.15 (m, 3H), 7.33-7.49 (m, 4H), 7.63-7.70 (m, 5H), 12.30 (br s, 1H).

By working in a substantially analogous way and by starting from a corresponding sulphonyl derivative, also compound 2-(4'-methoxybiphenyl-4-yl-sulphonyl)-N-(methyl sulphonyl)benzamide (106), below, was obtained $^1$H-NMR (d$_6$-DMSO, 200 MHz): 3.35 (s, 3H), 3.80 (s, 3H), 7.01-7.15 (m, 3H), 7.33-7.49 (m, 4H), 7.63-7.70 (m, 5H), 12.30 (br s, 1H).

EXAMPLE 16

2-(4'-methoxybiphenyl-4-ylthio)-N-(trifluoromethyl sulphonyl)benzamide (49)

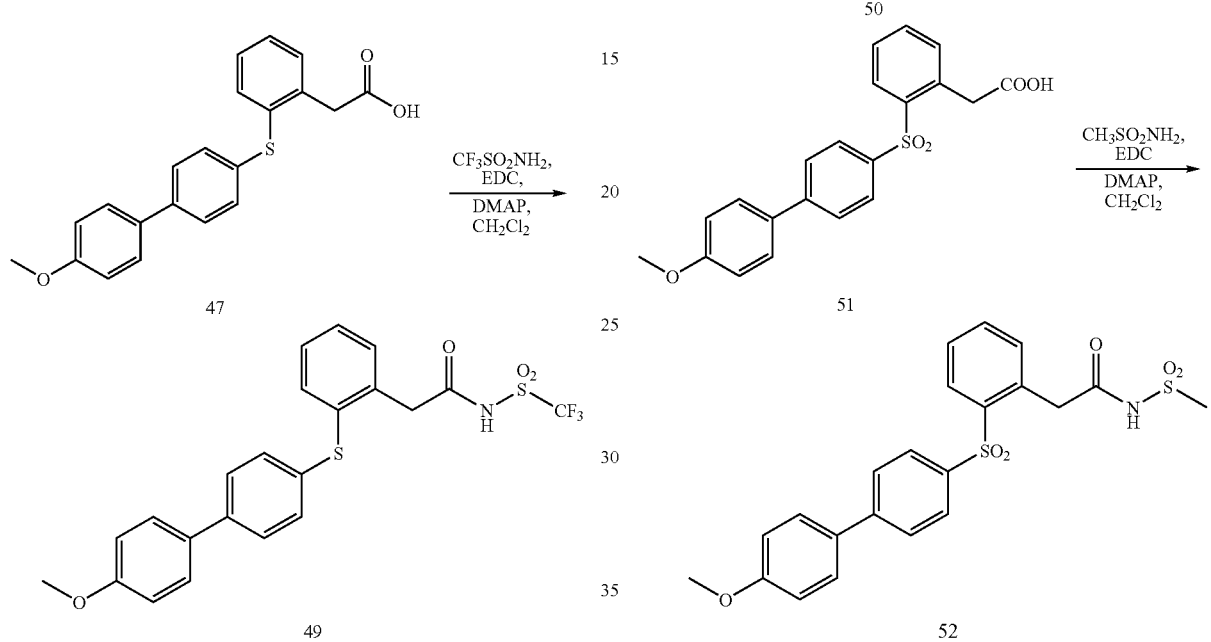

(49) The compound 49 was synthesized starting from the carboxylic acid 47 (80 mg, 0.228 mmol) following the procedure described for the preparation of 8, using trifluoromethanesulphonamide in place of methanesulphonamide. The obtained product was purified through flash chromatography (Eluent: CH$_2$Cl$_2$:MeOH 98:2, CH$_2$Cl$_2$:MeOH 95:5): there were recovered 33 mg of 49 (30%, white solid).

$^1$H-NMR (d$_6$-DMSO, 200 MHz): 3.78 (s, 5H), 6.99-7.03 (m, 2H), 7.19-7.36 (m, 6H), 7.55-7.61 (m, 4H).

EXAMPLE 17

2-(2-(4'-methoxybiphenyl-4-sulphonyl)phenyl)-N-(methyl sulphonyl)acetamide (52)

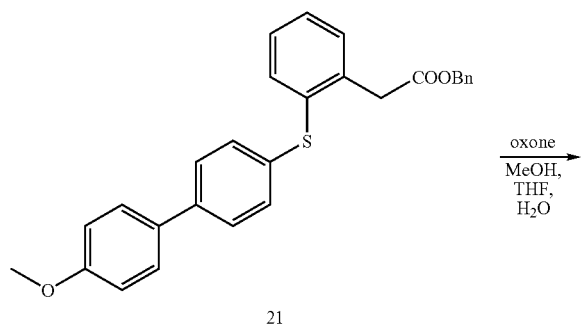

(50) The product 50 was obtained starting from the benzyl ester 21 (306 mg, 0.695 mmol) following the procedure described for the preparation of 36. There were recovered 271 mg of 50 (85%, white solid).

$^1$H-NMR (CDCl$_3$, 200 MHz): 3.86 (s, 3H), 4.10 (s, 1H), 4.97 (s, 2H), 6.96-7.02 (m, 2H), 7.21-7.35 (m, 5H), 7.44-7.60 (m, 7H), 7.85-7.89 (m, 2H), 8.19-8.24 (m, 1H).

(51) The product 51 was synthesized following the procedure described for the preparation of 18, starting from the benzyl ester 50 (250 mg, 0.53 mmol). The crude obtained was purified through trituration with Et$_2$O/n-Hexane obtaining 191 mg (94%, white solid) of 51.

$^1$H-NMR (d$_6$-DMSO, 200 MHz): 3.80 (s, 3H), 3.94 (s, 2H), 7.04-7.08 (m, 2H), 7.42-7.71 (m, 5H), 7.81-7.86 (m, 4H), 8.08-8.13 (m, 1H), 12.36 (s, 1H).

(52) The compound 52 was synthesized starting from the carboxylic acid 51 (80 mg, 0.209 mmol) following the procedure described for the preparation of 8. The obtained product was purified through trituration with Et$_2$O: there were recovered 68 mg of 52 (71%, white solid).

$^1$H-NMR (d$_6$-DMSO, 200 MHz): 3.16 (s, 3H), 3.80 (s, 3H), 4.04 (s, 2H), 7.04-7.08 (m, 2H), 7.42-7.47 (m, 1H), 7.55-7.71 (m, 4H), 7.82-7.99 (m, 4H), 8.09-9.13 (m, 1H), 11.88 (br s, 1H).

EXAMPLE 18

N-hydroxy-2-(2-(4'-methoxybiphenyl-4-ylthio)phenyl)propanamide (56a) and analogous (56b) of formula below

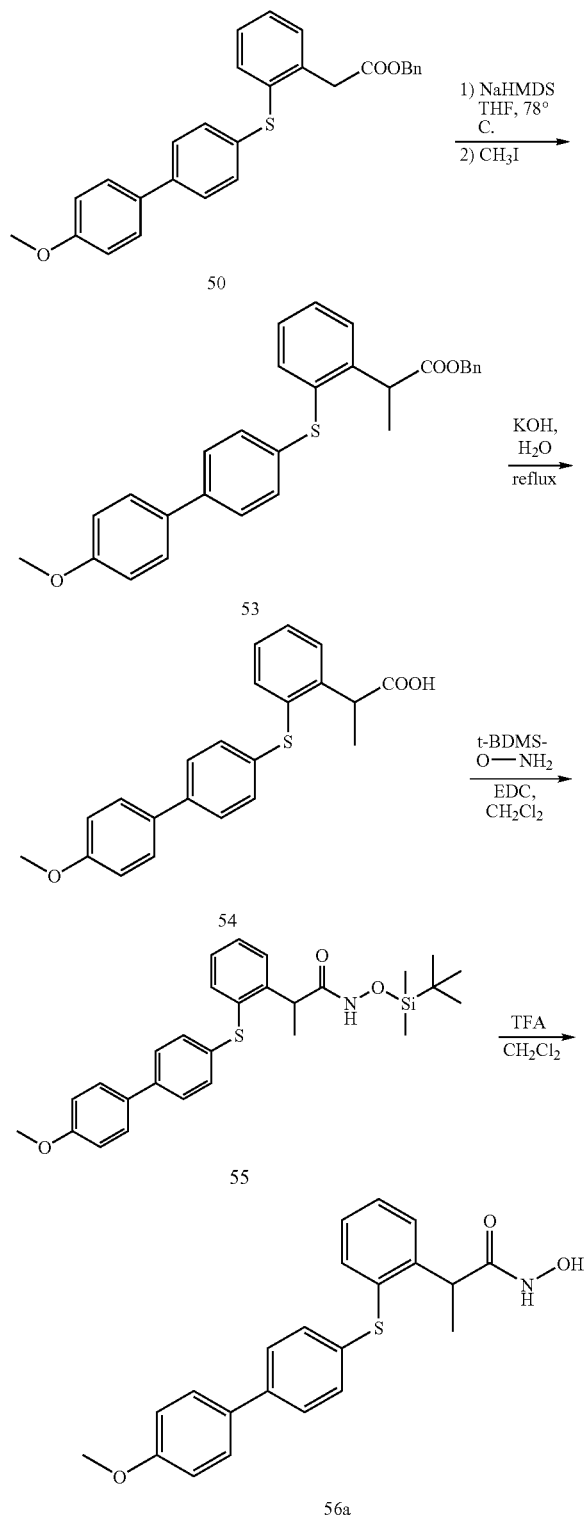

(53) To a solution of the benzyl ester 50 (1.15 g, 2.61 mmol) in anhydrous THF (16 mL) and under inert atmosphere (nitrogen) at −78° C. for 1 hour, it was dropped Sodium bis(trimethylsilyl)amide 1M in anhydrous THF (NaHMDS, 2.87 mL). The solution was left stirring at 78° C. for 1 hour, methyl iodide (813 µL, 13.06 mmol) was then added and the solution was maintained at −78° C. for 1 hour and at −50° C. for further 2 hours. The reaction mixture was then quenched by adding a solution of $CH_3COOH$ (448 µL, 7.83 mmol), in $Et_2O$ (10.4 mL). The formed precipitate was filtered on Celite® and the filtrate was evaporated under reduced pressure. The crude product obtained was purified through filtration chromatography (Eluent: AcOEt: n-Hexane 8:2). There were recovered 950 mg of 53 (80%, yellow solid).

$^1$H-NMR (CDCl$_3$, 200 MHz): 1.48 (d, J=7.14 Hz, 3H), 3.85 (s, 3H), 4.55 (q, J=7.14 Hz, 1H), 5.06 (s, 1H), 5.07 (s, 1H), 6.93-6.98 (m, 2H), 7.17-7.48 (m, 15H).

(54) The product 54 was synthesized following the procedure described for the preparation of 18, starting from the benzyl ester 53 (400 mg, 0.880 mmol). The crude compound obtained was purified through trituration with $Et_2O$/n-Hexane obtaining 250 mg of 54 (80%, white solid).

$^1$H-NMR (d$_6$-DMSO, 200 MHz): 1.34 (d, J=7.08 Hz, 3H), 3.79 (s, 3H), 4.27 (q, J=7.08 Hz, 1H), 6.98-7.03 (m, 2H), 7.22-7.40 (m, 6H), 7.57-7.61 (m, 4H), 12.37 (br s, 1H).

(55) To a solution of the carboxylic acid 54 (80 mg, 0.219 mmol) and O-tButyldimethylsilyl hydroxylamine (t-BDMS-O—NH$_2$, 32 mg 0.219 mmol) in anhydrous $CH_2Cl_2$ (11 mL) and maintained under inert atmosphere (nitrogen), it was added EDC (42 mg, 0.219 mmol). The solution was kept under stirring at room temperature for 18 hours, then it was diluted with $CH_2Cl_2$ and washed with $H_2O$ and with HCl 1N. There were recovered 106 mg of 55 (98%, yellow oil) used in the following reaction without further purification.

$^1$H-NMR (CDCl$_3$, 200 MHz): 0.04 (d, J=2.75 Hz, 6H), 0.85 (s, 9H), 1.46 (d, J=7.14 Hz, 3H), 3.84 (s, 3H), 4.17 (q, J=7.14 Hz, 1H), 6.94-6.99 (m, 2H), 7.18-7.63 (m, 10H).

(56a) To a solution of 55 (100 mg, 0.203 mmol) in anhydrous $CH_2Cl_2$ (313 µL) and kept under inert atmosphere (nitrogen) at 0° C., it was added trifluoracetic acid (TFA, 313 µL). The solution was kept under stirring, leaving the temperature reaching slowly the room temperature, for 5 hours. The solution was then brought to dryness and the residue was several times recovered with ether and brought to dryness under reduced pressure. The crude product was purified through flash chromatography (Eluent: $CH_2Cl_2$:MeOH 97:3) and subsequent trituration with $Et_2O$; there were recovered 35 mg of 56a (45%, white solid).

$^1$H-NMR (d$_6$-DMSO, 200 MHz): 1.30 (d, J=7.08 Hz, 3H), 3.79 (s, 3H), 4.10 (q, J=7.08 Hz, 1H), 6.99-7.03 (m, 2H), 7.25-7.36 (m, 6H), 7.58-7.62 (m, 4H), 8.12 (s, 1H).

By working in an analogous way and by using selected halides (see details below) in place of methyl iodide, as per the preparation of 53, the following compound was also obtained:

by using allyl bromide it was obtained N-hydroxy-2-(2-(4'-methoxybiphenyl-4-ylthio)phenyl)pent-4-enamide (56b)

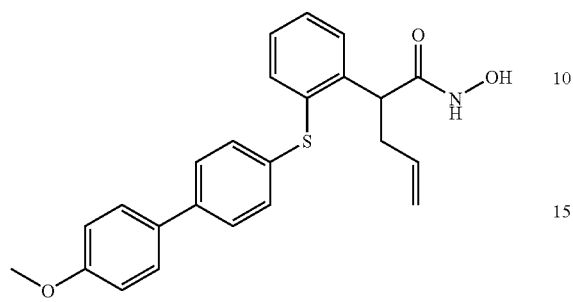

56b

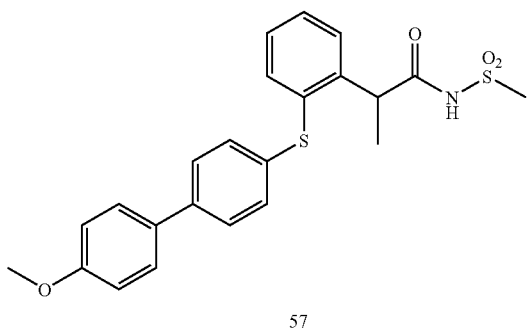

57

¹H-NMR (CDCl₃, 200 MHz): 7.51-7.19 (m, 10H); 6.96 (d, J=8.5 Hz 2H); 5.72 (m, 1H); 4.98 (m, 2H); 4.52 (t, J=7.5 Hz, 1H); 3.84 (s, 3H); 2.8 (quintet, J=7 Hz, 1H); 2.45 (quintet, J=7 Hz, 1H). Anal. Calcd for $C_{24}H_{23}NO_3S$ (MW=405.5): C, 71.09; H, 5.72; O, 11.84; S, 7.91.

(57) The compound 57 was synthesized starting from the carboxylic acid 54 (80 mg, 0.219 mmol) following the procedure described for the preparation of 8. There were recovered 84 mg of 57 (80%, white solid).

¹H-NMR (CDCl₃, 200 MHz): 1.48 (d, J=7.00, 3H), 3.12 (s, 3H) 3.85 (s, 3H), 4.30 (q, J=7.00 Hz, 1H), 6.95-6.99 (m, 2H), 7.24-7.40 (m, 5H), 7.48-7.54 (m, 5H).

EXAMPLE 19

2-(2-(4'-methoxybiphenyl-4-ylthio)phenyl)-N-(methyl sulphonyl)propanamide (57)

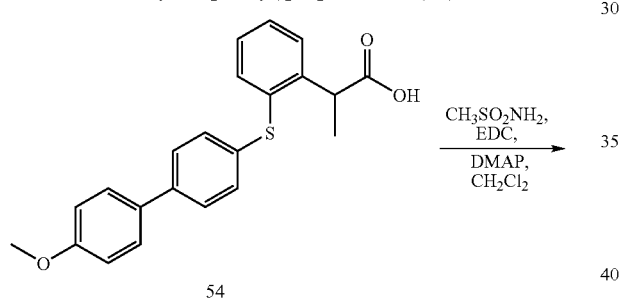

EXAMPLE 20

2-(4-(4-methoxyphenoxy)phenylthio)benzylphosphonic acid (70) and 2-(4-(4-methoxyphenoxy)phenylsulphonyl)benzyl phosphonic acid (72)

r

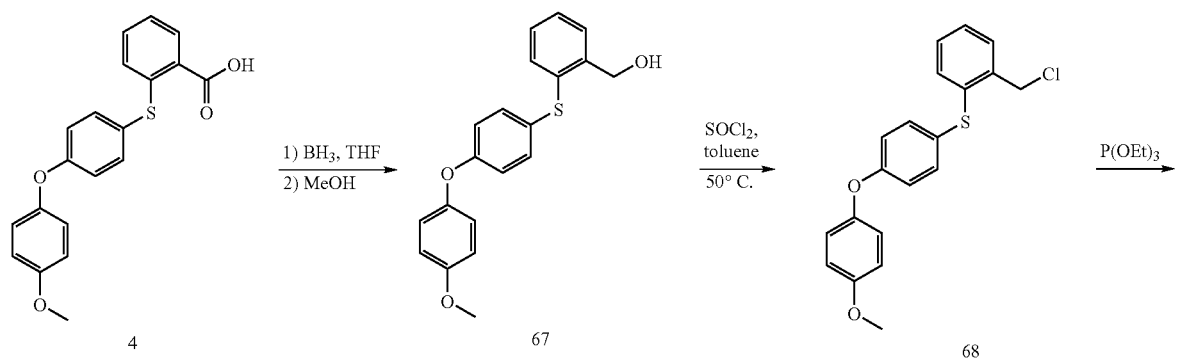

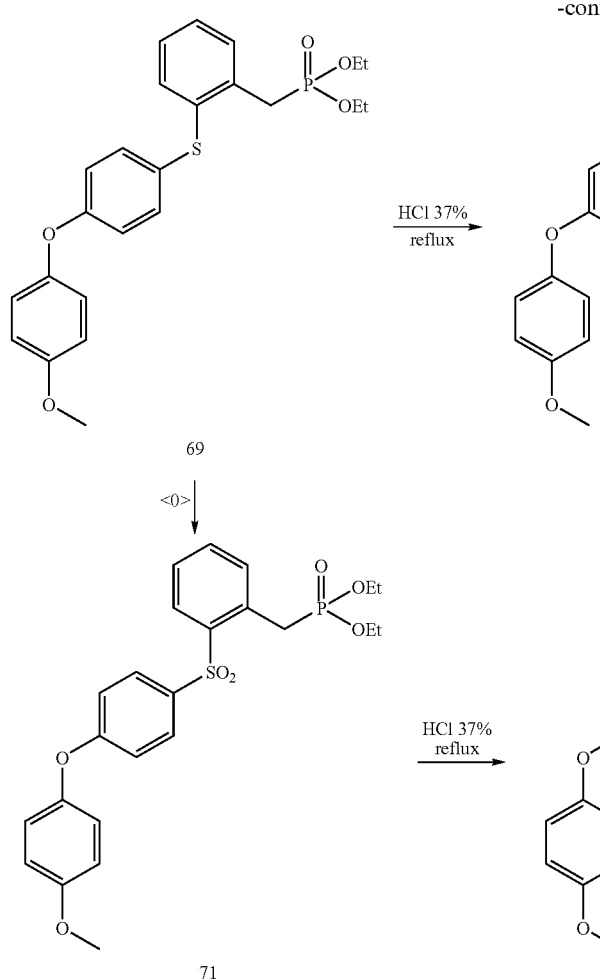

(67) To the solid compound 4 (220 mg, 0.624 mmol), at 0° C. under inert atmosphere, it was added a 1M solution of $BH_3$ in THF (321 μL, 0.312 mmol). The solution was kept under stirring at room temperature for 5 hours, then further 500 μL of $BH_3$ 1M were added and the solution was left stirring for further 2 hours. The reaction was then quenched with MeOH (5 mL) and left stirring overnight. The solution was then brought to dryness and the residue was recovered with $CH_2Cl_2$. The solution was then treated with a saturated solution of $NaHCO_3$ and the product was extracted with $CH_2Cl_2$. The organic phase was dried over $Na_2SO_4$ and evaporated under reduced pressure. There were recovered 260 mg of 67 (97%, yellow oil).

$^1$H-NMR ($CDCl_3$, 200 MHz): 3.81 (s, 3H), 4.80 (s, 2H), 6.86-7.02 (m, 6H), 7.20-7.29 (m, 5H), 7.44-7.48 (m, 1H).

(68) To a solution of 67 (190 mg, 0.561 mmol) in anhydrous $CH_2Cl_2$ there was added dropwise thionyl chloride and one drop of pyridine. The solution was stirred at room temperature for 30 minutes. The reaction was then quenched with $H_2O$ and the product was extracted with $Et_2O$. The organic phase was then washed with brine, dried over $Na_2SO_4$ and evaporated under reduced pressure. There were recovered 185 mg of di 68 (93%, yellow oil).

$^1$H-NMR ($CDCl_3$, 200 MHz): 3.81 (s, 3H), 4.80 (s, 2H), 6.86-7.03 (m, 6H), 7.12-7.35 (m, 5H), 7.42-7.47 (m, 1H).

(69) In a two-neck flask provided with cooler, this latter connected to a trap at −18° C., the compound 68 (180 mg, 0.504 mmol) was dissolved in triethylphosphite (216 μL, 1.26 mmol) and kept at 140° C. After 2 h a further addition of triethylphosphite (216 μL, 1.26 mmol) occurred and the reaction mixture was kept under stirring at 140° C. for further 2 h. The excess of phosphite was then distilled off ($T_{eb}$=160° C.) and the residue was recovered with ether and brought to dryness again. There were recovered 225 mg of 69 (97% yellow oil).

$^1$H-NMR ($CDCl_3$, 200 MHz): 1.26 (t, J=6.9 Hz, 6H), 3.48 (d, J=22.0 Hz, 2H), 3.80 (s, 3H), 3.98-4.12 (m, 4H), 6.85-7.00 (m, 6H), 7.13-7.25 (m, 5H), 7.41-7.47 (m, 1H).

(70) A solution of 69 (200 mg, 0.408 mmol) in HCl 37% (12.2 mL) was refluxed for one night thus obtaining the desired phosphonate 70.

$^1$H-NMR ($d_6$-DMSO 200 MHz) δ 3.46 (d, J=22.2 2H), 3.76 (s, 3H), 7.01-7.12 (m, 6H), 7.40-8.02 (m, 6H).

(71) The compound 71 was obtained starting from 69 and by following the procedure described for the preparation of 36. The obtained crude product was purified through flash chromatography (Eluent: AcOEt: n-Hexane 6:4). There were recovered 200 mg of 71 (87%, yellow solid).

$^1$H-NMR ($CDCl_3$, 200 MHz) δ: 1.19 (t, J=7.1 Hz, 6H), 3.69 (d, J=22.7 Hz, 2H), 3.82 (s, 3H), 3.91-4.07 (m, 4H), 6.88-7.00 (m, 6H), 7.37-7.57 (m, 2H), 7.69-7.85 (m, 3H), 8.08-8.12 (m, 1H).

(72) The compound 72 was obtained starting from compound 71 and by following the procedure described for the preparation of 70.

$^1$H-NMR (d$_6$-DMSO 200 MHz) δ: 3.39 (d, J=22.2 2H), 3.79 (s, 3H), 7.06-7.12 (m, 6H), 7.45-8.12 (m, 6H).

EXAMPLE 21

2-(4'-methoxybiphenyl-4-ylthio)benzylphosphonic acid (85)

2-(4'-methoxybiphenyl-4-ylsulphonyl)benzylphosphonic acid (86)

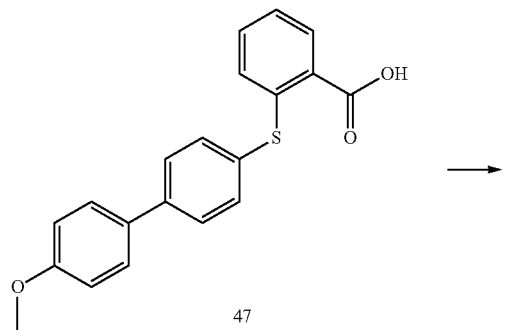

47

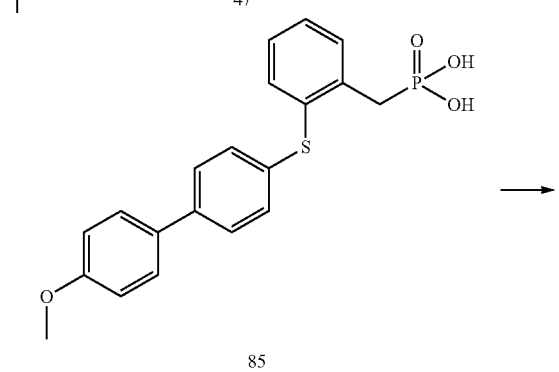

85

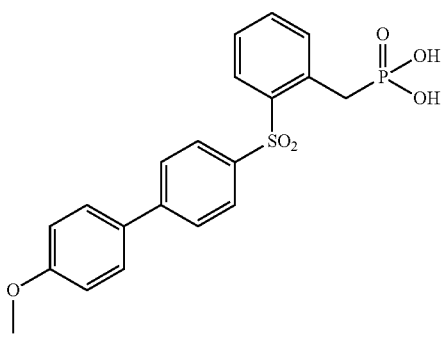

86

(85, 86) The 2-(4'-methoxybiphenyl-4-ylthio)benzoic acid 47, needed for the synthesis of this series of compounds, was prepared in the example 15 and treated in the conditions already described in the examples 20, thus obtaining the derivatives 85 and 86.

(85): $^1$H-NMR (d$_6$-DMSO, 200 MHz): 2.60 (s, 2H), 3.83 (s, 3H), 4.80 (brs, 2H), 6.80-6.84 (m, 1H), 7.04-7.08 (m, 2H), 7.18-7.25 (m, 1H), 7.36-7.43 (m, 1H), 7.55-7.60 (m, 2H), 7.67-7.78 (m, 4H), 7.92-7.95 (m, 1H).

(86): $^1$H-NMR (d$_6$-DMSO, 200 MHz): 2.58 (s, 2H), 3.81 (s, 3H), 4.80 (brs, 2H), 7.02-7.24 (m, 5H), 7.65 (m, 2H), 7.77 (m, 2H), 7.96 (m, 2H).

EXAMPLE 22

Compounds (5-bis), (7a-bis) and (7b-bis)

To avoid ambiguity with any previously prepared compound, the following derivatives have been presently identified as compounds "-bis".

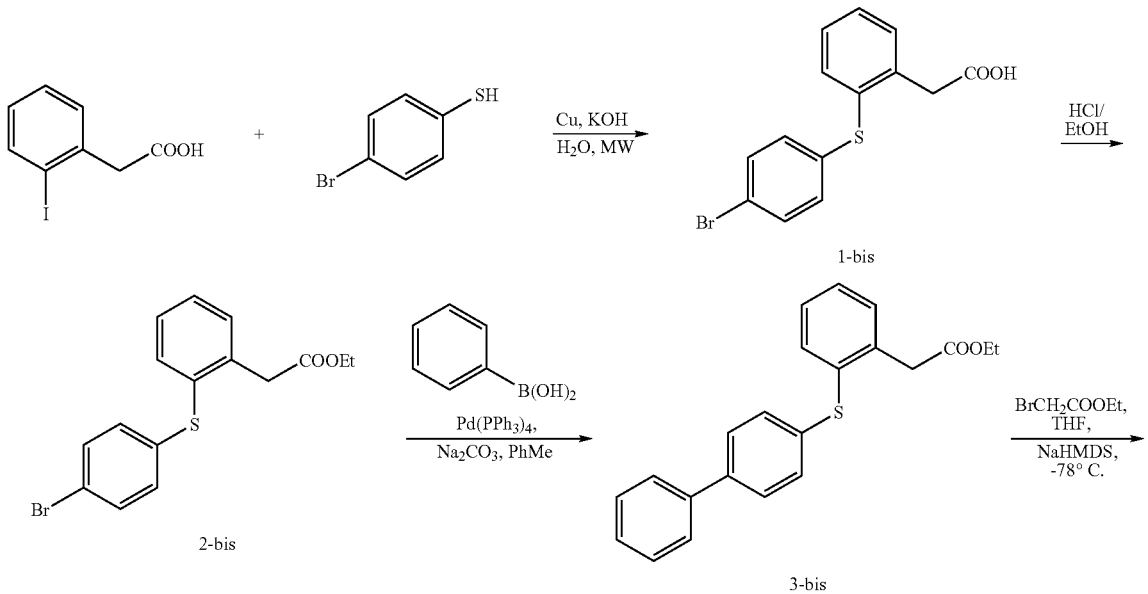

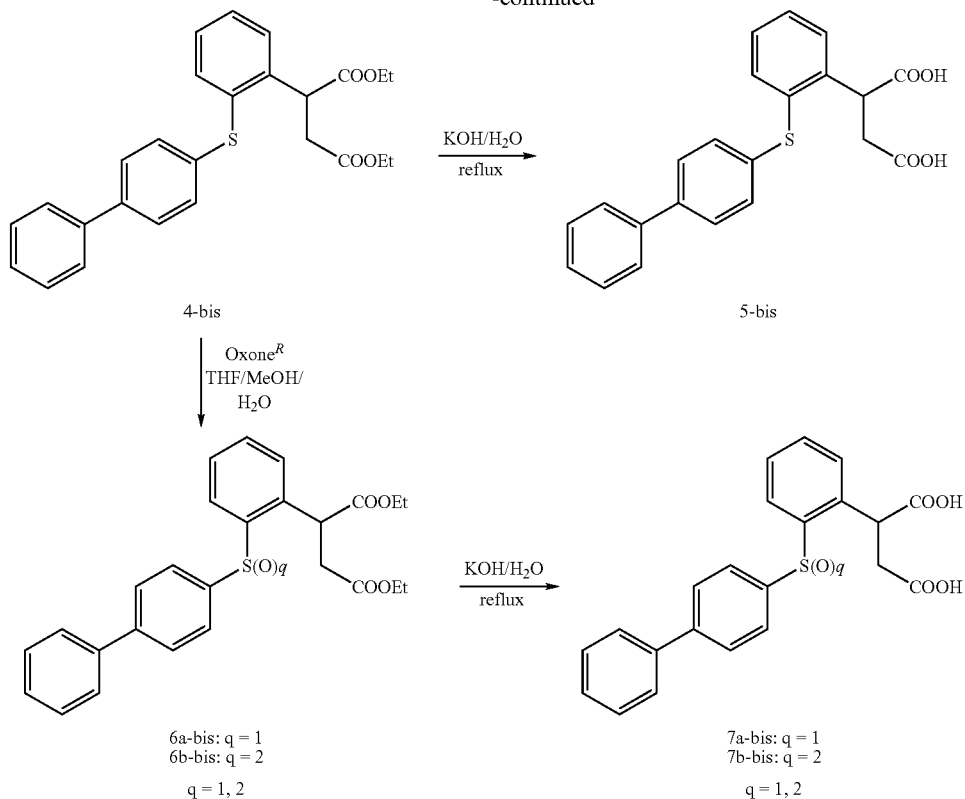

(1-bis) A suspension of 2-iodophenyl acetic acid (1 g, 3.82 mmol), 4-bromobenzenethiol (0.722 g, 3.82 mmol), KOH (0.427 g, 7.63 mmol) and copper powder (24 mg, 0.38 mmol) in 2 mL of water, was allowed to react in microwave (conditions: 2×6 min, 180 W, T max=100° C., P max=100 psi). The suspension obtained was dissolved in 2N aqueous solution of KOH and then filtered. The filtrate was acidified with 1N aq. HCl; the white precipitate was filtered, dried in vacuo, purified by trituration with acetone to give the pure acid 1-bis as white solid (1.16 g, 94%).

$^1$H-NMR (CDCl$_3$, 200 MHz): 7.44 (d, J=7 Hz, 1H); 7.36-7.26 (m, 5H); 7.01 (d, J=8.4 Hz, 2H); 3.86 (s, 2H).

Anal. Calcd. for C$_{14}$H$_{11}$BrO$_2$S (MW=323.2): C, 52.03; H, 3.43; Br, 24.72; O, 9.90; S, 9.92.

(2-bis) A solution of 1-bis (3 g, 9.28 mmol) in EtOH (30 ml) and 40% HCl ethanolic solution (20 ml) was refluxed for 3 h. The reaction mixture was allowed to reach room temperature, then poured into water (30 ml) and extracted with CH$_2$Cl$_2$. The extracts were combined, washed with water and brine; then dried (Na$_2$SO$_4$) and concentrated in vacuo. The crude product was purified by flash chromatography (hexane/EtOAc) to obtain the ethyl ester 2-bis as colourless oil (2.8 g, 86%).

$^1$H-NMR (CDCl$_3$, 200 MHz): 7.44-7.24 (m, 6H); 7.02 (m, 2H) 4.08 (q, J=7.1 Hz, 2H); 3.81 (s, 2H); 1.21 (t, J=7.1 Hz). Anal. Calcd for C$_{16}$H$_{15}$BrO$_2$S (MW=351.3): C, 54.71; H, 4.30; Br, 22.75; O, 9.11; S, 9.13.

(3-bis) In a two necked round bottom flask to a solution of 2-bis (2.65 g, 7.5 mmol) in toluene (14 ml) was added Pd(PPh$_3$)$_4$ (130 mg, 0.113 mmol) and the mixture stirred at room temperature for 10 min, then was added phenylboronic acid (1.1 g, 9 mmol) dissolved in toluene (6 ml) and aqueous solution of Na$_2$CO$_3$ (1.63 g in 6.5 ml water). The reaction mixture was refluxed 5 h, then allowed to warm to room temperature and neutralized with 1N HCl. The product was extracted with EtOAc. The organic phase was washed with water and brine, then dried (Na$_2$SO$_4$) and concentrated in vacuo. The crude product was purified by flash chromatography (hexane/EtOAc) to give compound 3-bis as white solid (2.27 g, 87%).

$^1$H-NMR (CDCl$_3$, 200 MHz): 7.57-7.22 (m, 13H); 4.1 (q, J=7.1 Hz, 2H); 3.87 (s, 2H); 1.21 (t, J=7.1 Hz, 6H). Anal. Calcd for C$_{22}$H$_{20}$O$_2$S (MW=348.5): C, 75.83; H, 5.79; O, 9.18; S, 9.20.

(4-bis) To a solution of 3-bis (200 mg, 0.574 mmol) in dry THF (3 ml) it was added dropwise 1M solution of NaHMDS (0.63 ml, 0.63 mmol) at −78° C. After 1 h stirring at −78° C. was added all at once BrCH$_2$COOEt (0.32 ml, 2.87 mmol). The mixture was stirred at −78° C. for 1 h and then 2 h at −40° C., then quenched with acetic acid (0.1 ml glacial acetic acid in 3 ml Et$_2$O) and filtered over Celite. The filtrate was concentrated and the resulting residue purified by flash chromatography (hexane/EtOAc) to give compound 4-bis as yellow oil (243 mg, 98%).

$^1$H-NMR (CDCl$_3$, 200 MHz): 7.57-7.23 (m, 13H); 4.12 (m, 4H) 3.10 (dd, J=9.9 Hz, 1H); 2.56 (dd, J=9.9 Hz, 1H); 1.20 (m, 6H). Anal. Calcd. for C$_{25}$H$_{25}$O$_4$S (MW=421.5): C, 71.23; H, 5.98; O, 15.18; S, 7.61.

(5-bis) An emulsion of diethyl ester 4-bis (745 mg, 1.71 mmol) and aqueous solution of KOH (962 mg, 17.1 mmol in 7 ml water) was refluxed for 15 h. The reaction mixture was allowed to warm to room temperature and then acidified with 1N aqueous solution of HCl. The product was extracted with ethyl acetate. The organic phase was washed with water, brine, then dried (Na$_2$SO$_4$) and concentrated in vacuo. The crude product was purified by trituration with CH$_2$Cl$_2$/Et$_2$O to give 5-bis as white solid (608 mg, 94%).

¹H-NMR ((CD₃)₂O, 200 MHz): 7.64 (m, 4H); 7.45 (m, 9H); 4.92 (dd, J=4.5 Hz, 10.2 Hz, 1H); 3.1 (dd, J=10.2 Hz, 1H); 2.54 (dd, J=4.4 Hz, 1H). ESI (+) 401 (M+Na) 100%; 417 (M+K). Anal. Calcd for C₂₂H₁₈O₄S (MW=378.4): C, 69.82; H, 4.79; O, 16.91; S, 8.47.

(6a-bis) To a solution of 4-bis (100 mg, 0.23 mmol) in MeOH/THF (1:1, 2.8 ml) it was added <Oxone>® (1.42 g, 2.3 mmol) and then water (5.6 ml). The reaction mixture was stirred at room temperature 1 day. The organic solvents were evaporated and the aqueous layer extracted with EtOAc. The organic phase was dried and evaporated in vacuo to give 6a-bis as colorless oil (51 mg, 49%).

¹H-NMR (CDCl₃, 200 MHz): 8.08 (d, J=7.7 Hz, 1H); 7.67 (q, J=8.6 Hz, 4H); 7.58-7.31 (m, 9H); 4.56 (dd, J=4, 11 Hz, 1H); 4.08 (m, 4H); 2.95 (dd, J=11 Hz, 1H); 1.84 (dd, J=4 Hz, 1H); 1.17 (t, J=7.2 Hz, 3H); 1.16 (t, J=7.2 Hz, 3H) API-EI(+) 473 (M+Na) 100%; 489 (M+K). Anal. Calcd for C₂₆H₂₆O₅S (MW=450.5): C, 69.31; H, 5.82; O, 17.76; S, 7.12.

(6b-bis) To a solution of 4-bis (100 mg, 0.23 mmol) in MeOH/THF (1:1, 5.6 ml) it was added <Oxone>® (2.83 g, 4.6 mmol) and then water (2.8 ml). The reaction mixture was stirred at room temperature 2 days. The organic solvents were evaporated and the aqueous layer extracted with EtOAc. The organic phase was dried and evaporated in vacuo to give 6b-bis as colorless oil (100 mg, 93%).

¹H-NMR (CDCl₃, 200 MHz): 8.36 (d, J=7.9, 1H); 8.01 (d, J=8.4, 2H); 7.74 (d, J=8.4, 2H); 7.61-7.38 (m, 8H); 5.01 (dd, J=3.3, 11 Hz, 1H); 4.16 (m, 2H); 3.92 (m, 2H); 2.96 (dd, J=11 Hz, 1H); 2.47 J=3.3 Hz, 1H); 1.23 (m, 6H). Anal. Calcd for C₂₆H₂₆O₆S (MW=466.1): C, 66.93; H, 5.92; O, 20.58; S, 6.87.

(7a-bis) An emulsion of 6a-bis (110 mg, 0.244 mmol) and 4 ml of aqueous solution of KOH (136.9 mg, 2.44 mmol) was refluxed for 15 h. The reaction mixture was allowed to warm to room temperature and then acidified with 1N aqueous solution of HCl. The white precipitate was filtered and washed with Et₂O to give the pure product 7a-bis as white solid (84 mg, 87%).

¹H-NMR (d₆-DMSO, 200 MHz): 12.55 (br s, OH); 7.89-7.67 (m, 7H); 7.52-7.37 (m, 6H); 4.55 (dm, 1H); 2.95 (m, 1H); 2.54 (m, 1H). ESI (+) 395 (M+1) 80%, 417 (M+Na) 100%; 433 (M+K) 20%. Anal. Calcd for C₂₂H₁₈O₅S (MW=394.4): C, 66.99; H, 4.60; O, 20.28; S, 8.13.

(7b-bis) An emulsion of 6b-bis (380 mg, 0.81 mmol) and 5 ml of aqueous solution of KOH (450 mg, 8.1 mmol) was refluxed for 15 h. The reaction mixture was allowed to warm to room temperature and then acidified with 1N aqueous solution of HCl. The precipitate was filtered and washed with Et₂O to give the pure product 7b-bis as white solid (322 mg, 96%).

¹H-NMR (d₆-DMSO, 200 MHz): 12.4 (br s, 1H); 8.2 (d, J=7.5 Hz, 1H); 7.9-7.2 (m, 12H); 4.85 (d, J=8 Hz, 10.8 Hz, 1H); 2.96 (dd, J=10.8 Hz, 1H); 1.89 (d, J=16.8 Hz, 1H). ESI (+) 433 (M+Na) 20%; 449 (M+K) 100%. Anal. Calcd for C₂₂H₁₈O₆S (MW=410.4): C, 69.38; H, 4.42; O, 23.39; S, 7.81.

EXAMPLE 23

Compounds (8-bis) and (10-bis)

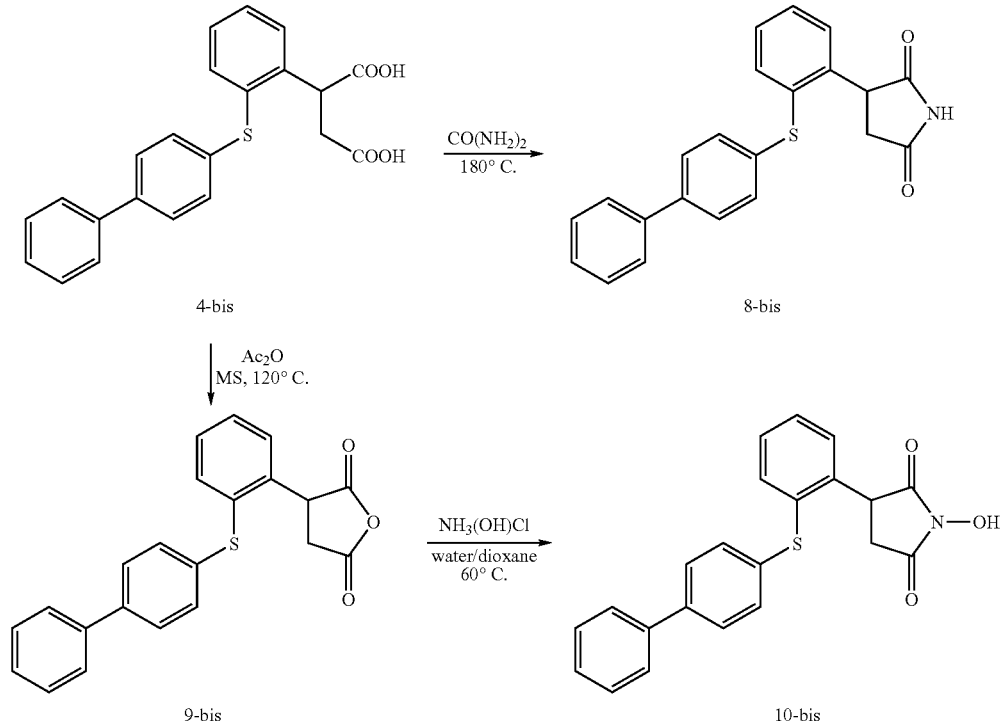

(8-bis) A mixture of urea (107 mg, 1.78 mmol) and acid 4-bis (150 mg, 0.396 mmol) in 0.5 ml toluene was stirred for 2 h at 180° C. After cooling the brown solid was purified by flash chromatography (CH₂Cl₂/MeOH) to afford the product as white foam in quantitative yield.

¹H-NMR (CDCl₃, 200 MHz): 8.15 (br s, 1H); 7.58-7.22 (m, 13H); 4.66 (dd, J=6 Hz, 9.8 Hz, 1H); 3.16 (dd, J=9.8 Hz); 2.73 (dd, J=6 Hz). ESI (+) 382 (M+Na) 100%. Anal. Calcd for $C_{22}H_{17}NO_2S$ (MW=359.4): C, 73.51; H, 4.77; N, 3.90; O, 8.90; S, 8.92.

(10-bis) A mixture of acid 4-bis (150 mg, 0.396 mmol), molecular sieves 4 Å (300 mg) and acetic anhydride (3 ml) was stirred at 120° C. for 15 h. The reaction mixture was filtered and the residue washed with EtOAc. The filtrate was concentrated to give the product 9 as white solid (105 mg, 74%). This obtained anhydride 9 (100 mg, 0.28 mmol) was added to a solution of hydroxylamine hydrochloride (21.4 mg, 0.308 mmol) and NaOH (12 mg) dissolved in 5 ml of water-dioxane (1:1). The solution was stirred for 15 min at room temperature and then 2 h at 60° C. The water and dioxane were evaporated under reduced pressure, and then heated at 145° C. for 5 min in vacuo. The product was extracted with EtOAc. The extracts were combined and evaporated. The product was washed with $Et_2O$ and dried in vacuo, then purified by flash chromatography ($CH_2Cl_2$/MeOH) to obtain 10-bis as a white foam (65 mg, 62%).

$^1$H-NMR (200 MHz, $CDCl_3$): 7.56-7.20 (m, 13H); 4.57 (dd, J=4.76 Hz, 9.16 Hz, 1H); 3.10 (dd, J=9.16 Hz); 2.61 (dd, J=4.76 Hz). ESI (+) 398 (M+Na) 100%, 414 (M+K) 20%. Anal. Calcd for $C_{22}H_{17}NO_3S$ (MW=375.4): C, 70.38; H, 4.56; N, 3.73; O, 12.78; S, 8.54.

EXAMPLE 24

Compounds (11-bis) and (13-bis)

(11-bis) A mixture of urea (53 mg, 1.22 mmol) and acid 7b-bis (100 mg, 0.245 mmol) in 0.3 ml of toluene was stirred for 2 h at 180° C. After cooling the brown solid was purified by flash chromatography (EtOAc/hexane) to afford 11-bis as white foam (75 mg, 78%).

$^1$H-NMR (200 MHz, $CDCl_3$): 8.2-7.31 (m, 13H); 8.13 (br s, NH); 5.17 (dd, J=6 Hz, 9.7 Hz, 1H); 3.32 (dd, J=9.7 Hz) 2.67 (dd, J=6 Hz). ESI (+) 414 (M+Na) 100%, 430 (M+K) 60%. Anal. Calcd for $C_{22}H_{17}NO_2S$ (MW=359.4): C, 73.51; H, 4.77; N, 3.90; O, 8.90; S, 8.92.

(13-bis) A mixture of 7b-bis (120 mg, 0.292 mmol), molecular sieves 4 Å (250 mg) and acetic anhydride (2.3 ml) was stirred at 120° C. for 15 h. The reaction mixture was filtered and the residue washed with EtOAc. The filtrate was concentrated to give the product as white solid (75 mg, 66%). This obtained anhydride 12-bis (70 mg, 0.187 mmol) was added to a solution of hydroxylamine hydrochloride (15.0, 0.214 mmol) and NaOH (8 mg) dissolved in 4 ml of water-dioxane (1:1). The solution was stirred for 15 min at room temperature and then 2 h at 60° C. The water and dioxane were evaporated under reduced pressure, the residue was heated at 145° C. for 5 min in vacuo. The product was extracted with EtOAc. The extracts were combined, dried and evaporated. The product was washed with $Et_2O$, dried in vacuo and purified by flash chromatography ($CH_2Cl_2$/MeOH) to obtain 13-bis as a white foam (20 mg, 26%).

$^1$H-NMR (200 MHz, $CDCl_3$): 8.13-7.45 (m, 13H); 5.07 (br s, 1H); 3.14 (m, 1H) 2.48 (m, 1H). ESI (+) 430 (M+Na) 100%.

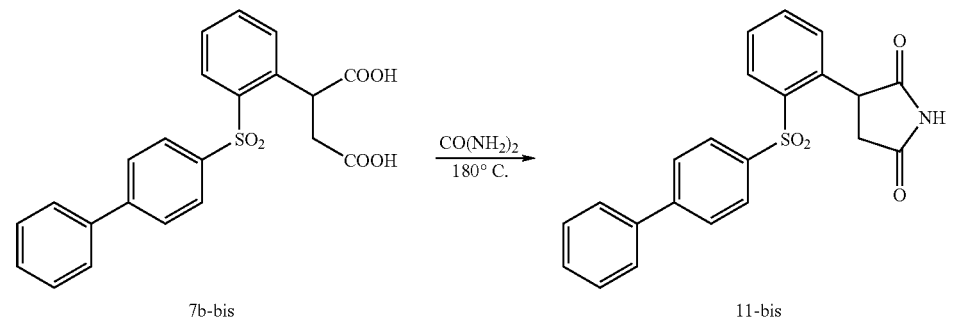

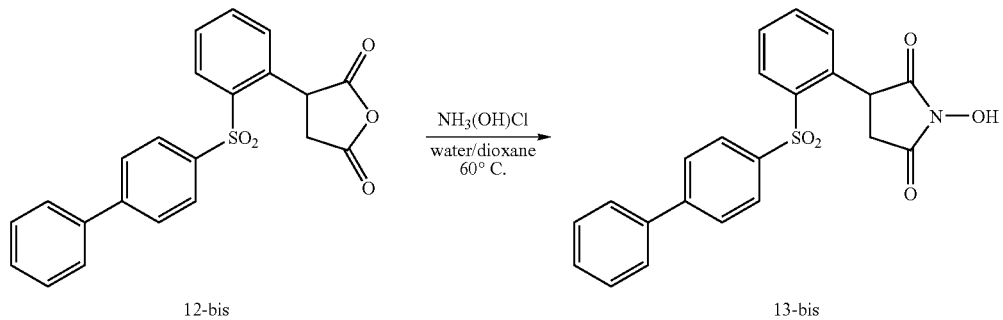

Anal. Calcd for $C_{22}H_{17}NO_5S$ (MW=407.4): C, 64.85; H, 4.21; N, 3.44; O, 19.63; S, 7.87.

EXAMPLE 25

Compounds 15-bis, 17a-bis, 17b-bis

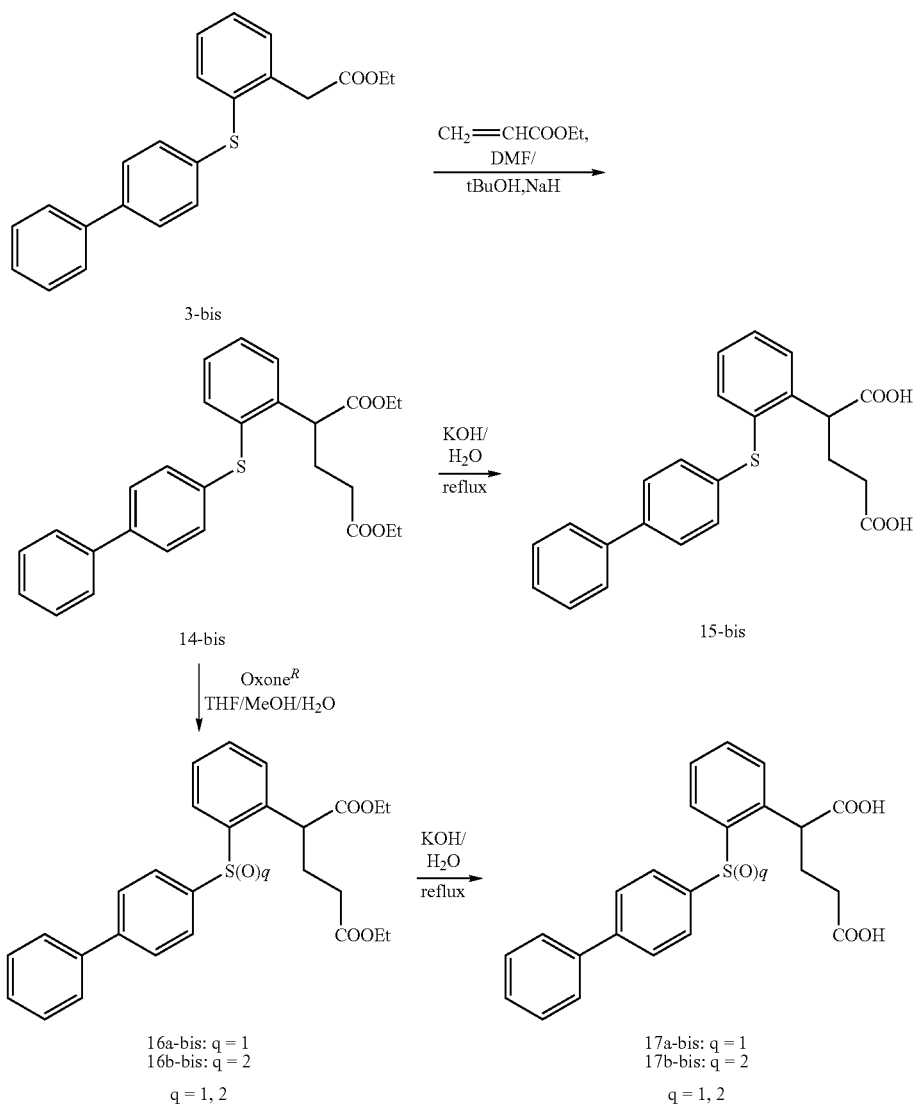

(14-bis) Ethyl acrylate (186 µl, 1.86 mmol) was added to a solution of 3-bis (500 mg, 1.43 mmol) in tBuOH/DMF (4:1, 7.5 ml) cooled in a cold water bath (5° C.) and treated with NaH (24 mg, 1 mmol). The mixture was stirred at 5° C. for 15 min and then 2 h at room temperature, then 0.5 ml of glacial acetic acid were added. The organic products were extracted into ether and washed with water (4×), saturated aq. $NaHCO_3$ solution and brine. The organic phase was dried ($Na_2SO_4$) and concentrated, then the crude product purified by flash chromatography (hexane/EtOAc) to obtain compound 14-bis as white oil (822 mg, 64%).

$^1$H-NMR (CDCl$_3$, 200 MHz): 7.55-7.19 (m, 13H); 4.45 (t, 1H, J=7.2 Hz); 4.04 (q, J=7.4 Hz, 4H); 2.45-1.96 (m, 4H); 1.15 (t, J=7.2 Hz, 6H).

Anal. Calcd for $C_{27}H_{28}O_4S$ (MW=448.6): C, 72.29; H, 6.29; O, 14.27; S, 7.15.

(15-bis) An emulsion of diethyl ester 14-bis (140 mg, 0.31 mmol) and aq. solution of KOH (261 mg, 4.65 mmol in 7 ml water) was refluxed for 40 h. The reaction mixture was allowed to warm to room temperature and then acidified with 1N aq. HCl. The white precipitate was filtered and washed with water, then purified by trituration with DCM/hexane to give acid 15-bis as white solid (95 mg, 79%).

$^1$H-NMR (d$_6$-DMSO, 200 MHz): 12.29 (br s, 1H); 7.66-7.61 (m, 4H); 7.49-7.27 (m, 9H); 4.26 (t, J=7.4 Hz, 1H); 2.15 (m, 3H); 1.89 (m, 1H). Anal. Calcd for $C_{23}H_{20}O_4S$ (MW=392.5): C, 70.39; H, 5.14; O, 16.31; S, 8.17.

(16a-bis) To a solution of 14-bis (230 mg, 0.49 mmol) in MeOH/THF (1:1, 5 ml) was added <Oxone>® (3.04 g, 4.94 mmol) and then water (20 ml). The reaction mixture was stirred at room temperature for 7 h. The organic solvents were evaporated and the aqueous layer extracted with EtOAc. The organic phase was dried and evaporated in vacuo and purified by flash chromatography to give 16a-bis as colorless oil (100 mg, 42%).

$^1$H-NMR (CDCl$_3$, 200 MHz): 7.97 (m, 1H); 7.75-7.62 (m, 4H); 7.57-7.37 (m, 8H); 4.35 (t, J=6.8 Hz, 1H); 4.27-3.89 (m, 4H); 2.52-2.06 (m, 4H); 1.26 (t, J=7 Hz, 6H). Anal. Calcd for C$_{27}$H$_2$O$_5$S (MW=464.6): C, 69.80; H, 6.07; O, 17.22; S, 6.90.

(16b-bis) To a solution of 14bis (100 mg, 0.22 mmol) in MeOH:THF (1:1, 6 ml) was added <Oxone>® (2.74 g, 4.45 mmol) and then water (2 ml). The reaction mixture was stirred at room temperature for 2 days. The organic solvents were evaporated and the aqueous layer extracted with EtOAc. The organic phase was dried, evaporated in vacuo and purified by flash chromatography (hexane/EtOAc) to give 16b-bis as yellow oil (80 mg, 75%).

$^1$H-NMR (CDCl$_3$, 200 MHz): 8.30 (dd, J=6.6, 1.4 Hz, 1H); 7.91 (dt, J=8.6, 2.0 Hz, 2H); 7.69 (dt, J=8.8, 1.8 Hz, 2H); 7.65-7.37 (m, 8H); 4.65 (t, J=7.2 Hz, 1H); 4.05 (q, J=7.2 Hz, 2H); 3.84 (m, 2H); 2.44-2.21 (m, 2H); 2.18-1.81 (m, 2H); 1.19 (t, J=7.2 Hz, 3H); 0.92 (t, J=7.2 Hz, 3H). Anal. Calcd for C$_{27}$H$_{28}$O$_6$S (MW=480.6): C, 67.48; H, 5.87; O, 19.98; S, 6.67.

(17a-bis) To a solution of 16a-bis (100 mg, 0.215 mmol) in THF (0.5 ml) was added 5 ml of an aqueous solution of KOH (136.9 mg, 2.44 mmol) and the mixture was refluxed 20 h. Then the reaction solution was allowed to warm to room temperature and acidified with 1N aq. HCl. The precipitate was filtered, washed with H$_2$O and purified by trituration (acetone/hexane) to give the pure product 17a-bis as white solid (67 mg, 76%).

$^1$H-NMR (d$_6$-DMSO, 200 MHz): 12.45 (br s, 2H); 7.86-7.32 (m, 13H); 4.28 (dm, 1H); 2.4-1.56 (m, 4H). Anal. Calcd for C$_{23}$H$_{20}$O$_5$S (MW=408.5): C, 67.63; H, 4.94; O, 19.58; S, 7.85.

(17b-bis) A mixture of 16b-bis (80 mg, 0.195 mmol) dissolved in 0.5 ml THF and 5 ml of an aqueous solution of KOH (109 mg, 1.95 mmol) was refluxed for 24 h. The reaction mixture was allowed to warm to room temperature and then acidified with 1N aq. HCl. The precipitate was filtered, washed with H$_2$O and triturated (Et$_2$O/CH$_2$Cl$_2$/hexane) to give the pure product 17b-bis as white solid (43 mg, 60%).

$^1$H-NMR (d$_6$-DMSO, 200 MHz): 12.24 (br s, 2H); 8.2 (d, J=7.8 Hz, 1H); 7.9 (m, 4H); 7.77-7.47 (m, 8H); 4.47 (d, J=6.8, 10.8 Hz, 1H); 2.11-1.51 (m, 4H). Anal. Calcd for C$_{23}$H$_{20}$O$_6$S (MW=424.5): C, 65.08; H, 4.75; O, 22.62; S, 7.55.

EXAMPLE 26

Compounds (20-bis), (22-bis) and (23-bis)

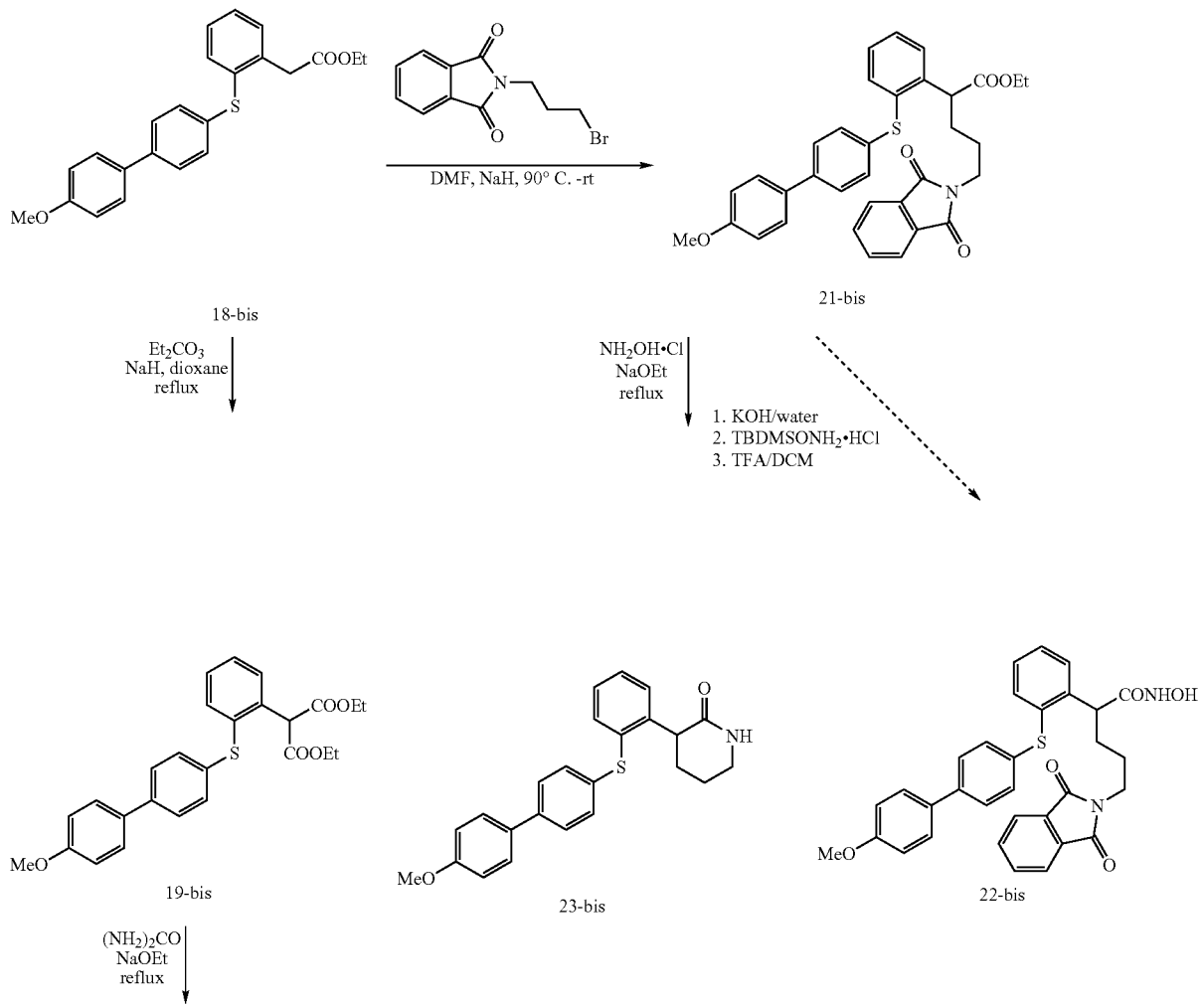

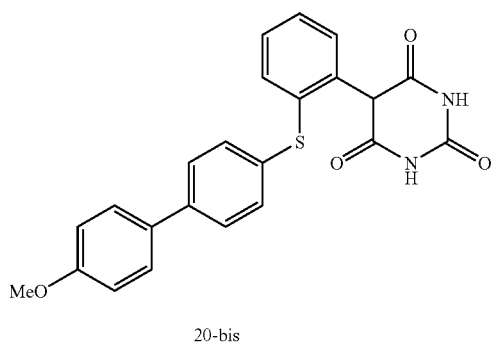

20-bis (18-bis) Compound 18-bis was synthesized following an analogous procedure to that described for the preparation of 3-bis in Example 22, starting from compound 2-bis and using p-methoxyphenylboronic acid.

$^1$H-NMR (CDCl$_3$, 200 MHz): 7.5-7.2 (m, 10H); 6.96 (d, J=9 Hz, 2H); 4.1 (q, J=7 Hz, 2H); 3.86 (s, 2H); 3.84 (s, 3H); 1.21 (t, J=7. Hz, 3H). Anal. Calcd for C$_{23}$H$_{22}$O$_3$S (MW=378.5): C, 72.99; H, 5.86; O, 12.68; S, 8.47.

(19-bis) A suspension of NaH (60% suspension in paraffin oil, 25 mg, 1.04 mmol) and diethyl carbonate (430 ml, 3.64 mmol) in absolute dioxane (1.5 ml) was heated to 100-110° C., and a solution of ethyl ester 18-bis (120 mg, 0.26 mmol) in dioxane (1 ml) was added dropwise. Stirring was continued for 24 h at 100° C. and then for 3 days at room temperature. The mixture was poured onto ice water and extracted with diethyl ether. The combined organic layers were washed with water and brine, dried (Na$_2$SO$_4$), and concentrated. The resulting residue was purified by flash chromatography (hexane/EtOAc) to obtain malonic ester 19-bis as a white oil (65 mg, 56%).

$^1$H-NMR (CDCl$_3$, 200 MHz): 7.6-7.26 (m, 8H); 7.18 (d, J=7.2 Hz, 2H); 6.96 (d, J=7.6 Hz, 2H); 5.53 (s, 1H); 4.12 (m, 4H); 3.84 (s, 1H); 1.20 (t, J=7.2 Hz, 6H). Anal. Calcd for C$_{25}$H$_{25}$O$_5$S (MW=450.5): C, 69.31; H, 5.82; O, 17.76; S, 7.12.

(20-bis) Sodium (6.2 mg, 0.27 mmol) was dissolved in ethanol (6 ml) and urea (14 mg, 0.27 mmol) was added to this solution. A solution of malonic ester 19-bis (60 mg, 0.13 mmol) in ethanol (1 ml) was added dropwise and the reaction mixture was refluxed for 6 h. After being cooled at room temperature, the mixture was poured into ice water and adjusted to pH 2, using diluted HCl. The precipitate was collected by suction filtration and dried in vacuo. The crude product was purified by trituration with diethyl ether. The product 20-bis was obtained as an amorphous white solid (43 mg, 76%).

$^1$H-NMR (d$_6$-DMSO, 200M Hz): 7.58 (d, J=8 Hz, 4H); 7.34 (m, 4H); 7.22 (d, J=8.2 Hz, 2H); 7.0 (d, J=8.2 Hz, 2H); 3.78 (s, 3H); 3.76 (s, 1H).

ESI (−): (M-H)$^−$ 417.4.

Anal. Calcd for C$_{23}$H$_{18}$N$_2$O$_4$S (MW=418.5): C, 66.01; H, 4.34; N, 6.68; O, 15.29; S, 7.66.

(21-bis) To a solution of ester 18-bis (111 mg, 0.24 mmol) in dry DMF (2 ml) was added NaH (23 mg, 0.95 mmol). The yellow suspension was heated at 90° C. for 30 min and then added with N-(3-bromopropyl)phthalimide (128 mg, 0.48 mmol) dissolved in DMF (1 ml). The mixture was refluxed for 30 min, then allowed to rich room temperature and stirred 2 days. EtOAc was added and the organic phase washed with sat. NH$_4$Cl solution and water, dried (Na$_2$SO$_4$), concentrated and purified by chromatography (EtOAc/hexane). The compound 21-bis was obtained as a colorless oil (100 mg, 74%).

$^1$H-NMR (CDCl$_3$, 200 MHz): 7.77 (m, 2H); 7.68 (m, 2H); 7.48-7.24 (m, 8H); 7.2 (d, J=8.8 Hz, 2H); 6.96 (d, J=8.8 Hz, 2H); 4.43 (t, J=7.4 Hz, 1H); 4.02 (m, 2H); 3.84 (s, 3H); 3.64 (t, J=6.8 Hz); 2.09 (m, 1H); 1.72 (m, 3H); 1.11 (t, J=8 Hz, 3H).

Anal. Calcd for C$_{34}$H$_{31}$NO$_5$S (MW=565.7): C, 72.19; H, 5.52; N, 2.48; O, 14.14; S, 5.67.

(23-bis) Sodium (8.5 mg, 0.37 mmol) was dissolved in ethanol (1 ml) and hydroxylamine hydrochloride (17.2 mg, 0.247 mmol) was added to this solution. A solution of ethyl ester 21-bis (70 mg, 0.124 mmol) in ethanol (1 ml) was added dropwise and the reaction mixture was refluxed for 20 h. After being cooled to room temperature, the mixture was poured into ice water and acidified with diluted HCl. The precipitate was collected by suction filtration and dried in vacuo. The crude product was purified by trituration with diethyl ether/hexane. The product 23-bis was obtained as a white solid (40 mg, 83%).

$^1$H-NMR (CDCl$_3$, 200 MHz): 7.53-7.17 (m, 10H); 6.97 (d, J=8.6 Hz, 2H); 6.18 (s, 1H); 4.2 (m, 1H); 3.84 (s, 3H); 3.43 (m, 2H); 2.1-1.83 (m, 4H).

Anal. Calcd for C$_{24}$H$_{23}$NO$_2$S (MW=389.5): C, 74.00; H, 5.95; N, 3.60; O, 8.22; S, 8.23.

(22-bis) The hydroxamic acid 22-bis can be easily prepared from compound 21-bis according to the procedure reported for the preparation of compound 56a (Example 18).

EXAMPLE 27

Preparation of Compounds (10a-ter) and (10b-ter)

The numbering of the compounds per the scheme below are conveniently identified, in the subsequent experimental section, with those same numbers plus "-ter" so as to avoid ambiguity with any previously prepared compound.

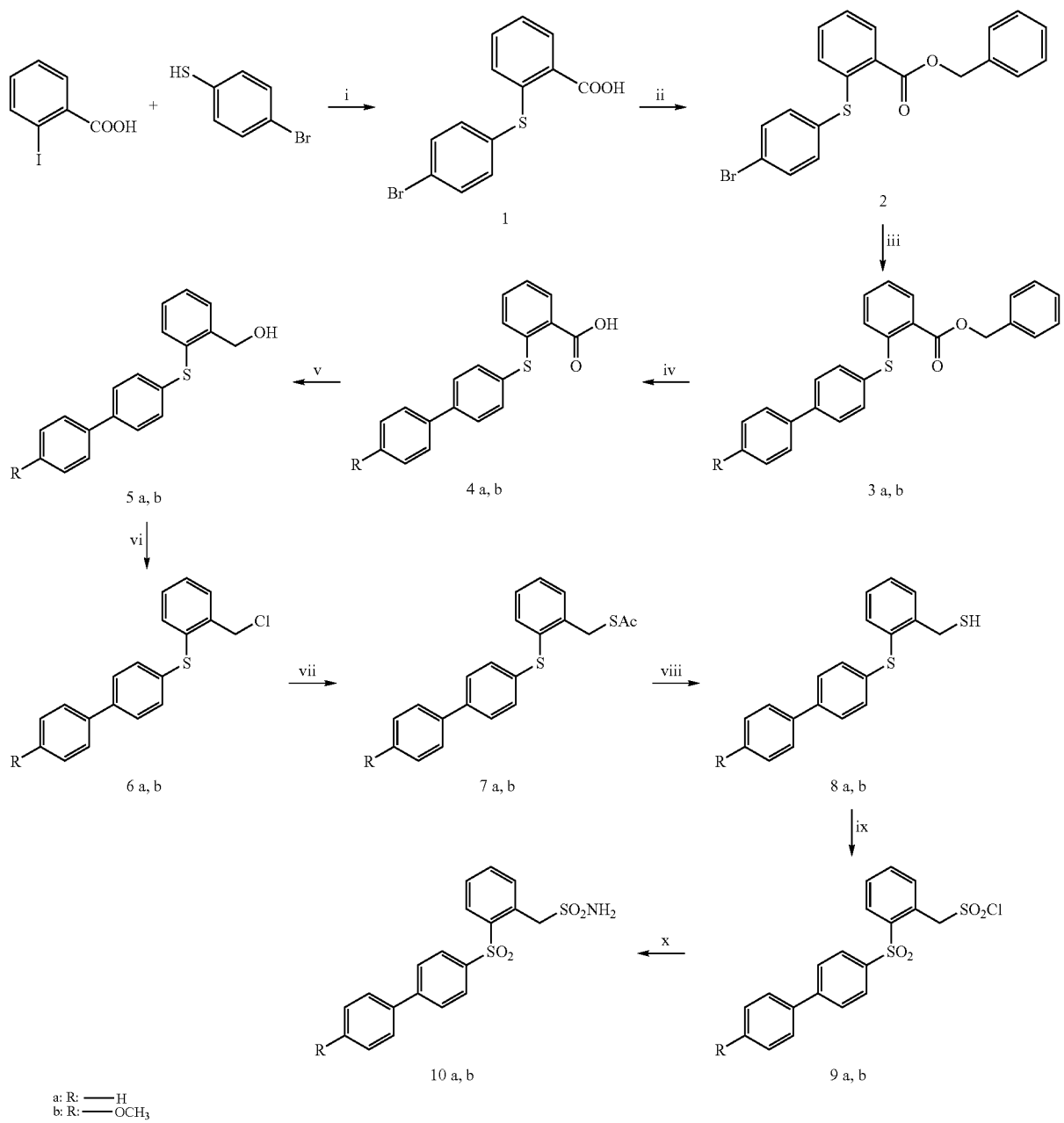

a: R: —H
b: R: —OCH₃

Reagents and conditions: i: KOH, Cu, H₂O, MW (180 W, 6', 140° C.). ii: 1) Cs₂CO₃, DMF., 0° C., 30'. 2) BnBr, 0° C., 30', rt, 20 h. iii: a) Phenyl boronic acid b) 4-methoxyphenyl boronic acid; Pd(PPh₃)₄, K₃PO₄, dioxane, H₂O, 85° C., 16 h. iv: KOH, H₂O, reflux, 16 h. v: 1) BH₃.THF 1M, 0°, 16 h; 2) MeOH, rt, 3 h vi: SOCl₂, CH₂Cl₂, Py, rt, 1 h. vii: AcSK, EtOH, reflux, 4 h. viii: KOH, H₂O, EtOH, reflux, 30'. ix: H₂SO₄, NaClO 13%, 0°, 30'. x: NH₃ $_{aq}$, CH₃CN, 0° to rt, 10'.

(1-ter) A suspension of 2-iodobenzoic acid (1.00 g, 4.03 mmol), 4-bromobenzenethiol (762 mg, 4.03 mmol), KOH (451.36 mg, 8.06 mol), Cu powder (25.6 mg, 0.40 mmol), in 2 ml of water was irradiated at the microwave (MW conditions: 2×6', 180 W, Tmax=100° C., Pmax=100 psi). The suspension was then diluted with water, basified with KOH, and filtered under vacuum. The filtrate was acidified with HCl 1 N and filtered again to give 1-ter as a white solid (1.11 g, y: 88.9%).

$^1$H-NMR (DMSO-d₆) δ: 6.75-6.79 (m, 1H); 7.19-7.27 (m, 1H); 7.35-7.49 (m, 3H); 7.65-7.70 (m, 2H); 7.89-7.93 (m, 1H); 13.25 (s, 1H).

(2-ter) To a solution of 1-ter (6.37 g, 20.59 mmol) in dry DMF (61.2 ml) under N₂ atmosphere at 0° C., Cs₂CO₃ (6.71 g, 20.59 mmol) was added, and the solution was stirred for 30', then BnBr (2.45 ml, 20.59 mmol) was added. The reaction mixture was kept at 0° C. for 30' and at room temperature for 20 h. The reaction was quenched with water and the product was extracted twice with diethyl ether. The combined organic layers were washed twice with water and once with brine, dried over Na₂SO₄ and evaporated in vacuo to give 2-ter as a white solid (8.27 g, y: quantitative).

$^1$H-NMR (CDCl$_3$) δ: 5.39 (s, 2H); 6.81-6.86 (m, 1H); 7.10-7.18 (m, 1H); 7.23-7.57 (m, 10H); 7.99-8.04 (m, 1H).

(3a-ter) Pd(PPh$_3$)$_4$ (716.5 mg, 3%) was added to a solution of 2-ter (8.27 g, 20.68 mmol) in water (45 ml) and dry dioxane (207 ml), with phenyl boronic acid (22.75 mmol) and K$_3$PO$_4$ (10 g, 47.56 mmol). The reaction mixture was stirred under N$_2$ atmosphere at 85° C. overnight, and then was cooled at room temperature and quenched with NaHCO$_3$. The product was extracted with AcOEt and the combined organic phases were dried on Na$_2$SO$_4$ and evaporated to give a crude product.

The brown oil was purified by a flash chromatography (n-Hexane 4: CH$_2$Cl$_2$ 1) to give 1.90 g of 3a-ter as a white solid (y: 28.5%).

$^1$H-NMR (CDCl$_3$) δ: 5.41 (s, 2H); 6.89-6.94 (m, 1H); 7.09-7.17 (m, 1H); 7.23-7.51 (m, 9H); 7.59-7.69 (m, 6H); 8.01-8.05 (m, 1H).

(3b-ter) By working analogously to what above reported for the preparation of 3a-ter, and by using 4-methoxyphenyl boronic acid (22.75 mmol) in place of phenyl boronic acid, a crude was obtained that was then purified by flash chromatography (n-Hexane 18: AcOEt 1) to give 3b-ter as a white solid (y: 75%).

$^1$H-NMR (CDCl$_3$) δ: 3.86 (s, 3H); 5.41 (s, 2H); 6.88-6.92 (m, 1H); 6.98-7.02 (m, 2H); 7.08-7.15 (m, 1H); 7.22-7.60 (m, 12H); 8.01-8.05 (m, 1H).

(4a-ter, 4b-ter) A suspension of 3a-ter (or 3b-ter) (6.5 mmol) and KOH (1.01 g, 19.53 mmol) in water (27.5 ml) was heated at reflux overnight. The reaction mixture was cooled, acidified with HCl 1N and extracted with CH$_2$Cl$_2$. The solvent was evaporated and the pure compounds were obtained by trituration with diethyl ether: (4a-ter) (y: 78%)

$^1$H-NMR (DMSO-d$_6$) δ: 6.82-6.86 (m, 1H); 7.19-7.63 (m, 8H); 7.72-7.82 (m, 4H); 7.91-7.95 (m, 1H).

(4b-ter) as a white solid (y: 60%)

$^1$H-NMR (DMSO-d$_6$) δ: 3.81 (s, 3H); 6.80-6.84 (m, 1H); 7.03-7.07 (m, 2H); 7.17-7.25 (m, 1H); 7.35-7.43 (m, 1H); 7.55-7.59 (m, 2H); 7.66-7.77 (m, 4H); 7.89-7.93 (m, 1H).

(5a-ter, 5b-ter) Under nitrogen atmosphere at 0° C., BH$_3$-THF 1M (3.86 ml) was added to the acid 4a-ter (or 4b-ter) (3.86 mmol) and the solution was stirred at room temperature for 16 h. The reaction was quenched with MeOH, stirred for 3 h, then solvents were evaporated, CH$_2$Cl$_2$ was added and the reaction mixture was washed with NaHCO$_3$. The product was finally extracted with CH$_2$Cl$_2$.

(5a-ter) as a white solid (y: 80.9%)

$^1$H-NMR (CDCl$_3$) δ: 4.79 (s, 2H); 7.22-7.55 (m, 13H).

(5b-ter) as a white solid (y: 70%)

$^1$H-NMR (CDCl$_3$) δ: 3.85 (s, 3H); 4.82 (s, 2H); 6.94-6.98 (m, 2H); 7.24-7.54 (m, 10H).

(6a-ter, 6b-ter) The alcohol 5a-ter (or 5b-ter) (2.67 mmol) was dissolved under N$_2$ atmosphere in dry CH$_2$Cl$_2$ (14 ml), thionyl chloride (0.25 ml, 3.47 mmol) and pyridine (a drop) were added to the solution. The reaction was stirred for 1 h, then was quenched with water, and extracted with Et$_2$O. The organic layers were washed twice with brine, dried over Na$_2$SO$_4$, and evaporated in vacuo.

(6a-ter) as a white solid (y: 91%)

$^1$H-NMR (CDCl$_3$) δ: 4.74 (s, 2H); 7.17-7.50 (m, 13H).

(6b-ter) as a white solid (y: 89%)

$^1$H-NMR (CDCl$_3$) δ: 3.85 (s, 3H); 4.82 (s, 2H); 6.95-6.99 (m, 2H); 7.29-7.34 (m, 5H); 7.45-7.54 (m, 5H).

(7a-ter, 7b-ter) Compound 6a-ter (or 6b-ter) (1.49 mmol) was dissolved in dry EtOH (15.33 ml) and KSAc (547 mg, 4.79 mmol) was added. The reaction mixture was heated at 85° C. under reflux for 4 h. The solution was cooled and quenched with NaHCO$_3$, and the suspension was extracted with AcOEt. The organic layers were then washed with NaHCO$_3$ and water, dried over Na$_2$SO$_4$ and evaporated in vacuo.

(7a-ter) as a yellow oil (y: 85%)

$^1$H-NMR (CDCl$_3$) δ: 2.32 (s, 3H); 4.32 (s, 2H); 7.25-7.59 (m, 13H).

(7b-ter) as a light yellow solid (y: 96%)

$^1$H-NMR (CDCl$_3$) δ: 2.32 (s, 3H); 3.85 (s, 3H); 4.31 (s, 2H); 6.93-7.00 (m, 2H); 7.19-7.36 (m, 5H); 7.43-7.54 (m, 5H).

(8a-ter, 8b-ter) A solution of EtOH (3.9 ml) and water (3.9 ml) was purged with N$_2$ for 40', and then KOH (260 mg, 4.62 mmol) was added. The solution was purged again with N$_2$ for 20', then compound 7a-ter (or 7b-ter) (0.483 mmol) was added and the solution was purged again with N$_2$ for 10'. The reaction mixture was heated at reflux under N$_2$ for 30' and then was carefully neutralized with HCl 1N. The product was extracted with CH$_2$Cl$_2$ and the solvent was evaporated to give the desired thiol.

(8a-ter) as a brown oil (y: 95%)

$^1$H-NMR (CDCl$_3$) δ: 3.96 (s, 2H); 7.19-7.89 (m, 13H).

(8b-ter) The crude product (yellow solid) was purified by flash chromatography (n-Hexane 7: CH$_2$Cl$_2$ 2) to give a white solid (y: 18%).

$^1$H-NMR (CDCl$_3$) δ: 3.84 (s, 3H); 3.96 (s, 2H); 6.93-6.97 (m, 2H); 7.20-7.30 (m, 5H); 7.43-7.56 (m, 5H).

(9a-ter, 9b-ter) Thiol 8a-ter (or 8b-ter) (0.34 mmol) was added to H$_2$SO$_4$ (1 ml) and was cooled to 0° C. NaClO 13% (2.12 ml, 3.4 mmol) was added dropwise and the reaction was stirred at 0° C. for 30'. The solution was diluted with water, CH$_2$Cl$_2$ was added and the layers were separated. The aqueous layer was extracted twice with CH$_2$Cl$_2$, the organic ones were combined, dried over Na$_2$SO$_4$, and evaporated to give, as crude product, 9a-ter as a yellow solid (or 9b-ter as a brown oil).

(10a-ter, 10b-ter) To a cooled solution of 9a-ter (or 9b-ter) (0.29 mmol) in acetonitrile (0.03 ml), NH$_3$ $_{(aq)}$ (0.1 ml) was added dropwise over a period of 3' at 0° C. The resulting mixture was stirred at room temperature for 10'. The reaction mixture was extracted with CHCl$_3$ and the organic layers were dried over Na$_2$SO$_4$ and concentrated in vacuo.

(10a-ter) The crude product was purified by flash chromatography (n-Hexane 3: AcOEt 2) and it was triturated with n-hexane and diethyl ether to obtain a light brown solid (y: 4%).

$^1$H-NMR [(CD$_3$)$_2$CO-d$_6$)] δ: 4.96 (s, 2H); 6.13 (s, 2H); 7.44-7.55 (m, 3H); 7.62-7.81 (m, 5H); 7.88-7.92 (m, 2H); 8.01-8.09 (m, 2H); 8.18-8.21 (m, 1H).

Analysis Calculated for C$_{19}$H$_{17}$NO$_4$S$_2$ (MW: 387.47): C, 58.90; H, 4.42; N, 3.61; O, 16.52; S, 16.55.

(10b-ter) The crude product was purified by flash chromatography (n-Hexane 1: AcOEt 1) to give a brown solid (y: 10.6%).

$^1$H-NMR [(CD$_3$)$_2$CO-d$_6$)] δ: 3.85 (s, 3H); 4.95 (s, 2H); 6.14 (s, 2H); 7.03-7.08 (m, 1H); 7.23-7.27 (m, 1H); 7.67-7.91 (m, 5H); 8.00-8.06 (m, 3H).

Analysis Calculated for C$_{20}$H$_{19}$NO$_5$S$_2$ (MW: 417.5): C, 57.54; H, 4.59; N, 3.35; O, 19.16; S, 15.36.

EXAMPLE 28

Analysis of the In Vitro Inhibition Activity of Zinc Metalloproteinases: In Vitro Inhibition of MMMPs The human recombinant Progelatinase A (pro-MMP-2), B (pro-MMP-9), MMP-14cd and MMP-16cd, were provided by Prof. Gillian Murphy (Oncology Department, Cambridge University, UK); pro-MMP-1, pro-MMP-3, pro-MMP-7, pro-MMP-8, pro-MMP-13 and pro-MMP-14 were bought from Calbiochem. The proenzymes were activated immediately before the use with p-aminophenylmercuric acetate (APMA 2 mM for 1 h at 37° C. for MMP-1, MMP-2 and MMP-8, 1 mM for 1 h at 37° C. for MMP-9 and MMP-7, 1 mM for 30 min at 37° C. for MMP-13). Pro-MMP-14 and pro-MMP-3 were activated with trypsin 5 µg/ml for 15 min at 37° C. followed the soybean trypsin inhibitor (SBTI) 23 µg/ml for pro-MMP-14 and 62 µg/ml for pro-MMP-3. The catalytic domains of MMP-14 and MMP-16 were utilized without activation.

For the assay measurements, the stock solutions of the inhibitor (DMSO, 100 mM) were further diluted up to 7 different concentrations (0.01 nM-300 µM) for each MMP, in the buffer for the fluorometric assay (FAB: Tris 50 mM, pH=7.5, NaCl 150 mM, $CaCl_2$ 10 mM, Brij 35 0.05% and DMSO 1%). The solutions of activated enzyme (final concentrations 2.9 nM for MMP-2, 2.7 nM for MMP-9, 2.4 nM for MMP-7, 1 nM for MMP-14 and MMP-3, 1.5 nM for MMP-8 and MMP-16cd, 0.84 nM for MMP-14cd, 0.66 nM for MMP-13 and 0.20 nM for MMP-1) and of inhibitor were incubated in the assay buffer for 4 h at 25° C. After the addition of solution of fluorogenic substrate 200 µM Mca-Arg-Pro-Lys-Pro-Val-Glu-Nva-Trp-Arg-Lys(Dnp)-NH2 (Sigma) for MMP-3 and Mca-Lys-Pro-Leu-Gly-Leu-Dpa-Ala-Arg-$NH_2$ (Bachem) for all the other enzymes in DMSO (final concentration 2 µM), the hydrolysis were monitored every 15 sec for 20 min, recording the increase in fluorescence ($\lambda_{ex}$=325 nm, $\lambda_{em}$=400 nm) with a Molecular Device SpectraMax Gemini XS plates reader. The assays were made in triplicate in a total volume of 200 µl per well on 96 well-plates for microtitolation (Corning, black, NBS). The control wells were without inhibitor.

The inhibition activity of MMP was expressed in relative fluorescence unit (RFU). The percentage of inhibition was calculated using control reactions without inhibitor.

$IC_{50}$ was determined using the formula: $V_i/V_o=1/(1+[I]/IC_{50})$, wherein $V_i$ is the initial rate of the substrate scission in presence of the inhibitor at the concentration [I] and $V_o$ is the initial rate in the absence of inhibitor. The results were analyzed with the SoftMax Pro software and the GraFit software.

EXAMPLE 29

Inhibition of ADAMS: Activity on TACE (ADAM17)
Method 1: (only TACE)

The human recombinant TACE, from CalBiochem, was dissolved in FAB buffer (Tris 50 mM, pH=7.5, NaCl 150 mM, $CaCl_2$ 10 mM, Brij 35 0.05% and DMSO 1%) at the concentration of 200 µg/mL (2.85 µM) as stock solution. For the assay measurements, the stock solutions of the inhibitor (DMSO, 100 mM) were further diluted up to seven different concentrations (0.01 nM-300 µM) in FAB buffer. A solution of the enzyme (final concentration 3 nM) and the solutions of the inhibitors at different concentrations were incubated in FAB for 20 minutes at 25° C. After the addition of a 200 µM solution of the substrate Mca-Lys-Pro-Leu-Gly-Leu-Dap (Dnp)-Ala-Arg-$NH_2$ (Bachem) in DMSO (final concentration 2 µM), the hydrolysis was monitored for 20 min, recording the increase in fluorescence ($\lambda_{ex}$=325 nm, $\lambda_{em}$=400 nm) using a Molecular Device SpectraMax Gemini XS plates reader. The assays were made in triplicate in a total volume of 200 µl per well, on 96 well microplates (Corning, black, NBS). The inhibition activity of TACE was expressed in relative fluorescent units (RFU). The percentage of inhibition was calculated based in respect to the blanks control without inhibitor. The $IC_{50}$ was determined following the equation: $V_i/V_o=1/(1+[I]/IC_{50})$, where $V_i$ is the initial rate of the hydrolysis of the substrate in the presence of the inhibitor at the concentration [I] and $V_o$ is the initial rate in the absence of inhibitor. The results were analysed using the software SoftMax Pro and GraFit.

Method 2: TACE and Other ADAMs

For TACE and other ADAMs the methods described in the literature could be used as well. See, for instance, Jin, G et al Anal Biochemistry 2002, 269; Amour, A et al Febs Lett., 2000, 275; English, W R et al, J. Biol. Chem. 2000, 14046; and Fourie, A M et al J. Biol. Chem. 2003, 30469.

EXAMPLE 30

Inhibition of ADAMTS

For the different ADAMTs the methods employed are those described by Rodriguez-Manzaneque, J C et al, Biochem. Biophys. Res. Commun., 2002, 501; Anderson, P J et al, J. Biol. Chem. 2006, 850; Kokame, K et al, Br. J. Haem., 2005, 93; Miller J A et al, Anal. Biochem., 2003, 260; Noe, M C et al, Bioorg. & Med. Chem. Lett., 2005, 2808; US 2006/0014233.

The following tables from 1 to IV resume the obtained results of biological activity for some representative compounds of the invention.

TABLE I

Inhibitory activity of representative compounds of formula (I) towards selected proteases (e.g. MMP-1, MMP-2 and MMP-9)

| Compound | $IC_{50}$ (µM) [or as nM (*)] | | |
| --- | --- | --- | --- |
| | MMP-1 | MMP-2 | MMP-9 |
| 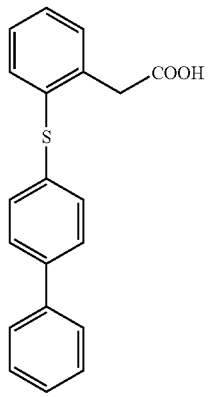<br>19a | 334 ± 5.7 | 0.33 ± 0.026 | 6.7 ± 0.3 |

TABLE I-continued

Inhibitory activity of representative compounds of formula (I) towards selected proteases (e.g. MMP-1, MMP-2 and MMP-9)

| Compound | IC$_{50}$ (μM) [or as nM (*)] | | |
|---|---|---|---|
|  | MMP-1 | MMP-2 | MMP-9 |
| 5-bis | 189 ± 28 | 11 ± 1.1 | 95 ± 8.7 |
| 10-bis | 83 ± 11 | 12 ± 0.8 | 35 ± 2.7 |
| 13-bis | 186 ± 8 | 7 ± 0.5 | 47 ± 2.7 |

TABLE I-continued

Inhibitory activity of representative compounds of formula (I) towards
selected proteases (e.g. MMP-1, MMP-2 and MMP-9)

| Compound | IC$_{50}$ (μM) [or as nM (*)] | | |
|---|---|---|---|
| | MMP-1 | MMP-2 | MMP-9 |
| 15-bis (structure: 2-[(4-biphenylyl)thio]phenyl group with -CH(COOH)CH$_2$CH$_2$COOH) | 190 ± 10 | 1.8 ± 0.16 | 17 ± 0.96 |
| 21a | 171000 ± 5000(*) | 41.1 ± 1.4(*) | 1200 ± 200(*) |
| 30 | — | 37.9 ± 2.2(*) | 1112 ± 136(*) |
| 24 | — | 6.8 ± 0.53(*) | 120 ± 17(*) |

The data reported in table I clearly provide evidence that the compounds of the invention are endowed with a remarkable inhibitory activity against MMP-2 and against MMP-9 whilst are scarcely active in the inhibition of MMP-1.

In addition, the activity of some of the compounds of formula (I) of the invention, in particular those wherein the parameter E is directly linked to the phenylene ring (e.g. those same compounds wherein m=0), resulted to be advantageously selective in the inhibition of MMP-2 over MMP-9.

TABLE II

Inhibitory activity of representative compounds of
formula (I) towards selected proteases (e.g. MMP-2,
MMP-9 and MMP-14)

| Compound | IC$_{50}$ (μM) [or as nM (*)] | | |
|---|---|---|---|
| | MMP-2 | MMP-9 | MMP-14 |
| 47 | 62472 ± 6268 (*) | 83514 ± 5870 (*) | 115623 ± 9792 (*) |
| 22 | 114 ± 5 (*) | 832 ± 79 (*) | 3649 ± 200 (*) |
| 54 | 159.3 ± 6.8 (*) | — | 9953 ± 916 (*) |
| 56a | 27.2 ± 1.6 (*) | — | 6496 ± 597 (*) |
| 86 | 384 ± 31 (*) | 2472 ± 212 (*) | 8327 ± 511 (*) |
| 48 | 41.8 ± 5.1 | — | 73.1 ± 7.9 |
| 106 | 22.5 ± 2.1 | — | 64.7 ± 2.9 |
| 25 | 5.34 ± 0.65 | 17.7 ± 1.4 | 127.3 ± 6.9 |
| 57 | 65.8 ± 5.8 | 73.7 ± 7.8 | 155.7 ± 9.5 |

The data reported in table II clearly provide evidence that the compounds of the invention are endowed with a remarkable inhibitory activity against MMP-2 and/or against MMP-9 whilst are scarcely active in the inhibition of MMP-14.

TABLE III

Inhibitory activity of representative compounds of
formula (I) towards selected proteases (e.g. MMP-2,
MMP-9 and MMP-14)

| Compound | IC$_{50}$ (nM) [or as μM (*)] | | |
|---|---|---|---|
| | MMP-2 | MMP-9 | MMP-14 |
| 72 | 571 ± 45 (pH 6.7) | 168 ± 27 (pH 6.7) | 1949 ± 212 (pH 6.7) |
| 8 | 12.2 ± 1.6(*) | 17.8 ± 1.3(*) | 79 ± 6(*) |
| 38 | 20.5 ± 2.1(*) | 101.4 ± 5.9(*) | 527.5 ± 58.1(*) |
| 39 | 183.3 ± 18.4(*) | 105.7 ± 23.6(*) | 272.3 ± 18.7(*) |
| 43 | 78.6 ± 6.3(*) | 47.3 ± 2(*) | 260.5 ± 30.1(*) |
| 11 | 20000 ± 8000 | 48700 ± 8600 | 297000 ± 64000 |
| 13 | 568 ± 31 | 105 ± 13 | — |

The data reported in table III clearly provide evidence that the compounds of the invention are endowed with inhibitory activity against MMP-2 and against MMP-9 whilst are scarcely active in the inhibition of MMP-14.

TABLE IV

Inhibitory activity of representative compounds of
formula (I) towards selected proteases (e.g. MMP-2,
MMP-9 and TACE)

| Compound | IC$_{50}$ (nM) | | |
|---|---|---|---|
| | MMP-2 | MMP-9 | TACE |
| 21a | 41.1 ± 1.4 | 1200 ± 200 | 13450 ± 1933 |
| 21b | 6200 ± 300 | — | 10200 ± 670 |
| 24 | 6.8 ± 0.53 | 120 ± 17 | 46245 ± 5337 |

The data reported in table IV clearly provide evidence that the compounds of the invention are endowed with inhibitory activity against MMP-2 and against MMP-9, whilst are scarcely active in the inhibition of TACE.

Remarkably, however, another representative compound of formula (I) of the invention wherein X is an oxygen atom and E is an alkenylene moiety, rather than a carbocyclic or heterocyclic ring, namely the compound (21c) having the formula reported below, has been tested against the above metalloproteases and resulted to be endowed with inhibitory activity selectively addressed to TACE [(IC$_{50}$ nM): 462±21] over MMP-2 [(IC$_{50}$ nM): 1450±33].

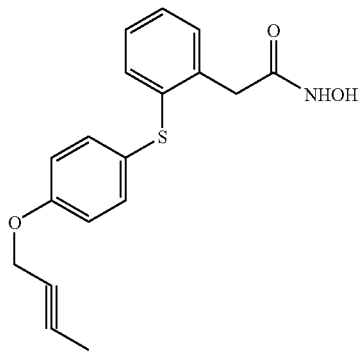

21c

The invention laimed is:

1. A compound of formula (I)

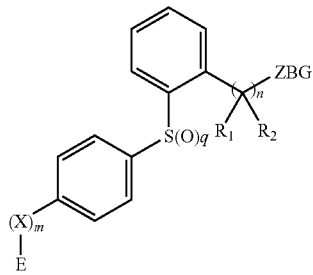

(I)

wherein:
q and n are 0 and m is 1;
q is 0, n is 1 and m is 0;
q is 1, and n and m are both 0;
q is 1, n is 0 and m is 1;
q is 1, n is 1 and m is 0;
q, n and m are all 1;
q is 2 and n and m are both 0;
q is 2, n is 0 and m is 1;
q is 2, n is 1 and m is 0;or
q is 2 and n and m are both 1; and wherein
ZBG is the chelating moiety for the catalytic zinc atom and it is selected from the group consisting of:
hydroxamate —CONHOH;
carboxylate —COOH;
carboxamide —CONHR$_4$, —CON(R$_4$)$_2$ or —CONR$_6$R$_7$;
phosphonate —P(=O)(R$_4$)OH;
sulfonimide —CONHSO$_2$(R'$_4$);
sulfonamide —SO$_2$NHR$_4$; and
thiol —SH;
or it is a group of formula:

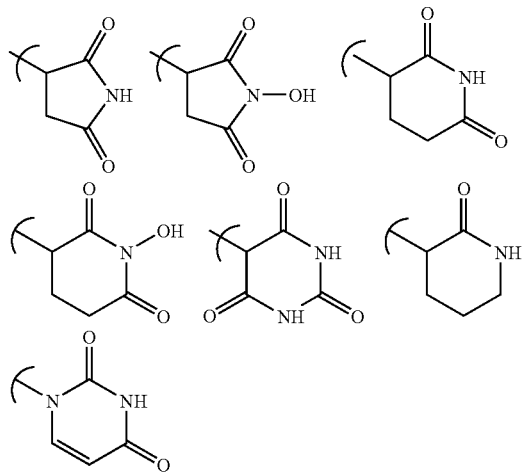

R$_4$ is selected, independently in each occurrence, from the group consisting of hydrogen, hydroxyl, straight or branched C$_1$-C$_{10}$ alkyl and fluoroalkyl, optionally substituted aryl or 5 to 6 membered heteroaryl with from 1 to 2 heteroatoms or heteroatomic groups selected from N, NH, O and S; or R$_4$ is a group selected from —(CHR)$_p$—COOH, —(CHR)$_p$—CO—NHR', —(CHR)$_p$—NH$_2$, —(CHR)$_p$—NH—COR', —(CHR)$_p$—CH$_2$OH and —(CH$_2$)$_p$—CHR—OH;
p is an integer from 1 to 8;
R' is a straight or branched C$_1$-C$_6$ alkyl or an optionally substituted aryl or heteroaryl group as above defined;
R is selected from the group consisting of hydrogen, a C$_1$-C$_{10}$ saturated or unsaturated, either straight or branched, chain of carbon atoms optionally substituted by one or more substituents selected from hydroxyl, —ONO$_2$, —NR$_6$R$_7$, —COOH, —CONHR", —NH-COR", C$_1$-C$_6$ alkoxy, and optionally substituted aryl or heteroaryl groups as above defined;
R$_6$ and R$_7$ are selected, each independently, from hydrogen, C$_1$-C$_6$ saturated or unsaturated, either straight or branched, chain of carbon atoms optionally substituted with aryl or heteroaryl groups as above defined, or by a group selected from —CO-alkyl, —CO-aryl, —CO-heteroaryl,
—CONH-alkyl, —CONH-alkyl-ONO$_2$, —CONH-acyl, —CONH-acyl-ONO$_2$,
—CONH-aryl, —CONH-heteroaryl, —SO$_2$-alkyl, —SO$_2$NH$_2$,
—SO$_2$NH-alkyl, —SO$_2$NH-aryl, and —SO$_2$NH-heteroaryl;
or, together with the nitrogen atom to which they are linked, R$_6$ and R$_7$ form a 5 to 6 membered heterocyclic ring optionally further containing an additional heteroatom or heteroatomic group selected from N, NH, O and S, optionally substituted and/or benzocondensed;
R" is selected from a straight or branched C$_1$-C$_6$ alkyl, alkyl-O—NO$_2$ or acyl group, or it is an optionally substituted aryl, heteroaryl, arylalkyl, heteroarylalkyl, acylaryl or acylheteroaryl group;
R'$_4$ is selected, independently in each occurrence, from the meanings of R$_4$ except than hydrogen;
R$_1$ and R$_2$ are selected, each independently, from the meanings of R or, together with the carbon atom to which they are linked, R$_1$ and R$_2$ form an optionally substituted 3 to 6 membered carbocyclic or heterocyclic ring having from 1 to 2 heteroatoms or heteroatomic groups selected from N, NH, N—COR", O and S;
X is oxygen (—O—);

E is a straight or branched alkynyl group with from 2 to 6 carbon atoms in the hydrocarbon chain, or it is an optionally substituted aromatic, 5 to 6 membered carbocyclic or heterocyclic ring having 1 or 2 heteroatoms or heteroatomic groups selected from N, NH, O and S;

with the proviso that when q is 2, ZBG is other than hydroxamate [—CONHOH] or carboxylate [—COOH];

and the pharmaceutically acceptable salts thereof.

2. A compound according to claim 1 wherein any of the aryl or heteroaryl groups is optionally substituted by one or more $R_5$ groups selected from: —$CH_3$, —$CH_2CH_3$,
- —$CH(CH_3)_2$, —$CH_2OH$, —$CH_2ONO_2$,
- —$(CH_2)_rCO_2H$, —$(CH_2)_rCONH$-alkyl, —$(CH_2)_rCONH$-aryl,
- —$(CH_2)_rCONH$-heteroaryl, —$(CH_2)_rNH_2$, —$CH_2)_r$N-HCO-alkyl,
- —$(CH_2)_rNHCO$-aryl, —$(CH_2)_rNHCO$-heteroaryl, —$(CH_2)_rCH_2OH$ (with r =1-8), —$CF_3$, —$NO_2$, OH, F, Cl, Br, I, —$OCH_3$, —$OCH(CH_3)_2$,
- —$O(CH_2)_rCOOH$, —$O(CH_2)_rNH_2$, —$O(CH_2)_rCH_2OH$ (with r =1-8),
- —$SO_sCH_3$, —$SO_sCH(CH_3)_2$, -$SO(CH_2)_rCOOH$, -$SO_s(CH_2)_rNH_2$,
- —$SO_s(CH_2)_rCH_2OH$ (with r =1-8 and s =0-2), —$SO_2NH_2$,
- —$SO_2NH$-alkyl, —$SO_2NH$-aryl, —$SO_2NH$-heteroaryl,
- —NH-alkyl,
- —NH-aryl, —NH-heteroaryl, —NHCO-alkyl, —$NHSO_2$-alkyl,
- —$NHSO_2$-aryl, and —$NHSO_2$-heteroaryl.

3. A compound according to claim 1 wherein any of the aryl or heteroaryl groups is optionally substituted by one or more $R_5$ groups selected from: $C_1$-$C_4$ alkoxy, alkylthio and alkylsulphonyl groups.

4. A compound according to claim 1 wherein any of the aryl or heteroaryl groups is optionally substituted by one or more $R_5$ groups selected from methoxy, methylthio and methylsulphonyl.

5. A compound according to claim 1 wherein, within the meanings of $R_6$ and $R_7$, the optionally substituted 5 to 6 membered heterocyclic ring is selected from the group consisting of:

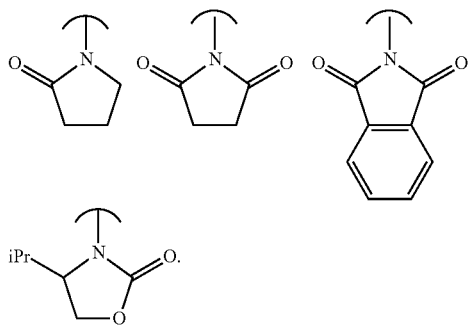

6. A compound according to claim 1 wherein, within the meanings of $R_1$ and $R_2$, the carbocyclic or heterocyclic ring they may form together with the carbon atom to which they are linked is optionally substituted by one or more $R_8$ groups selected from: $C_1$-$C_6$ saturated or unsaturated, either straight or branched, hydrocarbon chains, or groups selected from aryl, arylalkyl, heteroaryl, heteroarylalkyl, —COOH,
- —COO-alkyl, —COO-aryl, —COO-heteroalkyl, —COO-alkylaryl,
- —COO-alkylheteroaryl, —CO-alkyl, —CO-aryl, —CO-heteroaryl,
- —CONH-alkyl, —CONH-alkyl-$ONO_2$, —CONH-acyl, —CONH-acyl-$ONO_2$, —CONH-aryl, —CONH-heteroaryl, —$SO_2$-alkyl, —$SO_2NH_2$, —$SO_2NH$-alkyl, —$SO_2NH$-aryl and —$SO_2NH$-heteroaryl groups.

7. A compound according to claim 1 wherein, within the meanings of $R_1$ and $R_2$, the optionally substituted carbocyclic or heterocyclic ring they may form together with the carbon atom to which they are linked, is selected from the group consisting of:

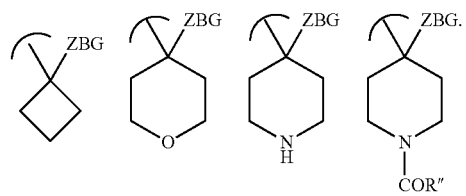

8. A compound according to claim 1 wherein ZBG is a group selected from —COOH, —$CONHSO_2CH_3$, —$CONHSO_3H$, —$CONHSO_2CF_3$, —P(=O)(OH)$_2$, —$CONH_2$, —$SO_2NH_2$, —SH, a group —$CONR_6R_7$ having formula below

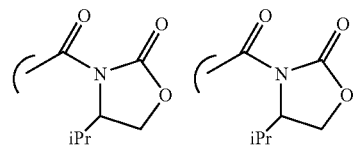

and a group of formula

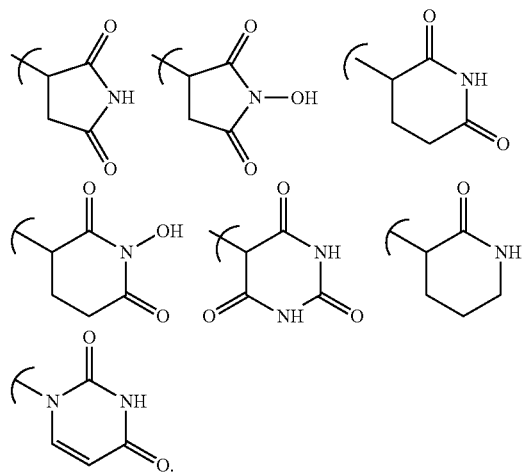

9. A compound according to claim 1 selected from the group consisting of:
- 2-(4-(4-methoxyphenoxy)phenylthio)benzoic acid(4);
- N-hydroxy-2-(4-(4-methoxyphenoxy)phenylthio)benzamide(5);
- 2-(4-(4-methoxyphenoxy)phenylsulphinyl)benzoic acid (6);
- N-hydroxy-2-(4-(4-methoxyphenoxy)phenylsulphinyl) benzamide (7);
- 2-(4-(4-methoxyphenoxy)phenylthio)-N-(methylsulphonyl) benzamide(8);
- 2-(2-biphenyl-4-ylthio)phenyl)acetic acid(19a);
- 2-(2-biphenyl-4-ylthio)phenyl)-N-hydroxyacetamide (21a);

2-(2-(4-(but-2-iniloxy)phenylthio)phenyl)-N-hydroxyac-
  etamide(21c);
2-(2-(4'-methoxybiphenyl-4-ylthio)phenyl)acetic acid
  (22);
N-hydroxy-2-(2-(4'-methoxybiphenyl-4-ylthio)phenyl)
  acetamide(24);
2-(2-(4'-methoxybiphenyl-4-ylthio)phenyl)-N-(methyl
  sulphonyl)acetamide(25);
N-hydroxy-2-(2-(4-(thiophene-3-yl)phenylthio)phenyl)
  acetamide(30);
N-hydroxy-2[2-(4'-methylthio-biphenyl-4-ylthio)-phe-
  nyl]-acetamide(32);
N-hydroxy-2-(2-(4-pyridin-4-yl-phenylthio)-phenyl)-ac-
  etamide(34);
2-(4-(4-methoxyphenoxy)phenylsulphonyl)-N-(methyl-
  sulphonyl)benzamide(38);
2-(2-(4-(4-methoxyphenoxy)phenylsulphonylphenyl)-N-
  (methyl sulphonyl)acetamide(43);
2-(4'-methoxybiphenyl-4-ylthio)benzoic acid (47);
2-(4'-methoxybiphenyl-4-ylthio)-N-(methylsulphonyl)
  benzamide(48);
2-(4'-methoxybiphenyl-4-yl-sulphonyl)-N-(methyl sul-
  phonyl)benzamide(106);
2-(4'-methoxybiphenyl-4-ylthio)-N-(trifluoromethyl
  sulphonyl)benzamide(49);
2-(2-(4'-methoxybiphenyl-4-sulphonyl)phenyl)-N-(me-
  thyl
  sulphonyl)acetamide(52);
2-(2-(4'-methoxybiphenyl-4-ylthio)phenyl)propionic acid
  (54);
N-hydroxy-2-(2-(4'-methoxybiphenyl-4-ylthio)phenyl)
  propanamide(56a);
N-hydroxy-2-(2-(4'-methoxybiphenyl-4-ylthio)phenyl)
  pent-4-enamide (56b);
2-(2-(4'-methoxybiphenyl-4-ylthio)phenyl)-N-(methyl
  sulphonyl)propanamide(57);
2-(4-(4-methoxyphenoxy)phenylthio)benzylphosphonic
  acid (70);
2-(4-(4-methoxyphenoxy)phenylsulphonyl)benzyl phos-
  phonic acid(72);
2-(4'-methoxybiphenyl-4-ylthio)benzylphosphonic acid
  (85);
2-(4'-methoxybiphenyl-4-ylsulphonyl)benzylphosphonic
  acid(86);

and compounds having any one of the following formulae:

5-bis

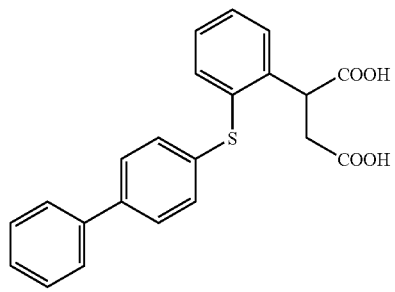

-continued 7a-bis

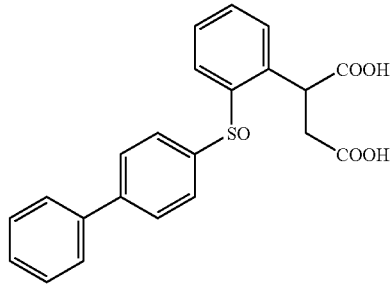

8-bis

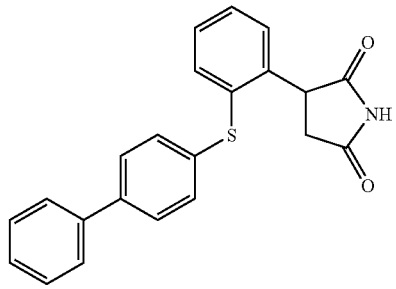

10-bis

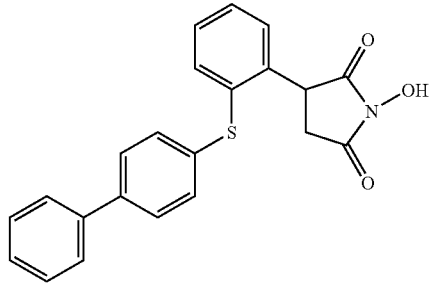

11-bis

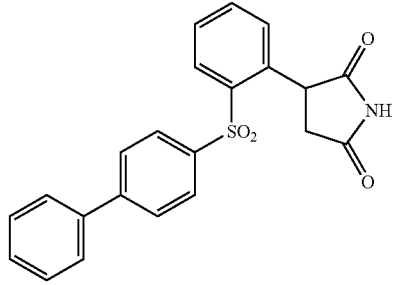

13-bis

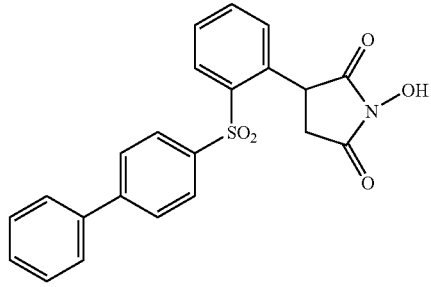

15-bis

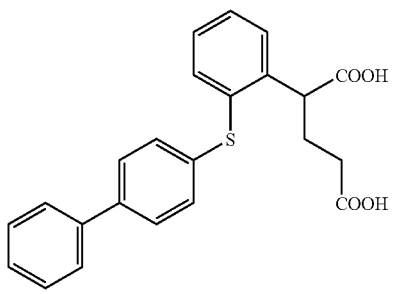

17a-bis

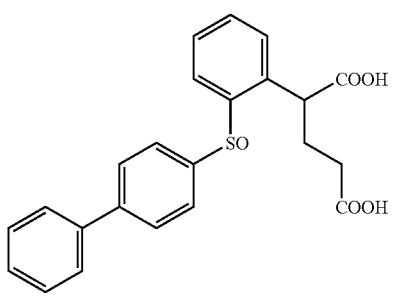

20-bis

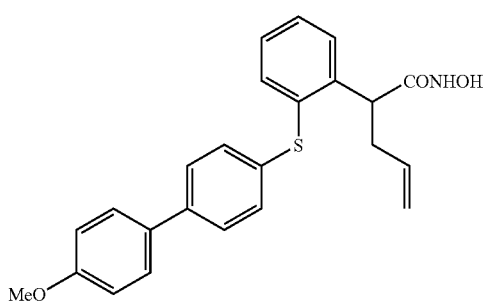

22-bis

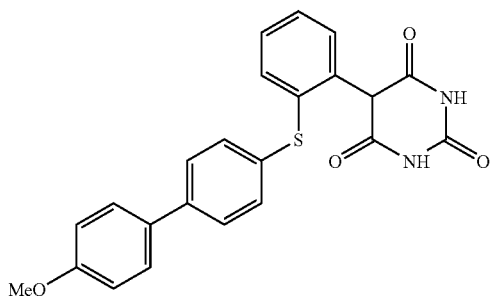

24-bis

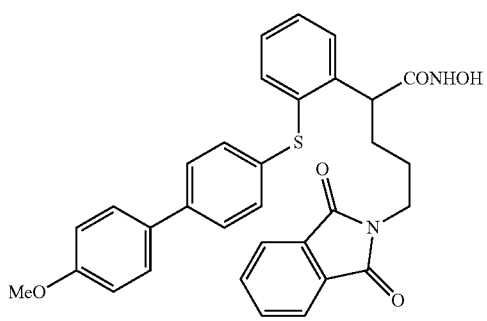

25-bis

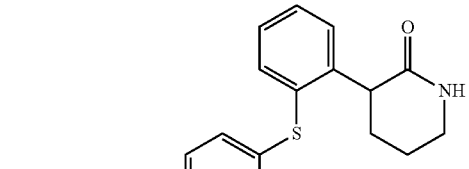

10a-ter

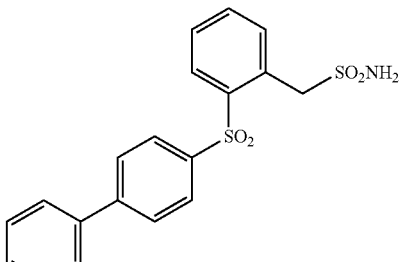

10b-ter

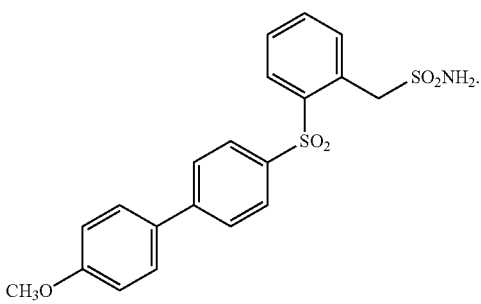

10. A pharmaceutical composition comprising, as the active ingredient one or more compounds according to claim 1, or pharmaceutically acceptable salts thereof, together with one or more pharmaceutically acceptable carriers, diluents or excipients.

11. A method for the treatment of pathological conditions associated with the impaired activity of zinc metalloproteinases in mammals, comprising the administration to a mammal in need thereof, of a therapeutically effective amount of a compound according to claim 1, or of a pharmaceutically acceptable salt thereof.

12. A method according to claim 11 wherein the mammal is a human and the pathological condition is a degenerative disorder.

13. A compound according to claim 1, wherein —(X)m-E is selected from the group consisting of: 2-butinyloxy, pheny, pyridyl, thienyl, methoxyphenyl, methylthiophenyl, phenoxy and methoxyphenoxy.

14. A method according to claim 12 wherein the degenerative disorder is a tumor.

15. The method according to claim 11 wherein the pathological condition is selected from the group consisting of: tissue disruption, fibrotic disease, pathological degradation of the matrix, bad repair of injuries, cardiovascular disease, pulmonary disease, renal disease, hepatic disease, ophthalmic disease and disease of the central nervous system.

16. The method according to claim 11 wherein the pathological condition is selected from the group consisting of: osteoarthritis, rheumatoid arthritis, septic arthritis, tumour invasion, tumour metastasis, tumour angiogenesis, decubitus ulcer, gastric ulcer, corneal ulcer, ocular angiogenesis, macular degradation, corneal cicatrization, periodontal disease, scleritis, AIDS, sepsis and septic shock, hepatic cirrhosis, diabetes, pulmonary fibrosis, otosclerosis, atherosclerosis, multiple sclerosis, epidermic ulcerations, lack in injury repair, adhesion phenomena, cicatrization of injuries, cardiac decompensation, dilated cardiomyopathy coronary thrombosi aortic and cerebral aneurism restenosis, osteoporosis, chronic coronary obstructive disease, emphysema, pathologies of rejection of transplanted organs, —asthma allergic reaction, proteinuria, pathologies of the bone, Alzheimer's disease, central nervous system diseases associated with nitrosative and oxidative stresses, autoimmune disorders, Huntington's disease, Parkinson's disease, migraine, depression, peripheral neuropathy, pain, cerebral amyloid angiopathy, nootrope or cognitive enhancement, amyotrophic lateral sclerosis, and multiple sclerosis.

\* \* \* \* \*